US007156814B1

(12) United States Patent
Williamson, IV et al.

(10) Patent No.: US 7,156,814 B1
(45) Date of Patent: **\*Jan. 2, 2007**

(54) APPARATUS AND METHOD FOR HARVESTING AND HANDLING TISSUE SAMPLES FOR BIOPSY ANALYSIS

(75) Inventors: Warren P. Williamson, IV, Loveland, OH (US); Stephen Whitlach, Cincinnati, OH (US); Dominic DiNovo, Columbus, OH (US); Douglas Allen, Lyons, CO (US); Thomas Ward, Columbus, OH (US)

(73) Assignee: Biopath Automation, L.L.C., Loveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/890,177

(22) PCT Filed: Oct. 5, 1998

(86) PCT No.: PCT/US98/20478

§ 371 (c)(1),
(2), (4) Date: Jul. 27, 2001

(87) PCT Pub. No.: WO00/19897

PCT Pub. Date: Apr. 13, 2000

Related U.S. Application Data

(63) Continuation-in-part of application No. 08/645,750, filed on May 14, 1996.

(51) Int. Cl.
*A61B 10/00* (2006.01)
*G01N 1/30* (2006.01)
*G01N 33/48* (2006.01)
*C12M 1/12* (2006.01)
*C12M 1/22* (2006.01)
*C12M 3/00* (2006.01)

(52) U.S. Cl. ................. 600/562; 435/40.52; 435/297.5; 435/305.1

(58) Field of Classification Search ........ 600/562–572; 435/294.1, 40.52, 40.5, 297.5, 305.1; 264/250, 264/275, 240; 206/455
See application file for complete search history.

(56) References Cited

U.S. PATENT DOCUMENTS 2,749,909 A  8/1956  Ullery et al. ................... 128/2

(Continued)

FOREIGN PATENT DOCUMENTS

GB  865889 A  4/1961
GB  1483574 A  8/1977

OTHER PUBLICATIONS

European Patent Office, Supplementary European Search Report in corresponding EP 02776027, Jul. 7, 2006.

Primary Examiner—Max F. Hindenburg
Assistant Examiner—Brian Szmal
(74) Attorney, Agent, or Firm—Wood, Herron & Evans, L.L.P.

(57) ABSTRACT

A sectional cassette (10) for use in a process for harvesting and handling tissue samples for biopsy analysis is disclosed. In the procedure, a tissue biopsy sample is placed on a tissue trapping supporting material (A') that can withstand tissue preparation procedures, and which can be cut with a microtome. The tissue is immobilized on the material, and the material and the tissue are held in the cassette (10) subjected to a process for replacing tissue fluids with wax. The tissue and supporting material are sliced for mounting on slides using a microtome. Harvesting devices and containers (200) using the filter material (202) are disclosed. An automated process is also disclosed.

73 Claims, 45 Drawing Sheets

U.S. PATENT DOCUMENTS

| | | | |
|---|---|---|---|
| 3,224,434 A | 12/1965 | Molomut et al. | 128/2 |
| 3,257,279 A | 6/1966 | Schain | 167/84.5 |
| 3,527,863 A | 9/1970 | Weichselbaum | 424/3 |
| 3,624,197 A | 11/1971 | Schain | 424/3 |
| 3,679,450 A | 7/1972 | Reightol | 117/3 |
| 3,691,097 A | 9/1972 | Stiles et al. | 252/440 |
| 3,814,670 A | 6/1974 | Freake et al. | 195/127 |
| 3,874,851 A | 4/1975 | Wilkins et al. | 23/230 |
| 3,961,097 A | 6/1976 | Gravlee, Jr. | 427/2 |
| 3,996,326 A | 12/1976 | Schachet | 264/158 |
| 4,025,306 A | 5/1977 | Studer | 23/230 |
| 4,199,558 A | 4/1980 | Henderson | 424/3 |
| 4,219,334 A | 8/1980 | Schluter et al. | 23/230 |
| 4,220,252 A | 9/1980 | Beall et al. | 220/307 |
| 4,224,277 A | 9/1980 | Macho et al. | 422/57 |
| 4,261,474 A | 4/1981 | Cohen | 215/250 |
| 4,340,066 A | 7/1982 | Shah | 128/749 |
| 4,353,856 A | 10/1982 | Mück et al. | 264/240 |
| 4,427,614 A | 1/1984 | Barham et al. | 264/210.1 |
| 4,435,507 A | 3/1984 | Stenkvist | 435/262 |
| 4,439,319 A | 3/1984 | Rock | 210/238 |
| 4,497,792 A | 2/1985 | Gindler | 424/3 |
| 4,545,831 A | 10/1985 | Ornstein | 156/57 |
| 4,557,903 A | 12/1985 | McCormick | 422/101 |
| 4,656,047 A | 4/1987 | Kok et al. | 427/2 |
| 4,695,339 A | 9/1987 | Rada | 156/80 |
| 4,752,347 A | 6/1988 | Rada | 156/382 |
| 4,801,553 A | 1/1989 | Owen et al. | 436/174 |
| 4,817,631 A | 4/1989 | Schnepp-Pesch et al. | 128/753 |
| 4,820,504 A | 4/1989 | Battifora | 424/3 |
| 4,839,194 A | 6/1989 | Malluche et al. | 427/2 |
| 4,849,173 A | 7/1989 | Chang | 422/56 |
| 4,870,975 A | 10/1989 | Cronk et al. | 428/749 |
| 4,887,612 A | 12/1989 | Esser et al. | 128/751 |
| 4,961,432 A | 10/1990 | Guirguis | 128/760 |
| 4,962,036 A | 10/1990 | Cermak et al. | 435/34 |
| 4,971,783 A | 11/1990 | Bolton et al. | 424/3 |
| 4,971,912 A | 11/1990 | Buhl et al. | 436/52 |
| 5,024,830 A | 6/1991 | Linner | 424/3 |
| 5,047,008 A | 9/1991 | de Juan, Jr. et al. | 604/22 |
| 5,077,012 A | 12/1991 | Guirguis | 422/58 |
| 5,115,816 A | 5/1992 | Lee | 128/749 |
| 5,132,758 A | 7/1992 | Minami et al. | 357/23.4 |
| 5,137,710 A | 8/1992 | Smalley et al. | 424/3 |
| 5,170,800 A | 12/1992 | Smith et al. | 128/751 |
| 5,172,700 A | 12/1992 | Bencini et al. | 128/751 |
| 5,217,479 A | 6/1993 | Shuler | 606/180 |
| 5,224,488 A | 7/1993 | Neuffer | 128/751 |
| 5,284,753 A | 2/1994 | Goodwin, Jr. | 435/30 |
| 5,308,758 A | 5/1994 | Dahl | 435/30 |
| 5,312,758 A | 5/1994 | Ahlqvist | 436/63 |
| 5,318,589 A | 6/1994 | Lichtman | 606/205 |
| 5,817,032 A | 10/1998 | Williamson, IV et al. | 600/562 |
| 5,928,934 A | 7/1999 | McCormick | |
| 5,968,436 A | 10/1999 | Takezaki | 264/250 |
| 6,387,653 B1 | 5/2002 | Voneiff et al. | |

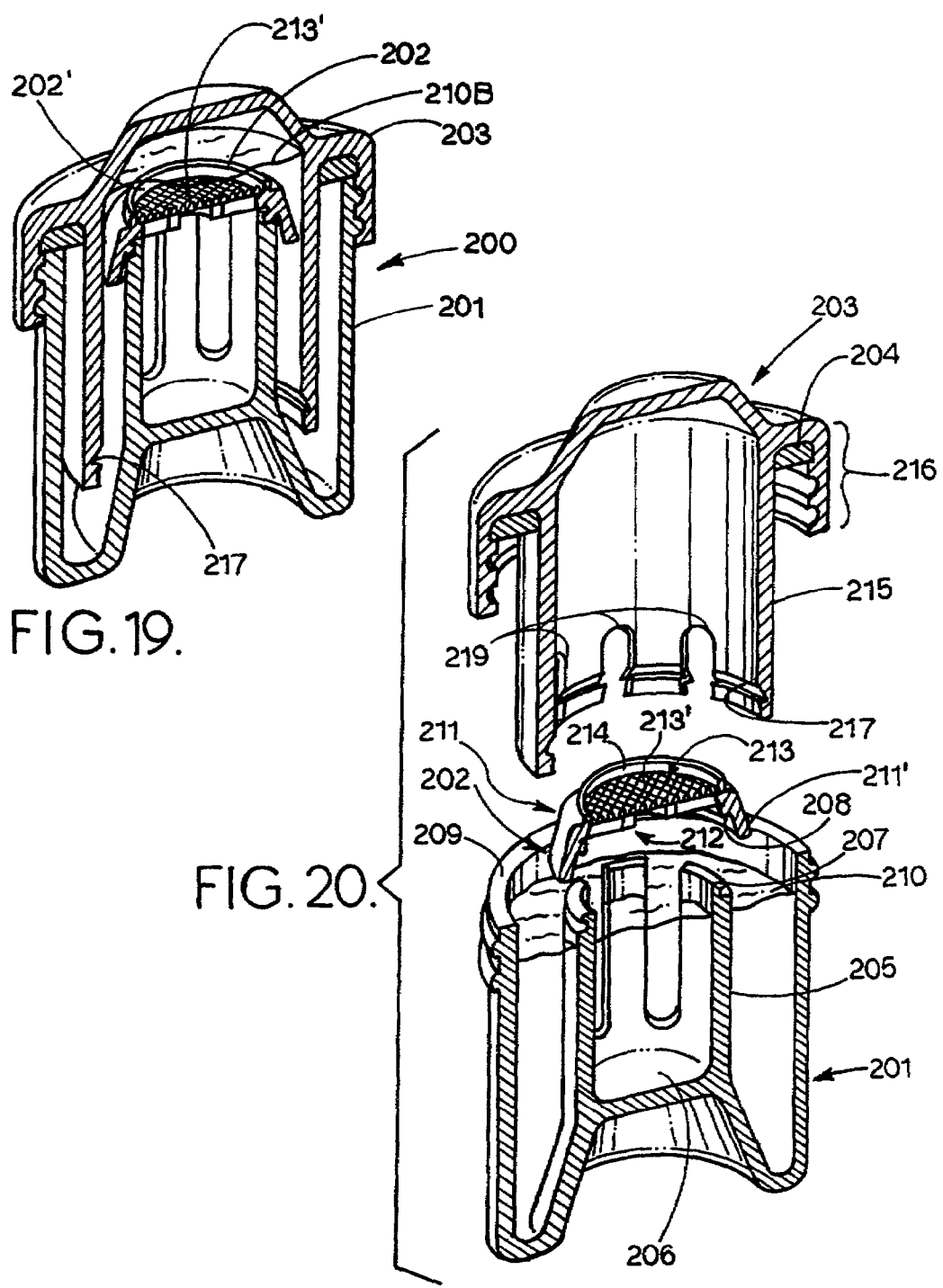

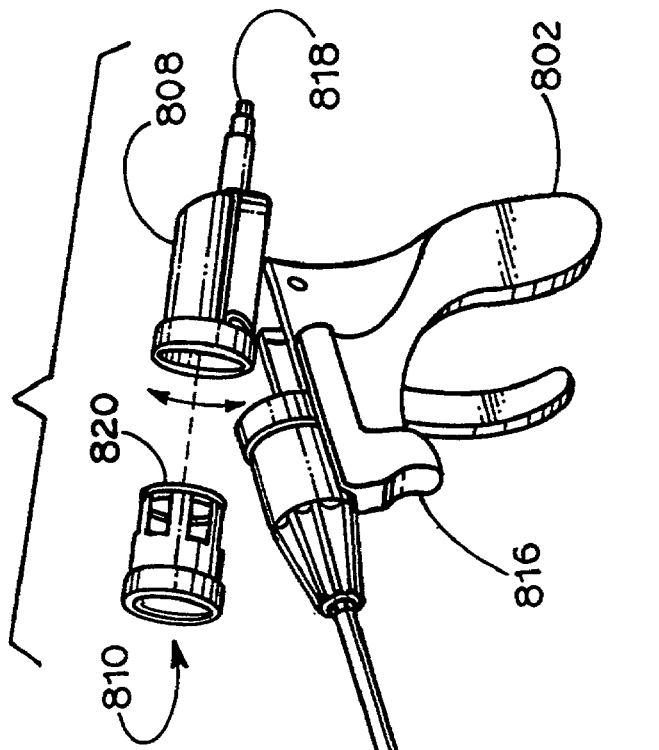
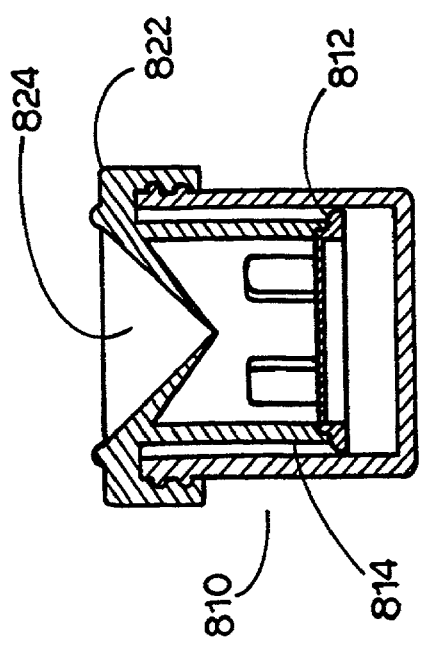

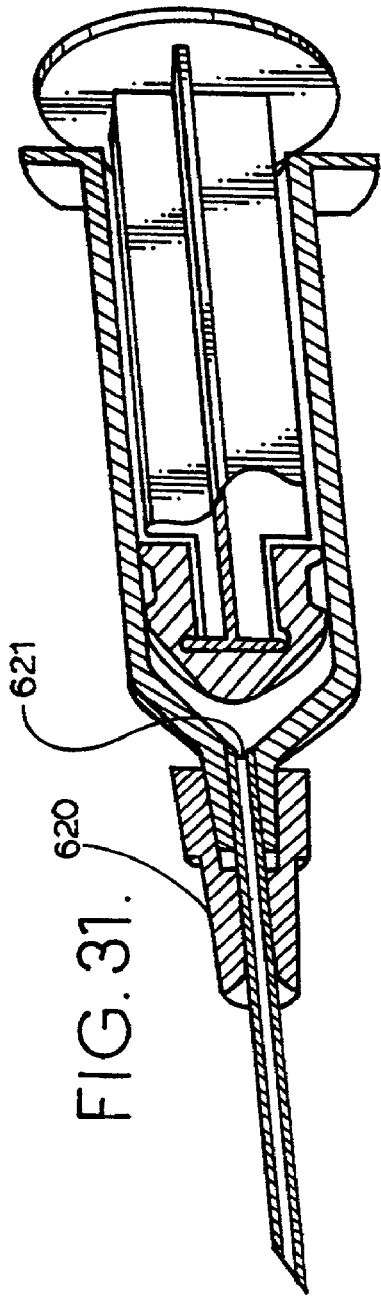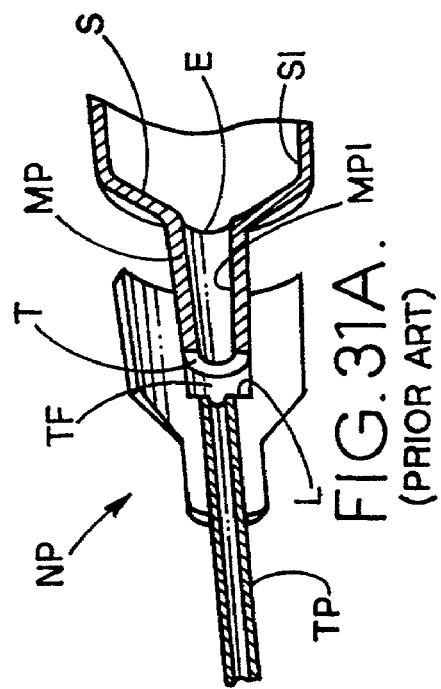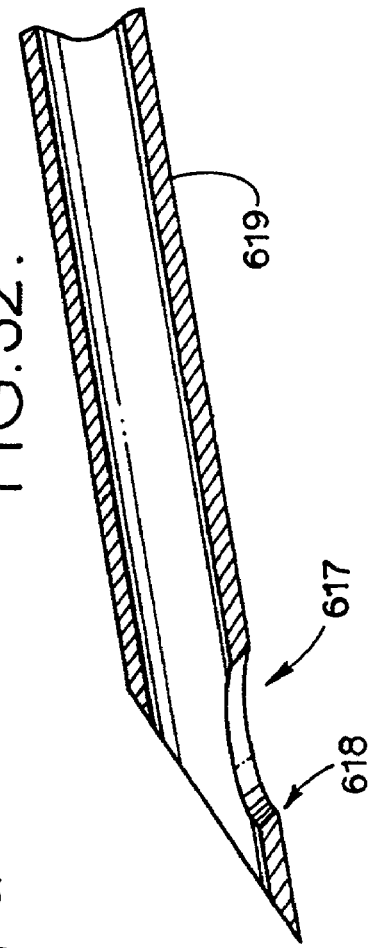

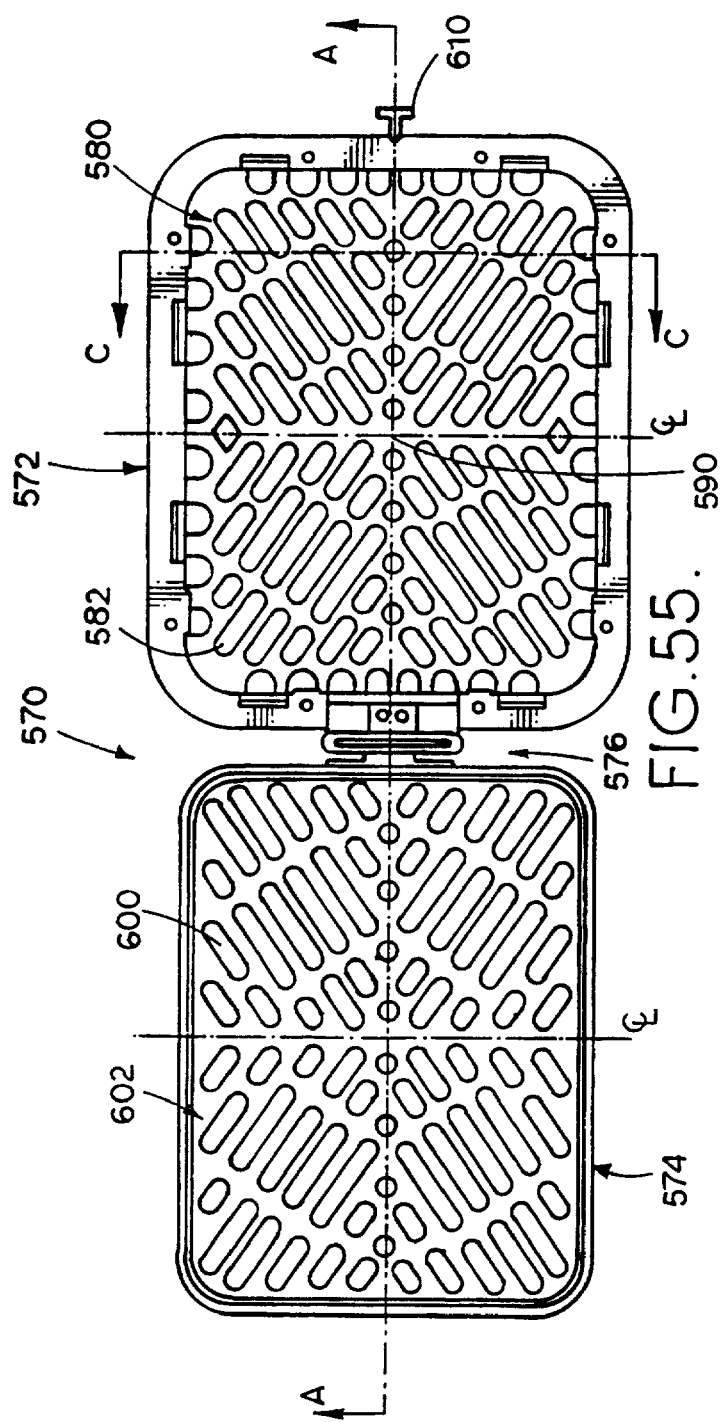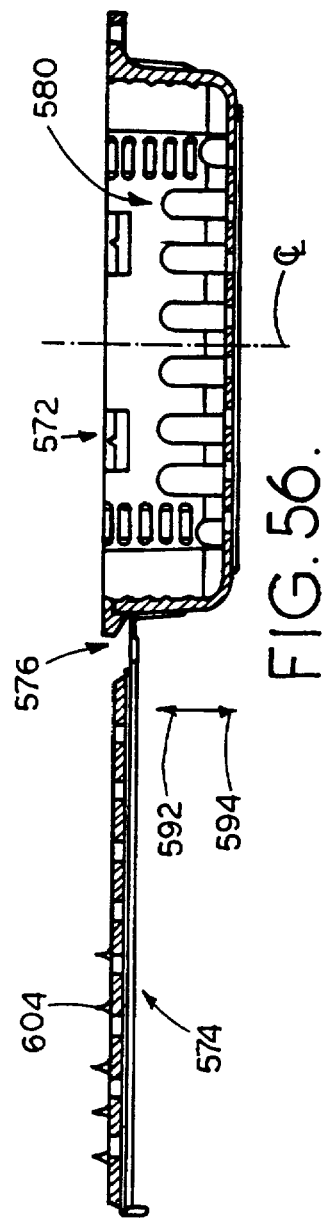
FIG. 55.
FIG. 56.

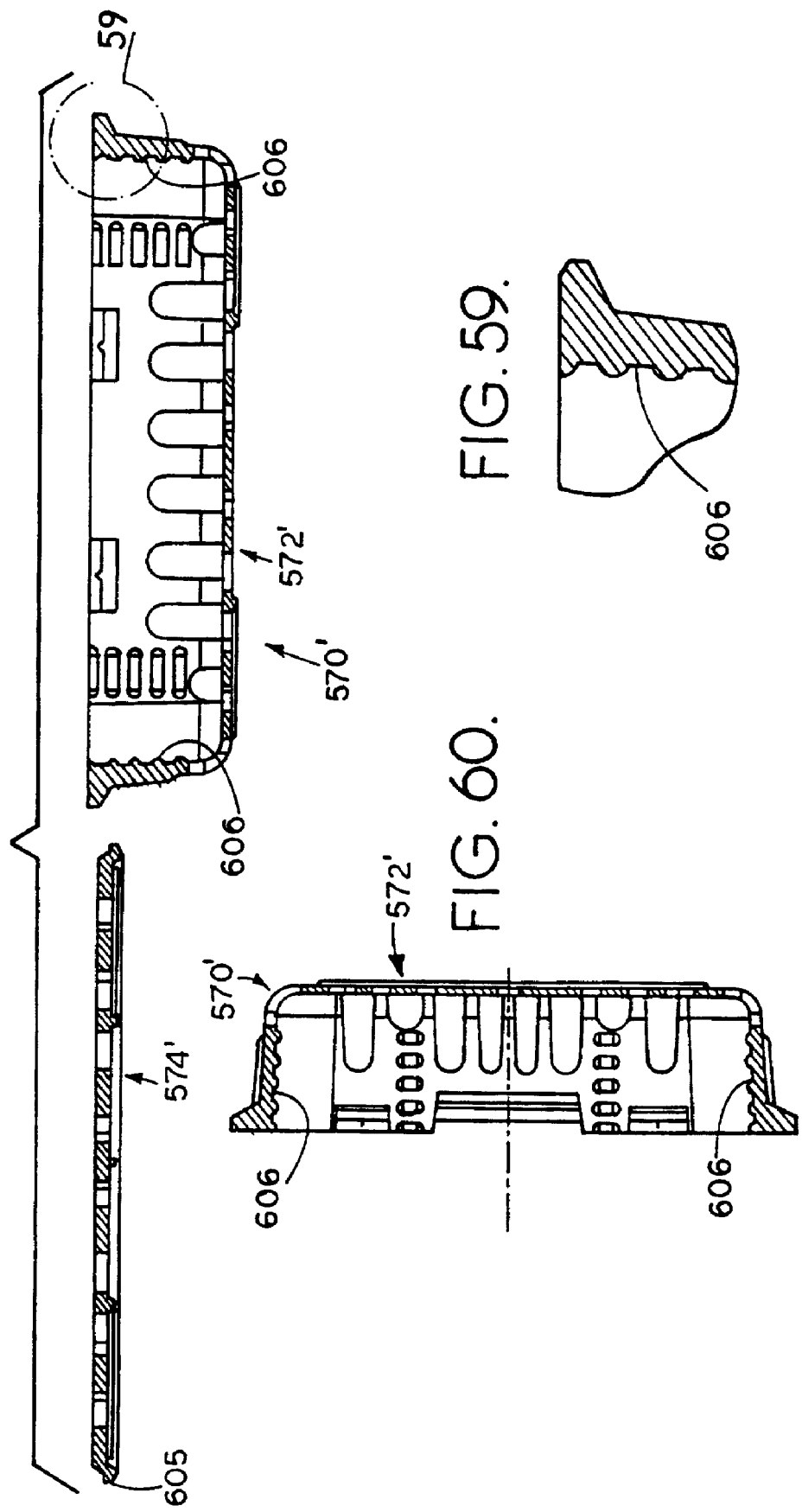

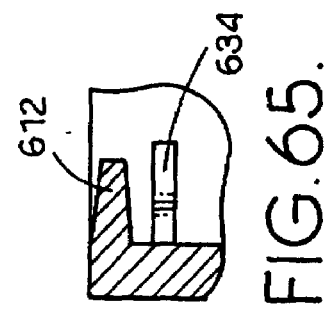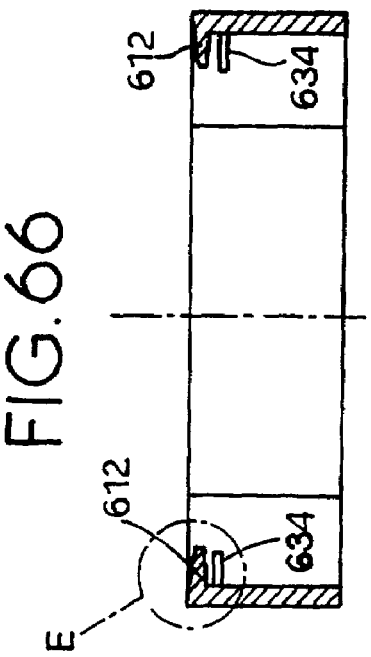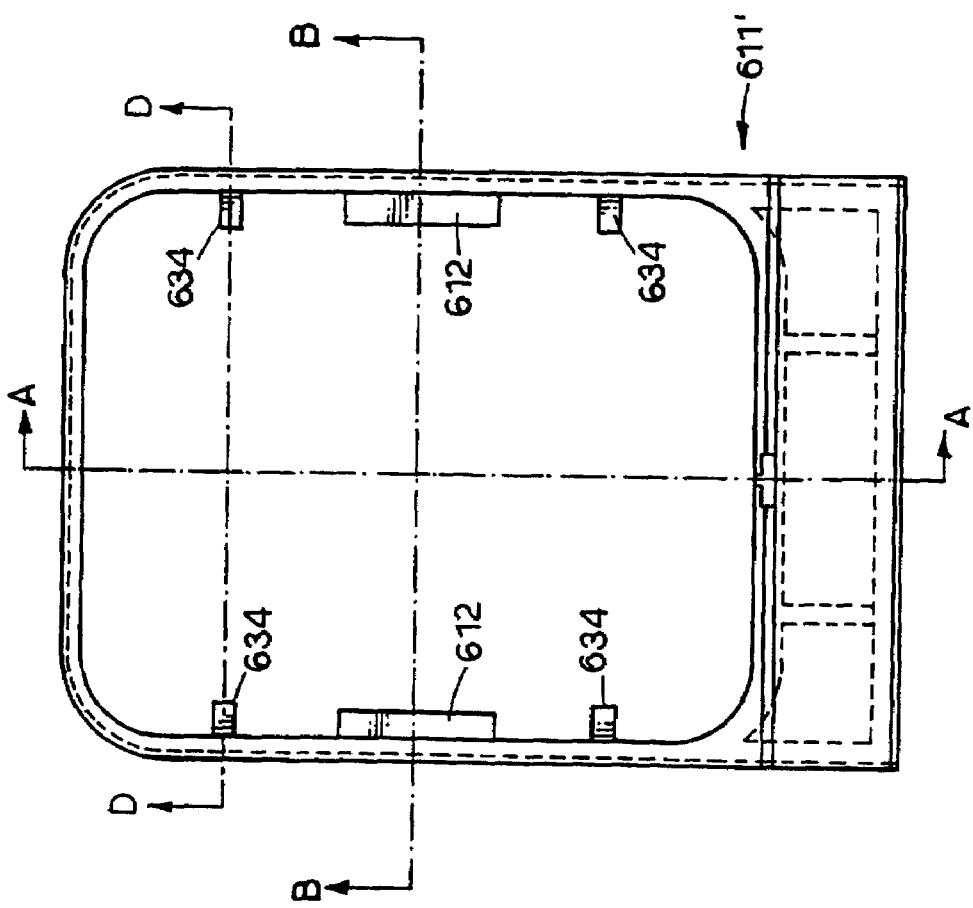

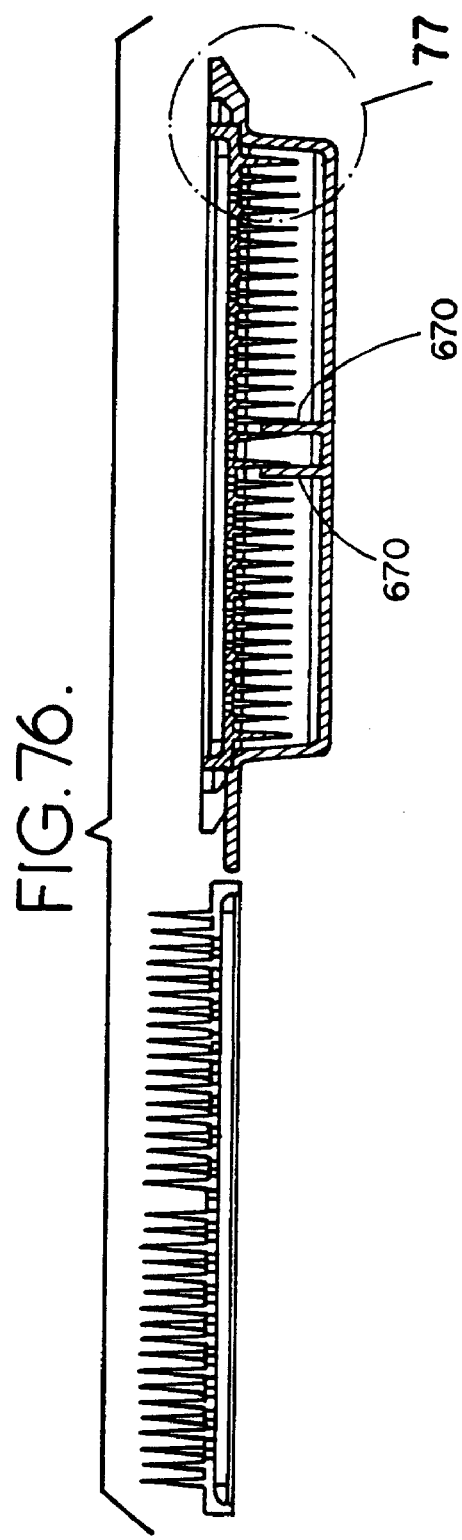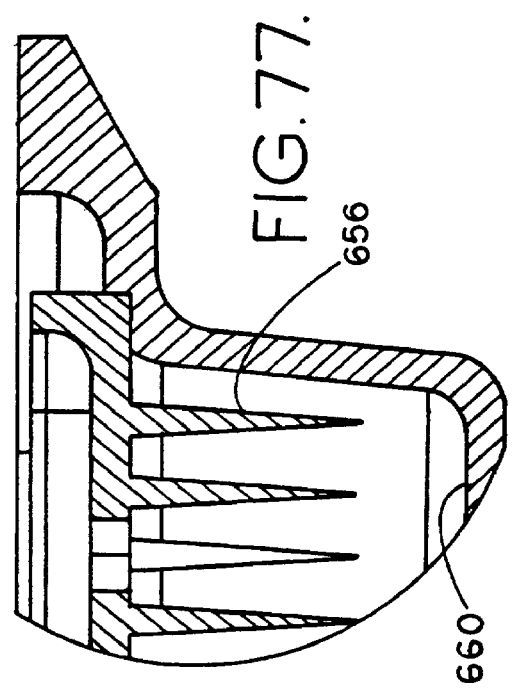

APPARATUS AND METHOD FOR HARVESTING AND HANDLING TISSUE SAMPLES FOR BIOPSY ANALYSIS

CROSS REFERENCE TO RELATED APPLICATION

The instant application is a continuation-in-part of application Ser. No. 08/645,750, filed on May 14, 1996, and presently pending. All of the material of this application is incorporated by reference into the present application.

TECHNICAL FIELD OF THE INVENTION

The present invention relates to the general art of analysis of tissue samples, and to the particular field of obtaining, handling and processing tissue biopsy samples.

BACKGROUND OF THE INVENTION

When disease is suspected in a living being, the physician must arrive at a specific diagnosis. Some disease processes, particularly tumors, require a histologic and/or cytologic diagnosis. While radiologic tools are useful in detecting the presence of a tumor, the cell type of the tumor can only be determined by a pathologist's examination of a histologic or cytologic sample of the tumor. There are a number of devices that have been fashioned to actually perform the act of taking tissue samples. These devices may obtain tissue for histology or in the case of needle aspiration biopsies, samples for cytology and histology. In many cases, these samples are very small and difficult to retrieve and process. These small tissue fragments may originate from a punch, or similar biopsy procedure devices or from Fine Needle Aspiration Biopsy (FNAB) biopsies. FNAB is typical and produces single cells, small cell clumps and fragments which are immediately smeared onto a glass slide (direct smears) or rinsed into a container with preservative fluid. After being transported to the laboratory, these samples are centrifuged onto a glass slide (cytospin smears). In some cases needle aspiration biopsy produces tissue fragments which are large enough to process histologically. If successfully retrieved, these fragments are submitted in blood clot or agar in a technique known as cell block preparation which are then immobilized in wax for sectioning and slide preparation.

FNAB is one example of the tissue collection techniques used and the problems which are of interest to the present invention. Fine Needle Aspiration Biopsy techniques have been practiced for many years and the literature contains many studies on technique and comparison of various improved devices for same. There exists two different kinds of biopsy needles. Those with active or movable cutting elements and those that are passive or non-moving. Active needles have two basic problems, which are cost and complexity. The needles that are of interest to this invention are most often 22 gauge which is 0.028" OD with a standard wall of 0.006". This leaves only 0.016" ID. Some prior art designs use an active element down the ID bore to sever and capture tissue. 0.016" does not provide a great deal of clearance for these elements and thus these prior art needles are inefficient. If it is desired to further suck tissue fragments up the needle bore further reducing the bore, the bore will be further reduced because a second element must be added, which is counter productive.

Other methods of obtaining samples are also discussed in the literature and also have problems. Each is characterized by tissue size and number of pieces generally available as well as whether orientation in the eventual sectioning plane is critical for example:

Fine Needle Aspiration Biopsy—very small pieces of tissue taken from the core of a fine needle; usually transported in fixative solution;

GI biopsy—characterized by a few small tissue pieces; it is desirable to concentrate the tissue pieces in close proximity to each other;

Prostate chips—orientation is irrelevant for these samples;

Endometrial Curettings—characterized by varying size samples; orientation is irrelevant;

Vessel—orientation is critical; sections need to be transverse;

Core Biopsy—i.e. from the prostate—orientation is critical; the tissue should lie flat all in the same plane;

Gall bladder—orientation is critical—the tissue should be embedded on edge;

Uterine Wall, breast or large tumors—orientation is not critical—sample lies flat in a plane.

Some of these methods are characterized by the possibility of supplying extremely small tissue samples. Some samples can be as small as a few cells, and extremely small samples can create problems. These problems include loss of the sample, dehydration of the sample, and contamination of the sample during harvesting, storage and transport. Still further, as will be more evident from the following discussion, small samples are extremely difficult and time consuming to process in the laboratory.

Still further, in many cases, a tissue sample is mixed with effluent. Prior art devices and methods account for collection of effluent only and do not provide devices and methods for trapping tissue specimens. The prior art collects effluent, but does not provide devices or methods for the separation of tissue from the effluent. Therefore, there is a need for apparatus and a method for handling effluent as well as tissue samples and for efficiently separating tissue from effluent.

Once a tissue sample is harvested it must be transported to the pathology lab for processing. Currently, handling and processing of small biopsies in the histology laboratory is a tedious task and requires multiple manual manipulations of the specimen. Fine Needle Aspiration Biopsy (FNAB) is typical. Therefore, there is a need to handle and process very small samples of tissue in an expeditious manner.

In addition to the above problems, a further problem with currently used apparatus and methods is associated with the orientation of samples. Currently, in a pathology lab, the pathologist will gross-in the tissue samples, cut them into appropriate size specimens, if necessary, and place them into a tissue cassette for processing. Herein lies one of the biggest problems of the existing art. When the tissue sample is placed into the tissue cassette, the pathologist orients the sample so that any surface in which he or she desires to see sectioned is placed face up in the cassette. The histotech who retrieves the tissue from the cassette after processing knows through training that when opening the cassette the tissue surface that faces up when first opened is then placed face down into the wax mold, which in turn will become the first surface to be sectioned by a microtome blade. This is an established protocol which is observed in most pathology labs today. This process then necessitates human involvement and redundant handling. In addition, sometimes special sponge materials must be packed into the cassette to keep a sample oriented or to prevent loss from the cassette if it is too small and may turn or lose its orientation during the tissue processing. Sometimes, notes and drawings accompany tissue samples to show how they should be oriented in the wax.

No current system or method provides the ability to maintain critical tissue orientation throughout these steps and eliminate human errors in the associated manual steps and procedures. Therefore, there is a need for a system and a process that can maintain the preferred orientation of the tissue sample from the time of initial gross-in throughout the tissue processing procedure and continuing through the wax embedding stage with no human involvement required beyond initial gross in.

Yet another problem associated with harvesting and handling of tissue samples for biopsy analysis is associated with the analysis process itself. In the analysis procedure, the sample is exposed to heat and chemicals which can cause the tissue and/or its support to change shape and/or move. The sample-holding structure should account for this or there may be a risk of damaging the sample or the sample holder. Accordingly, there is a need for an apparatus for holding a harvested biopsy sample in a manner that accommodates the tissue analysis process.

Another problem encountered with presently available systems is the lack of integration and multiple handling steps required to produce a sectioned sample for pathological examination. Therefore, there is a need for an approach which reduces the time and handling of biopsy samples.

By way of background, a review of the standard procedure that each sample must undergo to get from harvest to a prepared histologic slide is necessary. First, the sample must be taken with the appropriate instrument. The tissue is then retrieved from the instrument and deposited into some sort of specimen container, usually with a fixative such as 10% formalin. The container is labeled and transported to the pathology lab. Herein lies the first problem with the prior art. With no way to control where the sample lodges in the container, the sample may stick to the lid or sides of the container and become dried out before it reaches the pathology lab; rendering it difficult, if not impossible to interpret. In addition, the samples may be extremely small and may be hard to locate and retrieve from the container.

When the pathology laboratory receives the container, the specimen is logged into the manual or computerized anatomic pathology system and is assigned a unique surgical pathology accession number. This number is placed on the specimen container and is subsequently used to label histology slides, cassettes and the final surgical pathology report. The specimen is logged into the paperwork system and physically described in an appropriate medium, such as dictation or the like, by a pathologist or assistant. This is the description portion of the process known as "grossing-in" the specimen. The grossing in continues when the pathologist or assistant manually retrieves the specimen and views the specimen, and then sections the specimen into appropriate size morsels, if necessary, and places them into a plastic tissue cassette. If very tiny or multiple, the pieces of tissue must be immobilized within some device such as two layers of sponge or a tea bag to prevent them from escaping from the cassette during processing. Many times a surgeon will have taken diffuse biopsy samples or scrapings from the mucosal lining of an organ, such as an endocervical biopsy. Often these samples are very small and multiple such as is the case with tissue fragments from Fine Needle Aspiration Biopsy (FNAB). Other times a doctor will deposit the sample in filter paper which resembles a tea bag. All of these various tissue specimens end up in a tissue cassette. As used herein, the term "grossing-in" includes both the description of the tissue sample and the preparation of the tissue sample for further processing.

At the end of the day all of the cassettes are put into a tissue processor where the tissue is subjected to a sequence of solutions and heat. These solutions gradually replace water in the cells with alcohol, followed by xylene, and ultimately by wax. This gives the wax-impregnated tissue a similar consistency to the wax surrounding the tissue in the next step. After the tissue processing is complete, usually the following morning, the sample is again handled to remove it from the cassette where it is placed and oriented in a mold. At this point if a tea bag or sponge was used to immobilize the sample, the pathology lab is then faced with trying to extract or scrape the wax-impregnated specimen from the paper, before placing the specimen in the wax mold.

An embedding medium such as hot (molten) paraffin wax is poured into the mold to immobilize the tissue in a solid block of wax. Wax or parrifin can be used as an embedding medium; however, agar or even chemically setting resins such as polyester can be used. Harder resins can also be sectioned with a saw blade and then ground and polished to a thin film. After cooling, the wax block is removed from the mold, placed into a microtome and sectioned into thin slices approximately 4-6 microns thick. These sections are floated onto glass slides, stained, cover-slipped, and are then ready for microscopic examination. In this process, samples are handled or transferred many times. Each handling process takes time and human involvement.

Therefore, there is a need for apparatus and method to improve the harvesting of tissue samples. There is also a need for handling and processing those harvested tissue samples in an efficient and reliable manner that lends itself to automation and removes the need for a human to find, handle and orient a tissue sample before analysis of that sample can be performed.

Some long thin tissue samples are difficult to align and orient. The parent application discloses walls and pegs between which tissue is placed.

While in many instances those configurations work well, such as for fallopian tubes, in other instances, such as for gallbladder, it is difficult to place the tissue between the posts. Most often because the tissue sample varies in dimension from one end to the other. It is difficult to accommodate the many different sizes of tissue that are encountered in preparing biopsy samples. Therefore, there is a need for an orientation device which can be self accommodating to the differing dimensions of tissue samples. In addition, it is much easier to hold the tissue upright and place the orienting device over the tissue.

Once the tissue is properly supported by the orientation device, the device and the tissue are both subjected to the analysis process. Therefore, in addition to being easy to use in connection with biopsy samples, the orientation device must be able to withstand the analysis process and be sectionable as well.

OBJECTS OF THE INVENTION

It is a main object of the present invention to provide apparatus and method for handling harvested tissue samples in an efficient manner which lends itself to automation.

It is another object of the present invention to provide a system and a process that can maintain the preferred orientation of the tissue sample from the time of initial gross-in throughout the tissue processing procedure and continuing through the wax embedding stage with no human involvement required beyond initial gross-in.

It is another object of the present invention to provide apparatus and a method for efficiently harvesting tissue samples for biopsy.

It is another object of the present invention to provide apparatus and method for handling harvested tissue samples in an efficient manner with a minimum of human intervention.

It is another object of the present invention to provide a tissue trap and support that can retain tissue samples and facilitate easy transfer of the specimen without having to individually retrieve small tissue fragments from a sample container.

It is another object of the present invention to provide a tissue trap or stage that is sectionable and that is constructed of a material that is able to be sectioned in a microtome and appears non-distracting in the histologic sections and does not stain with tissue stains applied to the sections.

It is another object of the present invention to provide a tissue trapping platform that is constructed of a material that is impervious to the harsh chemical and temperature environment of a tissue wax processor machine.

It is another object of the present invention to provide a tissue trapping platform that is constructed of a material that is impervious to the chemical and temperature environment of a tissue wax embedding machine and may have a surface modification improving wettability on the filter or stage of the platform. The stages may be sectionable or not.

It is another object of the present invention to provide a biopsy container that holds the specimen sectionable trap for easy placement of tissue samples, and assures that the tissue remains continually submerged in the fixative solution and further allows the removal of the tissue trap and support and specimen with ease.

It is another object of the present invention to provide a method for immobilizing the tissue on a trapping platform to facilitate automation of the embedding medium process.

It is another object of the present invention to provide a method of automating the cell block tissue preparation, processing and wax embedding procedures.

It is another object of the present invention to provide for a tissue trapping platform which includes some sectionable tissue management features.

It is another object of the present invention to provide a tissue trapping platform which includes a method of assuring that the tissue will be oriented in the desired sectioning plane in the embedding media and will be pressed down into the wax embedding material so as to be close to the sectioning surface.

It is another object of the present invention is to automate the front end of a biopsy sample analysis procedure by providing a method to place the harvested tissue appropriately onto the sectionable filter or stage or on a non-sectionable stage prior to tissue processing.

It is another object of the present invention to automate the paraffin embedding process once the tissue has passed through the processor.

It is another object of the present invention to provide a method for automating the gross in process.

It is another object of the present invention to provide a fine needle aspiration biopsy device which includes a detachable tissue trapping sectionable support means specifically adapted for the needs of specimen processing in pathology.

It is another object of the present invention to provide a surgical biopsy device which includes a detachable tissue trapping microtome-sectionable support specifically adapted for the needs of specimen processing in pathology.

It is another object of the present invention to provide a cassette that traps tissue and maintains a stable orientation and spacing between samples through tissue processing and embedding procedures.

It is another object of the present invention to provide a system that accommodates dimensional changes of the cassette during processing.

It is another object of the present invention to provide a cassette system that allows the cassette to be securely retained in the frame during processing, yet allows for easy release of the cassette when desired.

It is another object of the present invention to provide a cassette system having a lid that can securely retain various sizes of tissue.

It is another object of the present invention to provide a cassette system having a lid that is hingeably connected to the cassette and can accommodate and hold different tissue sizes in the cassette.

It is another object of the present invention to provide a cassette that permits material held therein to be sectioned.

It is another object of the present invention to provide a cassette system that is not likely to become separated during handling.

It is another object of the present invention to provide a cassette system that is highly resistant to chemical solvent effects that are encountered during processing.

It is another object of the present invention to provide a small cassette which can yield a large number of tissue slices on a slide.

It is another object of the present invention to provide a cassette system that retains tissue in a single plane while accommodating tissue of various thicknesses within the same cassette well.

It is another object of the present invention to provide a cassette system that has a special device which can be installed on tissue samples and which maintains their orientation during processing.

It is another object of the present invention to provide a cassette system that can accommodate tissues having various sizes.

It is another object of the present invention to maintain orientation of a tissue sample and accommodates various tissue sizes which can be embedded and sectioned.

It is another object of the present invention to provide a cassette system that has a tissue trap where the tissue is not removed from the cassette after processiing.

It is a more spectific object of the present invention to provide a cassette system that is made more sectionable during the analysis process.

SUMMARY OF THE INVENTION

These, and other, objects are achieved by providing a multipurpose tissue trap and support. The tissue trap is formed so it can be cleanly sectioned using a microtome and which is constructed to survive the harsh chemical environment of the tissue preparation process and to be visually non-apparent when viewed during microscopic examination of the tissue structure during tissue analysis. For the purposes of this disclosure, a platform assembly includes a cassette frame and either a sectionable immobilizing platform or a non-sectionable immobilizing platform. By "sectionable," this disclosure means sectionable in a microtome. The cassette frame is adapted to accept stages or platforms with movable features and is adapted for us in a microtome.

Thuse a tissue suport may be used in conjunction with a cassette frame, a platform and a cassette, and may be used to capture tissue samples and to keep them in good condition during transportation to the pathology lab and to manage the tissue specimen during the preparation, wax medium embedding and sectioning of the tissue.

The tissue trap can be used in or in close association with the harvesting apparatus, such as a Fine Needle Aspiration Device, or the like, and will support the harvested tissue in a manner that promotes automation of the handling process, even if the samples are extremely small.

Broadly, the invention includes a tissue trap and support that can include a porous member. For ease of discussion, this porous member will often be referred to as being a filter because it traps certain material (tissue) while permitting liquid to pass through it. The main purpose of the filter is to trap and hold material, such as harvested tissue samples. The filter is formed so that the tissue samples received directly from harvesting techniques can be placed directly onto the filter and can remain on that filter throughout the entire process, including microtome sectioning and mounting on a slide for analysis. The filter is microtomable, that is, it can be cleanly sectioned in a mictrotome. In this manner, the handling of the tissue samples can be entirely carried out in an automated manner because the tissue sample does not have to be handled.

More specifically, the invention includes various sectionable cassettes also referred to herein as tissue trapping platforms, that reduce the amount of sample handling required by either the pathologist or technician and make possible an automated system. A sectionable cassette includes a filter or stage in a cassette frame. The tissue trapping platforms can have a movable sample surface. The movable sample surface facilitates sample loading, confers protection from crushing of the tissue samples during the processing steps and allows the sample surface to be pushed into the wax mold for embedding.

By being placed inside the cassette, tissue is trapped and cannot be cross-contaminated with another sample. Therefore, the cassette is in a configuration with a bottom and four sides and a hinged lid. The cassette is placed into a frame, which holds the cassette during the tissue processing procedure. The frame also carries the sample identification surface on it. Many different types of sectionable cassettes can be interchangeably installed in the frame. It therefore could be characterized as being a "universal frame." One of the key components to making this system work is to be able to support the cassette properly during the tissue processing procedure. The tissue processing chemistry and heat make the sectional cassette very soft and in addition sometimes makes the cassette swell. Therefore in order to avoid distortion of the cassette, the cassette must be properly supported during processing. In addition, it must be very easy for the histotech to install the cassette into the frame.

One of the sectionable cassettes described in this disclosure contains a sectionable immobilization stage which enables the pathologist or technician to orient and fix tissue samples such as gall bladder, prostate chips or transverse vessel samples. The term "sectionable" as used herein means the item can be cleanly sectioned into extremely thin sections using a microtome to cut the embedding medium, tissue sample and any sectionable platform, so the layers can be mounted on a slide for further analysis. The tissue sample can be stretched or "pinned" into an appropriate orientation to provide for the proper plane of sectioning. This orientation process can take place at initial gross in and only has to be done one time to ensure appropriate positioning for sectioning. The prior art requires handling of the samples before processing and then orienting of the samples after tissue processing. The design of the sectionable immobilization stage and cassette frame combination allows for the vertical translation of the sample surface, so the samples can be automatically pressed down into the wax mold base and positioned close to the sectioning surface of the wax.

Another type of sectionable cassette contains a sectionable filter design which can be used to collect biopsy samples from various biopsy containers or devices. These sectionable filters are device specific. One such filter has particular application to the handling of Fine Needle Aspiration Biopsy samples. This filter can be manufactured in various pore sizes. One application for this filter is to include it with a biopsy sample container. The trapping filter is detachably retained on the cap of the container and can be removed with a single-handed motion. It is intended that the filter be placed directly into the cassette frame thereby eliminating the step of retrieving the samples from the sample container. In addition, this particular filter is constructed in such a way as to allow the filter to remain in the cassette frame while it is in the tissue processor. An immobilization technique which permanently affixes the tissue to the stage, filter or platform could be used with this type of filter prior to tissue processing. The filter when removed from the cassette frame can also be placed directly into the mold for paraffin block preparation without further manipulation since it can be successfully sectioned once embedded in the wax.

When biopsy samples are small (1 mm$^3$ or less) it can be hard to locate and position a sample properly in the wax mold and this handling can be time consuming. By retaining the samples on the sectionable filter from initial collection to the final embedding procedure these problems are avoided.

Another type of sectionable cassette, also referred to as the sectionable filter cassette, is designed as a screen in a cassette frame with a vertically translatable sample surface. This type of sectionable cassette might be coupled with an immobilization technique and then would allow for the automatic gross-in of Fine Needle Aspiration Biopsy samples as well as mucosal scrapings, endometrial curettes, GI biopsies scrapings, etc. This sectionable filter cassette could be manufactured in different pore sizes to accommodate different applications.

A fourth type of sectionable cassette contains a non-sectionable stage which can accommodate large pieces of tissue which do not change orientation during processing just because of their size. These samples also protrude far enough off the surface of the stage so that once embedded in wax, enough sample is available in the microtomed sections so that the non-sectionable stage itself never interferes with the microtome blade.

The non-sectionable cassette with its movable sample surface can remain in a cassette frame through tissue processing, wax embedding and microtome sectioning.

The invention includes apparatus to immobilize the tissue samples on a filter or stage to reduce the number of manipulations required and to enable the automation of the whole histologic section preparation process. The immobilization technique does not alter the tissue composition in any way, nor does it interfere with the normal interactions of the tissue and the processor and wax embedder as well as the appearance of the final section and can be efficiently used on long, thin samples. Immobilization techniques, from the very simple to more complex are disclosed hereinafter.

In addition, one element of the present invention provides a novel tissue separation system and allows for the recovery of tissue samples from the effluent in a surgical suction device. The combined features of this invention reduces the transfer and handling requirements of the samples throughout the entire process.

Additionally, there is provided elements to immobilize the tissue on a platform which can then be passed through the tissue processor and wax embedder. The prior art requires the histotech-nologist to spend a major proportion of a work day removing tissue from cassettes after processing and orienting them in the wax mold. The present invention discloses a novel method for eliminating these steps by automating this process.

The present invention provides a reduction in handling by immobilizing the tissue onto or along with a sectionable cassette that can travel through the entire tissue preparation and mounting process. The immobilization can be mechanical whereby the tissue is hooked or pinned or otherwise mechanically bound to the platform. Alternatively, the immobilization can take on a much more active roll such as adhesives, coatings, gels or covering materials. The immobilization also permits automation of the entire process. By fixing the tissue to a sectionable cassette that can be machine manipulated, the tissue can be moved and oriented through use of machine components that would otherwise crush or be unable to manipulate tissue samples. By further making the sectionable cassettes of the sectionable cassettes a material that can be embedded in the final wax process with no ill effects on the sectioning process or to the diagnostic pathological review of the stained tissue, the cycle can be completed with labor savings and accuracy of tissue specimen preparation.

Automation of the histologic section preparation process is a significant way of consolidating manpower requirements in the histology laboratory. In today's hospitals there are consolidation efforts underway to reduce or combine services of area health care providers. In addition, mergers and takeovers have forced some histology labs to go to extreme measures to keep up with the demand for processed and sectioned histologic slides. In the prior art, one of the most time-consuming tasks in the laboratory is the manual handling of biopsy samples. By reducing the handling requirements and redundant steps significant reductions in labor-related costs can be achieved with this invention. The present invention includes apparatus and methods to manually load or automatically dispense specimens, automatically gross in specimens, automatically immobilize specimens and automatically wax embed specimens. Use of any of these automated procedures substantially improves the work flow in the histology laboratory and potentially provides the pathologists with their sections for review in a more timely and efficient manner.

The sectionable cassettes of the present invention provide a surface to which the tissue will become attached at or before gross-in. Elements are disclosed for immobilizing the tissue sample to the filter or stage of the sectionable cassette prior to introducing it into the processor. The tissue remains attached to the cassette through the tissue processor without effect on the tissue or processor. This further allows that once through the processor the cassette and tissue could be handled by mechanical apparatus through the wax embedding procedure and does not necessar-ily require further manipulation by a technician.

A description of the process with the biopsy container system with integral sectionable filter will now be presented. The tissue is placed or deposited on the sectionable filter at the time of harvest in the surgical setting. The sectionable filter and tissue are then immersed in a fixative solution for transport to the pathology lab. Once in the lab the pathologist or clinician removes the sectionable filter from the container. The tissue is trapped on the sectionable filter so there is no need to probe around inside the container looking for tissue particles. The sectionable filter and specimen are grossed in (described for record) and placed in a filter cassette frame. If necessary, at this point a tissue immobilization technique can be applied in order to affix the tissue to the sectionable filter.

The sectionable filter is constructed to survive the harsh chemical environment of the processor. After the cassette has emerged from the processor, the sectionable filter/specimen is placed in the embedding mold, tissue side down. Since the sectionable filter of the present invention has been specially formulated from a material that allows it to be sectioned in the microtome, the sectionable filter itself becomes embedded in the wax along with the tissue specimen. This eliminates the further step of finding and individually placing each tissue fragment in the embedding waxing mold. After the sectionable filter is placed in the mold, the mold is filled with molten paraffin. When chilled, the paraffin with embedded specimen and sectionable filter (paraffin block) is removed from the mold and is ready for sectioning to make histologic slides. Again, the term "wax medium" is used to describe one form of embedding medium. This is not intended to be limiting since one skilled in the art could use other embedding media based on the teaching of the present disclosure.

Still further, because the filter eliminates the need to manually handle a tissue sample, the automated process could also include an automated gross-in station. In some cases where specific tissue orientation is not critical, an additional automated step can empty the contents of a biopsy container onto a sectionable platform, depositing the larger samples on the filter surface of the platform. This is applicable to samples from Fine Needle Aspiration Biopsy and GI biopsies, in particular. Upon arrival at the histology lab the sample containers are placed into the automated gross-in station where the machine removes the lid of the container and decants the fluid containing the samples onto a sectionable filter cassette (assuming a sectionable filter does not come with the container as disclosed herein). This process will work well for samples such as GI biopsy that do not need to be oriented in any special way for the section.

A surgical pathology accession number, unique to each specimen, is obtained when the specimen is accessioned into the laboratory's anatomic pathology computer system. A barcode can be generated at this time and placed on the specimen container thus uniquely identifying the specimen with its accession number. By interfacing an automated computer system, the surgical pathology accession number can be printed on each specimen cassette and video image. The number can be human readable and/or computer readable. The samples that are trapped on the sectionable filter are then recorded with a single digital image or infrared or other scan which could have a 1 mm (or other scale) reticule grid in front of the lens to aid in sizing the tissue pieces. The image, surgical accession number, date and other pertinent information are stored on a write optical computer drive or other magnetic media for archive purposes. Once scanned, the platform with sample is fed into the immobilization device.

Currently, state-of-the art preparation of tissue samples for microscopic examiination is a very labor-intensive and sequential-step dependent process. While this current process works well, it is merely the result of a combination of very old non-integrated processes, which have evolved into standard practice. Small improvements have been made over the last twenty years in such areas as tissue processing machines (e.g., vacuum infiltration) and automated (e.g., computerized) record keeping. However, very little has been done to integrate and reduce the steps that are required from the time the tissue is harvested to the final preparation of a diagnostic slide. Within the present disclosure the inventors have disclosed a cradel-to-grave system in which all components are designed to eliminate steps and to provide the users with a fully integrated system that will provide for a more efficient overall process.

In today's lab, tissue samples are handled numerous times before a final slide can be prepared. This constant involvement of the human hand is inefficient and costly. In addition, the current healthcare environment has created enormous incentives to cut costs. For many pathology labs this has meant a consolodation of smaller lab facilities that are now shared between hospitals. This then creates larger central facilities that must process enormous quantities of tissue samples all the while demanding higher efficiencies from employees. There has been a long-felt, and heretofore unfufilled, need for a less labor intensive process.

The inventive system disclosed herein has been designed to move the biopsy samples with the least amount of operator involvement, while maintaining at least the current standards for preparing slides. For instance, numerous methods are disclosed which take advantage of the invention's ability to capture tissue samples at the site of harvest, thus eliminating the steps of transferring the samples form one container to another. The inventive material goes on to encompass the entire record keeping, tissue processing and wax embedding procedures. Therefore, a larger number of samples can be processed by a fewer number of individuals. This is accomplished by utilizing the inventive tissue handling components, combined with automated machinery to transport tissue samples through the various stages creating a final slide for pathological examination.

BRIEF DESCRIPTION OF THE DRAWING FIGURES

FIG. 1 is a filter cassette or stage.
FIG. 2 is another form of filter cassette or stage.
FIG. 3 is a tissue sample mount.
FIG. 4 is a sectionable immobilization stage.
FIG. 5 is a sectionable immobilization stage assembled in a stage cassette frame.
FIG. 6 is a non-sectionable stage with biopsy samples thereon.
FIG. 7 is a non-sectionable stage in a wax mold cavity.
FIG. 8 shows the steps in an automated process of handling tissue samples according to the present invention.
FIG. 9 is a filter stage with a processing number thereon.
FIG. 10 is an automated machine for processing tissue samples from gross-in to final slide preparation.
FIG. 11 illustrates the processing of an immobilizing platform.
FIG. 12 shows a stage in a wax molding machine.
FIG. 13 shows tissue immobilized on a platform.
FIG. 14 shows the immobilized tissue being placed in a mold for the wax process.
FIG. 15 shows a cassette with a processing number thereon.
FIG. 16 shows steps in the operating sequence for a pair of mold bases.
FIG. 17 shows a tissue immobilizing step.
FIG. 18 shows the tissue immobilizing step of FIG. 17 with immobilizing elements in place.
FIG. 19 shows a container having a filter.
FIG. 20 is an exploded perspective view of the container shown in FIG. 19.
FIG. 21 illustrates the use of a tissue sample container.
FIG. 22 illustrates another step in the use of the tissue sample container.
FIG. 23 shows a tissue collection device.
FIG. 24 shows a tissue collection device.
FIG. 25 shows a Fine Needle Aspiration device.
FIG. 26 shows a prior art needle.
FIG. 27 shows a needle embodying the present invention.
FIG. 28 shows the prior art needle removing a tissue sample.
FIG. 29 shows the needle of the present invention.
FIG. 30 is a view taken along line 30—30 of FIG. 29.
FIG. 31 shows a needle using the teaching of the present invention.
FIG. 31A shows a prior art needle.
FIG. 32 shows a needle using the teaching of the present invention.
FIG. 33 shows another view of the needle in FIG. 32.
FIG. 34 shows a tissue harvesting step in the process of the present invention.
FIG. 35 shows a step of storing a harvested tissue sample in a container.
FIG. 36 shows another step of storing a harvested sample.
FIG. 37 shows a step in the process of storing and handling a harvested sample.
FIG. 38 is a flow chart showing the process of harvesting and handling a tissue sample according to the teaching of the present invention.
FIG. 39 is a perspective view of a laboratory device using the sectionable filter of the present invention.
FIG. 40 is a sectional view of the laboratory device shown in FIG. 39.
FIG. 41 shows a tissue support and tissue embedded in a final assembly.
FIG. 42 shows a platform, such as shown in FIG. 3, embedded in wax.
FIG. 43 shows a microtome device slicing a wax embedded specimen and tissue support.
FIG. 44 shows another view of the microtome slicing a wax embedded specimen and tissue support.
FIG. 45 shows a slide mounted tissue/tissue support/wax which have all been sliced in a microtome.
FIG. 46 shows a slide mounted tissue/tissue suppor/wax which have all been sliced in a microtome.
FIG. 47 is a perspective view of a tissue biopsy sample holding unit.
FIG. 48 is a detail of FIG. 47.
FIG. 49 is a top plan view of the holding unit.
FIG. 50 is an end view of the holding unit.
FIG. 51 is a section view of FIG. 49.
FIG. 52 is a detail view of FIG. 49.
FIG. 53 is a detail view of FIG. 50.
FIG. 54 is a detail view of FIG. 49.
FIG. 55 is a top plan view of a cassette of the present invention.
FIG. 56 is a side elevational view of the cassette shown in FIG. 55.
FIG. 57 is an end elevational view of the cassette shown in FIG. 55.
FIG. 58 is a side elevational view of a cassette.
FIG. 59 is a detail view of FIG. 58.

FIG. 60 is an end elevational view of the cassette shown in FIG. 58.

FIG. 64 is a top plan view of a cassette.

FIG. 65 is a detail view of FIG. 64.

FIG. 66 is a sectional view taken of FIG. 64.

FIG. 76 is a side elevational view of the cassette shown in FIG. 74.

FIG. 77 is a detail of FIG. 76.

FIG. 78b is an side elevational view of the tissue orientation device shown in FIG. 78a.

FIG. 78c is a bottom plan view of the tissue orientation device shown in FIG. 78a.

FIG. 78d is an end elevational view of the tissue orientation device shown in FIG. 78a.

FIG. 79 is a perspective view of the tissue orientation device shown in FIG. 78a.

FIG. 80 illustrates the use of the tissue orientation device shown in FIG. 78a.

DETAILED DESCRIPTION OF THE PREFERRED EMBODIMENT OF THE INVENTION

Tissue Trapping Platforms

Figure 1:
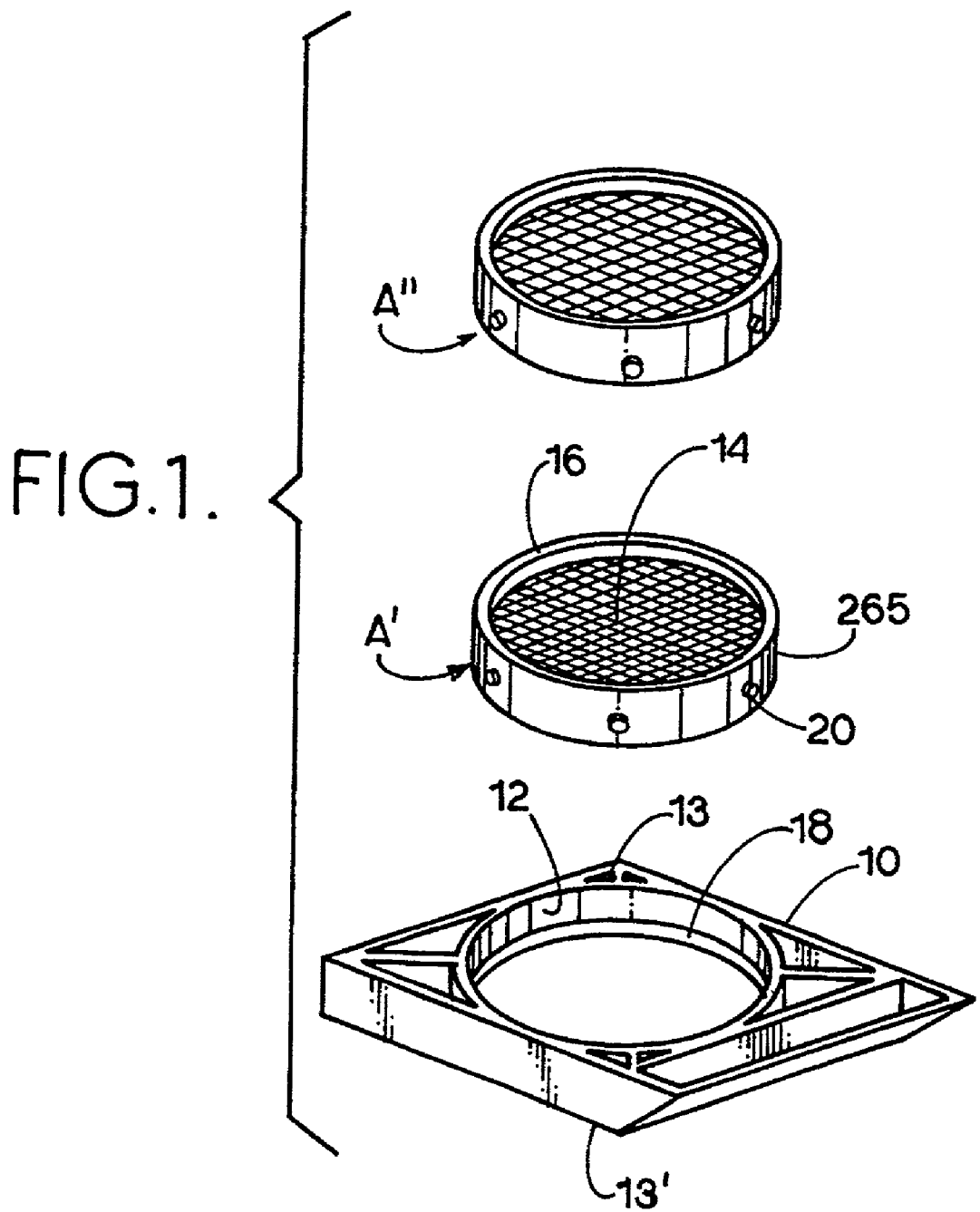
Figure 2:
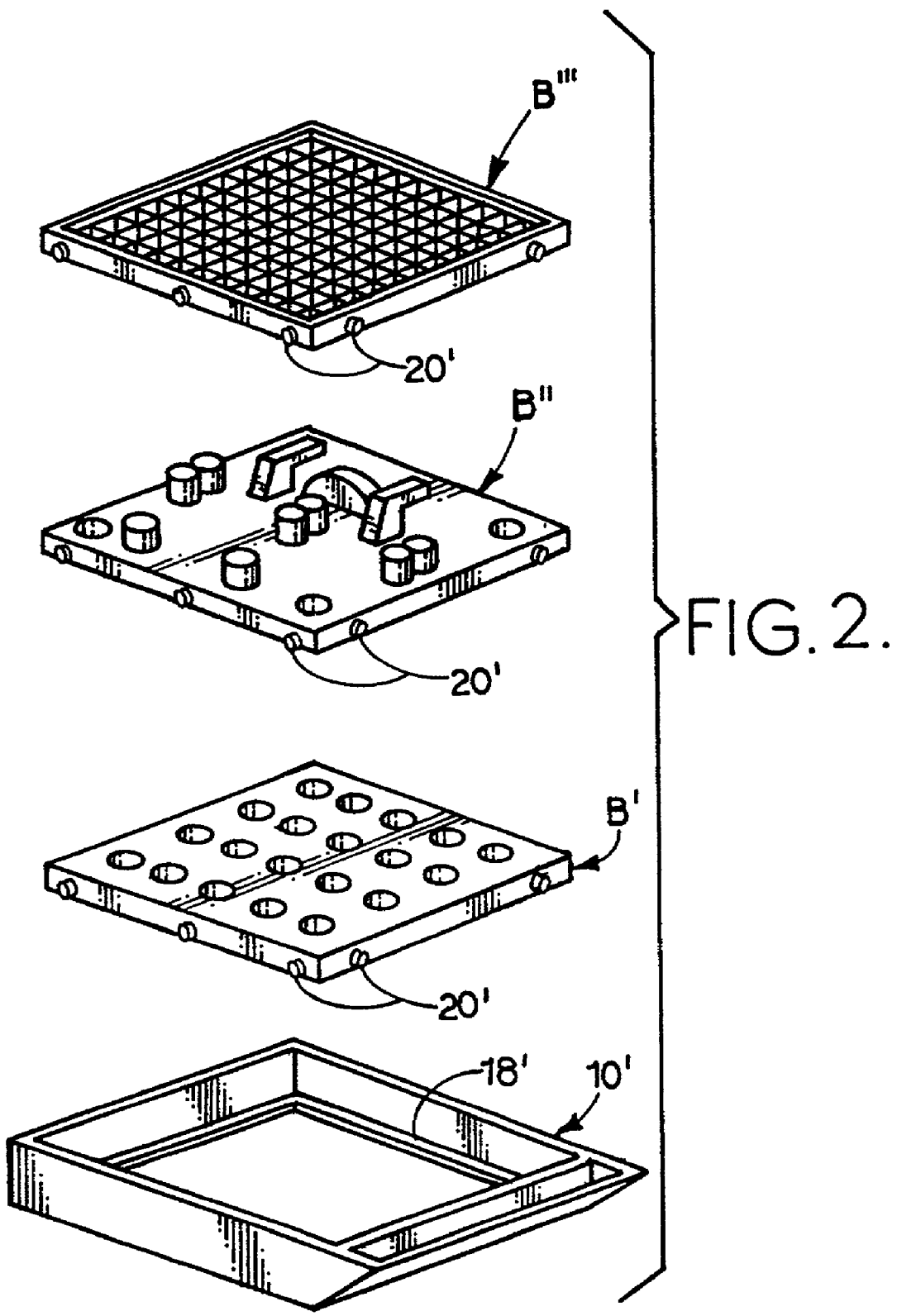

A platform includes a filter or stage assembled in a filter cassette frame or a stage cassette frame. FIGS. 1 and 2 show platform assemblies with interchangeable microtome sectionable tissue trapping filters, sectionable immobilizing stages or non-sectionable immobilizing stages and cassette frames.

Microtome Sectionable Tissue Support

FIG. 1 shows a cassette frame 10 with a cylindrical interior frame 12 which is designed to accept microtome sectionable tissue support, such as filters A' and A" each of which can be porous and forms a tissue support 14 surrounded by a collar 16. As discussed above, the term "filter" will be used for the tissue support because, in one form of the tissue support, fluid can pass through the tissue support while tissue samples are retained on the support in the manner of a filter. Tissue support 14 supports tissue samples during tissue processing, embedding and microtomy and can include sectionable filters which can be located in surgical biopsy instruments, biopsy containers, or the like, and can be integral with the instrument or container, or could be used in an automated biopsy sample dispensing system, with effluent passing therethrough as will be understood from the ensuing discussion. The biopsy sample support further includes a collar 205 surrounding the tissue support, and elements such as projections 20 on the collar, for connecting the tissue support to the frame 10 via grooves 18. The shape of the tissue support is shown as circular, but could be other shapes as well without departing from the scope of the present disclosure. Filter A' or A" is movable with respect to the frame 10 and has elements for moving the filter element into multiple positions relative to the frame, with these elements including filter detent grooves 18 internal to the interior frame 12 and projections 20 on collar 16 which mate with the grooves and which extend radially outward from the periphery of the sectionable filters. There can be several grooves which are spaced apart from each other in the frame along the longitudinal dimension of the frame. Projections 20 can be moved from one groove to another to allow the sectionable filter, and more specifically the sample surface, to be movable and to be positioned at various heights with respect to the cassette frame ends 13 and 13'. As will be understood from the teaching of this disclosure, the various heights allow access to the sample surface of the sectionable filter for more convenient loading and also offer protection from abrasion or dislocation of the tissue on the sample surface during tissue processing. The translatable height feature of the cassette frame also allows the sample surface of the filter to be positioned deep into the mold cavity for wax embedding.

Sectionable filter A' shows a fine ¼ mm filter grid and sectionable filter A" shows a 1 mm filter grid. Preferred pore sizes are 1 mm, ¼ mm and 180 microns to 200 microns for use with FNAB. However, other pore sizes can be used based on the teaching of the present disclosure as will occur to those skilled in the art. The sectionable filter grid can be manufactured in many other sizes as will be understood by those skilled in the art based on the teaching of this disclosure.

In general, the filter is one form of a tissue support used in an overall apparatus for supporting histologic tissue biopsy samples. In general, the overall apparatus comprises a microtome sectionable tissue support such as filters A' and A" for supporting tissue samples during tissue processing, embedding and microtomy including a means for permitting the tissue supporting means to be successfully sectioned in a microtome. Successful microtome sectioning means, as used herein, sliced in a microtome without damaging the microtome or the tissue, or without tearing or cleaving the tissue or the tissue support. The tissue supporting means includes a means for resisting histological stains, a means for resisting degradation from solvents and chemicals used to fix, process and stain the tissue and a means for maintaining the tissue support, also referred to herein as tissue supporting means, non-distracting during tissue processing and slide preparation. As used herein, the term "degradation" is defined to mean softening, discoloring or any kind of unfitness for use in all processes associated with the analysis of the tissue.

The sectionable filter or stage is made from a special low density thermoplastic which is molded into a porous filter or screen. The filter is specially selected to resist the chemical and heat environments in the tissue preparation processor. At the same time the material must be of similar density to both the tissue and the paraffin embedding materials. It must further be able to be sectioned using a standard laboratory microtome (microtomy) without dulling or nicking the blade. The material must section just as if it were part of the wax without tearing or cleaving. If the filter material tears during microtome sectioning, it may destroy the fragile tissue section. The material must also not stain when the tissue is prepared with various histologic stains. It should not become soft, discolored or dissolved in the solvents and chemicals used to stain the tissue. Still further the material must appear non-distracting, such as window clear, in the section so as not to distract or confuse the pathologist during microscopic examination. As used herein, the term "non-distracting" means that the material will be readily identifiable as being filter material as opposed to tissue when viewed during analysis of the tissue specimen. Thus, a "non-distracting" material will not be confused with tissue being analyzed during tissue analysis. The preferred form of a non-distracting material appears window clear or at least translucent when viewed during tissue analysis; whereas, the tissue has a color or appearance that is readily identifiable as being tissue. One such material is a low density polyethylene homopolymer such as Quantum Chemical Co. Petrothene® NA 601-04. Other sectionable materials could be used that appear cloudy or take a bit of stain. So long as the pathologist is not distracted by a cellular structure of the sectionable material that is herein referred to as non-distracting.

Since the sectionable filter will be used to separate small tissue particles from suspended liquids it may be necessary to modify the surface tension or wetting characteristics of the plastic to allow the fluid to pass rapidly through the filter screen while retaining samples. Surface treatments such as Plasma etching, Corona Discharge, Ion beam, Hydrogels, Photolink™ surface modifications can be used. These surface treatments may also be used to attract or retain tissue on any of the filters or stages. As will occur to those skilled in the art, there may be a need to have an affinity coating to attract mucosal tissue fragments as an example.

Stage Cassette Configurations

FIG. 2 depicts a stage cassette frame 10' in which both sectionable and non-sectionable tissue trapping stages can be inserted. It is a rectangular version of the cassette frame 10 shown in FIG. 1. Stage detent grooves 18' are positioned inside the periphery of the cassette frame and projections 20' on the stages mate to the stage grooves allowing for various vertical positions of the sample surface to be established with respect to the stage cassette frame as above discussed.

Sectionable Filter Cassette Configuration

In FIG. 2, B''' shows a sectionable filter stage for the cassette frame configuration. This type of filter could be used to process small pieces of tissue that arrive in the laboratory in a container with fixative and the container does not already contain an integral sectionable filter.

Sectionable Immobilization Stage

Figure 3:
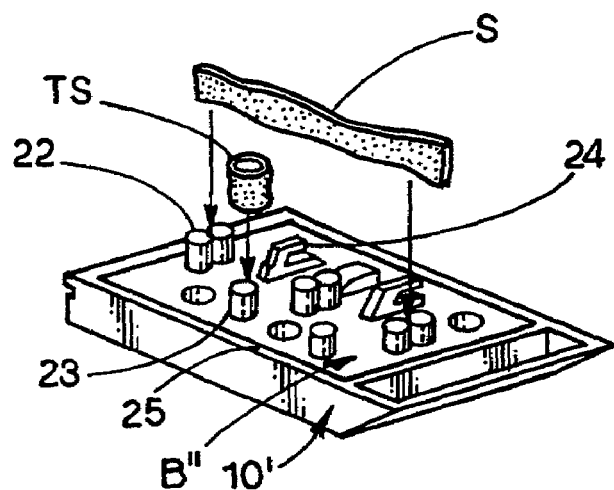

In FIG. 2, B" shows a sectionable immobilization stage. FIG. 3 depicts the sectionable immobilization stage B" assembled in the stage cassette frame as a platform and ready for tissue loading. FIG. 3 also shows the installation of a long thin biopsy sample into gripping pins 22 on the stage. These allow the pathologist to manually orient the tissue samples for sectioning at the point of gross in of the ample. FIG. 3 also shows a tubular tissue section TS such as an artery or a vein being installed over a vertical tissue pin 23. This allows for transverse section of a luminal structure.

Additional hooks 24, pins and gripping elements can be provided on these stages to allow the pathologist to select the most appropriate immobilizing method and orientation for each tissue sample. As shown in FIG. 3, the gripping features and actual sample surface of the stage extend above the stage cassette top rim 25 when the stage is positioned in the top most groove. This facilitates tissue loading.

Figure 4:
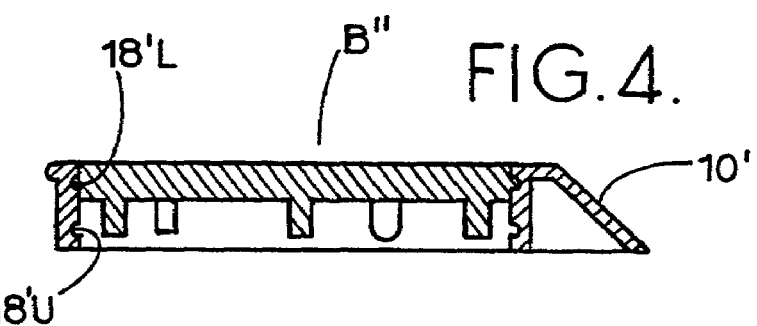

FIG. 4 again shows the sectionable immobilization stage B" assembled in stage cassette frame 10' and turned upside down. In this view the gripping features and sample surface are beneath the stage cassette frame rim 25, offering protection to the tissue samples from dislocation during tissue processing. The stage has been adjusted to rest in lower groove 18'L of the stage cassette frame.

Figure 5:
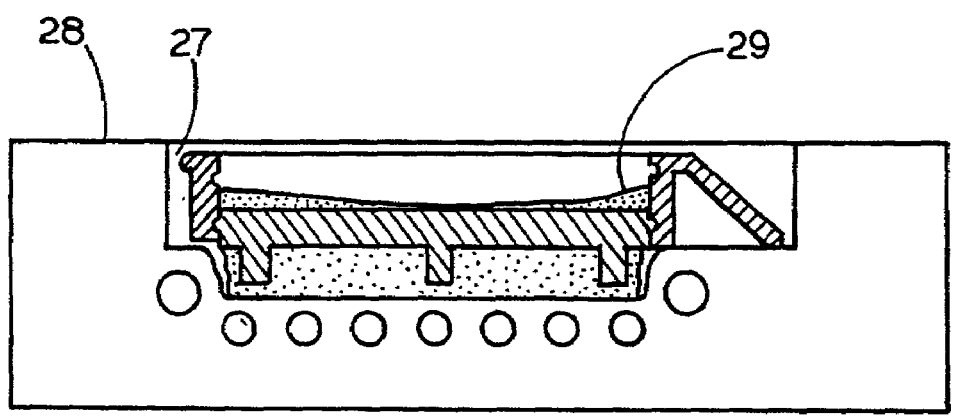

FIG. 5 shows sectionable immobilization stage B' positioned once again into upper stage groove 18'U of the stage cassette frame, as it was for tissue loading. In this view, however, the sectionable immobilization stage and frame have been turned upside down and are shown pressed into mold cavity 27 of a wax mold 28 ready for embedding in wax or paraffin 29. The tissue samples are thus presented as close as possible to the eventual sectioning surface.

Non-sectionable Stage

Figure 6:
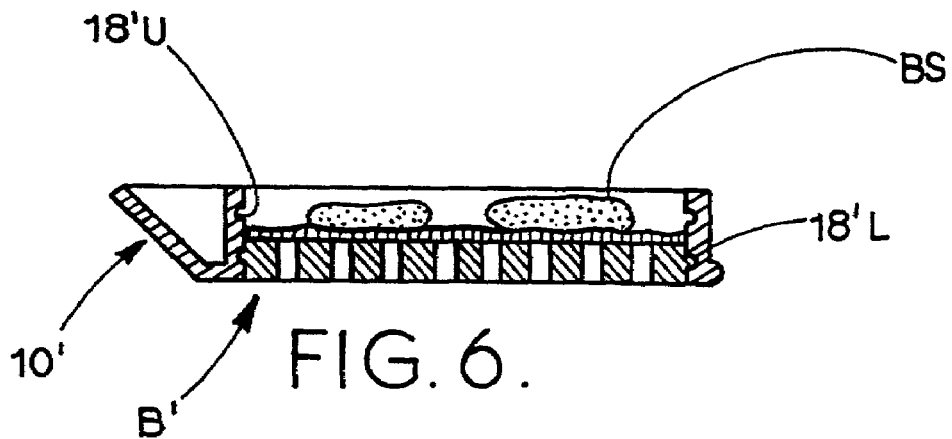

In FIG. 2, B' shows a non-sectionable stage on which large tissue samples can be immobilized. The non-sectionable stage can be used when the sample is large enough that it extends well above the sample surface of the stage and sections of the wax embedded sample can be made without running into the actual stage with the microtome. FIG. 6 shows a cross-section of the non-sectionable stage assembled into a stage cassette frame 10'. The stage has projections which engage the stage detent grooves to allow for the vertical translation of the stage within the cassette frame whereby biopsy sample BS can be oriented and located for proper treatment. Movement of the filter or stage with respect to the frame is effected by simply pushing the filter or stage with respect to the frame. The filter or stage and the frame are made of flexible materials and thus will deform when such pressure is applied. This deformation will permit the projections to pop out of one groove and then slide until they reach the next groove. At that point, the projections will pop into that groove.

Figure 7:
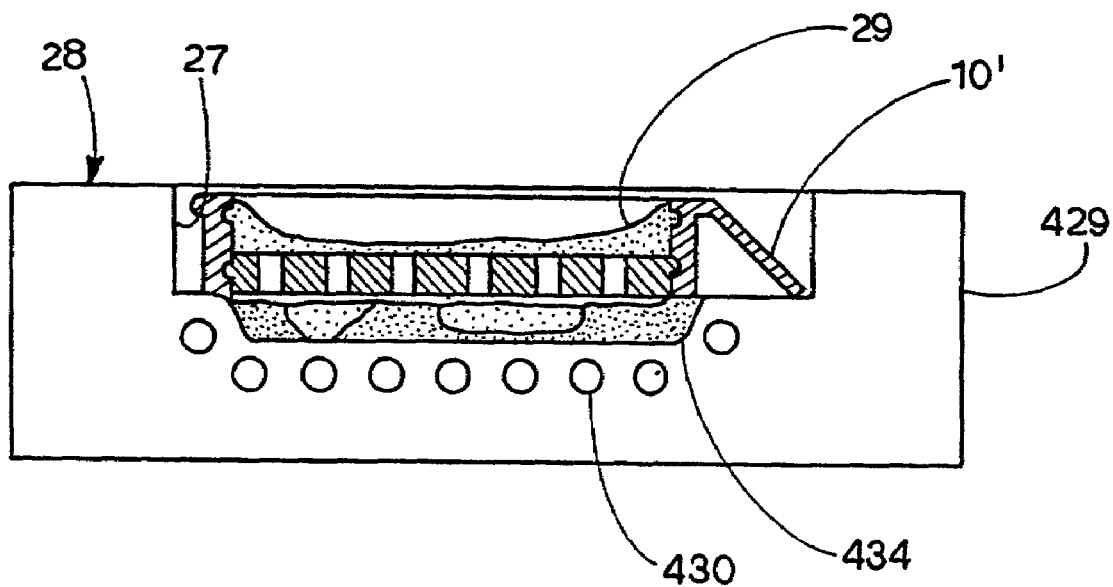

FIG. 7 shows the non-sectionable stage and cassette frame in the position for wax embedding in the mold cavity. Here, the tissue sample is presented as close as possible to the eventual sectioning surface. As will be discussed below, an immobilizing media keeps the tissue in place on the sample surface of the stage during tissue processing and wax embedding.

The tissue trapping platforms have numerous applications for use. Specific applications of the invention are discussed herein.

These are shown as examples of methods to trap and transport tissue samples to the histology lab. It should be noted that there may be many more uses for this technology so as not to limit the tissue trapping platform concepts and applications to the disclosed applications.

In general, the invention includes a method for preparing biopsy tissue samples for histological examination comprising:

removing a tissue sample from a patient; placing the tissue sample onto a suport; immobilizing the tissue sample on the support; subjecting both the support and the tissue sample immobilized thereon to a process for replacing tissue fluid with wax and impregnating the tissue sample with wax, embedding the tissue sample in a wax mold to form a solid block of wax, using a microtome, slicing the solid block of wax into thin slices; and mounting at least one of the thin slices on a support member for examination. It is also noted that one form of the invention includes a tissue support that can be successfully mictrotomed, while another form of the invention includes a support that is porous. In that case, the tissue support will be embedded with the tissue sample in the wax and both the sample and the support will be sectioned using a microtome.

The invention also, broadly, includes a tissue analysis automation process which includes placing tissue on a machine manupulable support; immobilizing the tissue on the support to maintain a selected orientation of the tissue on the support; and processing the immobilized tissue along with the support to replace tissue fluids with wax, as well as a method of conducting analysis of tissue biopsy samples comprisng: harvesting tissue samples from a patient; placing the harvested tissue samples onto a machine manipulable tissue support; immobilizing the tissue samples on the tissue support; and processing the tissue samples and the tissue support to replace tissue fluids with wax.

Automation of Tissue Processing and Histologic Section Preparation

FIGS. 8, 9, 11–16 illustrate a method for automating the gross in process, the immobilization of tissue and the tissue embedding process. Currently, the histotech or pathologist performs all of the preparation procedures such as grossing in the samples and placing the tissue into cassettes prior to putting them in the tissue processor. The histotech additionally performs all of the manipulations required to place the tissue into the molds for paraffin embedding.

Automated Dispensing of Samples in Fixative Solution

Figure 8:
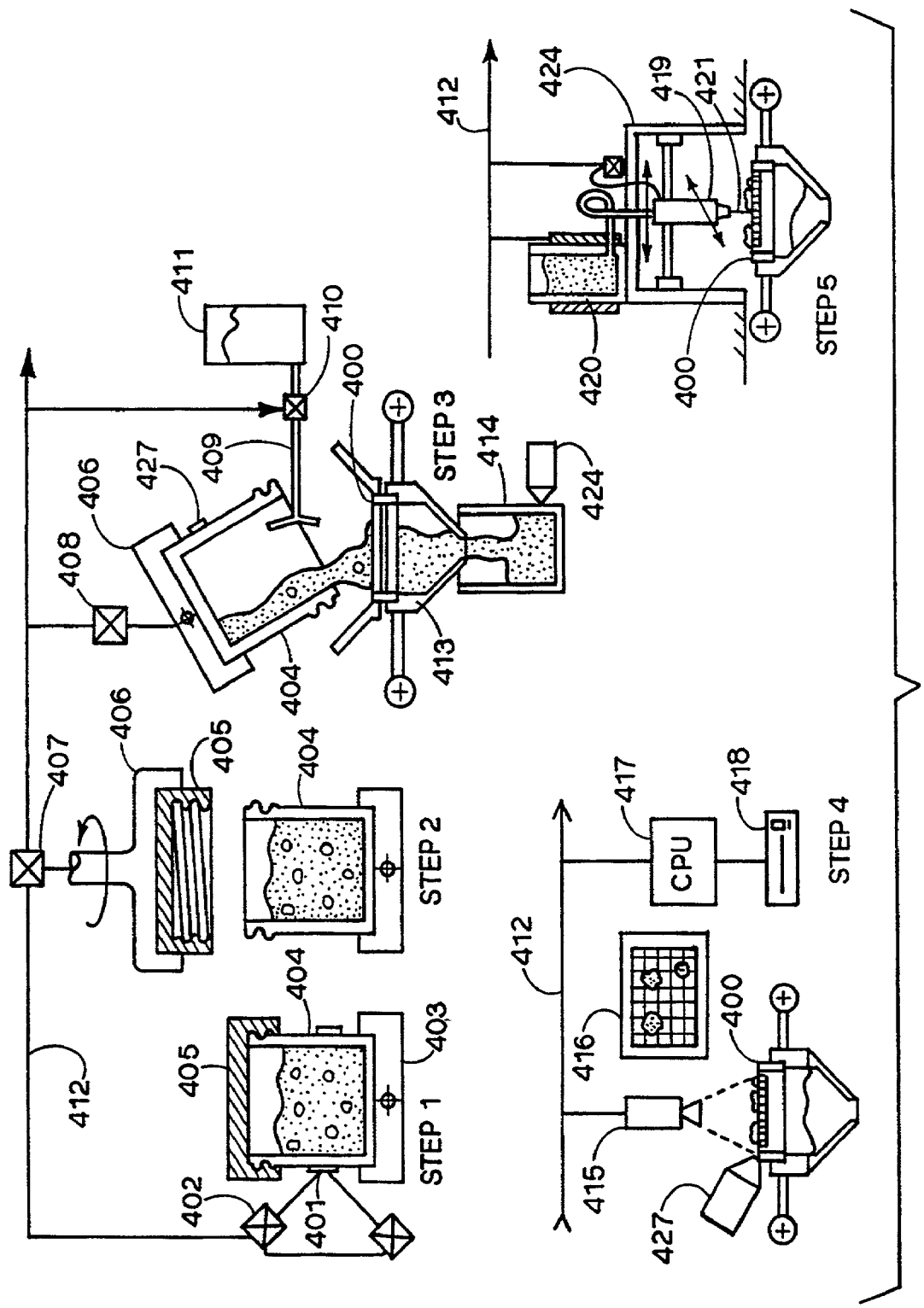

FIG. 8 depicts a process whereby small biopsy samples are removed from containers and filtered through a sectionable filter. In FIG. 8, Step 1 shows a bar code reader 402 which reads a digital bar code 401 off the side of biopsy container 404. This bar code number is matched to a laboratory accession number which is used to track the tissue samples through the processor and the wax embedding station.

Step 1 of FIG. 8 shows the biopsy container 404 placed in container gripper 403. Bar code 401 is read and recorded by reader 402 which communicates with CPU 417 via central data bus 412. Bar codes and bar code readers, as well as the associated computer equipment and software that are used for this process are known to those skilled in the art. Therefore, based on the teaching of this disclosure, those skilled artisans will be able to select this equipment and software. Therefore, such equipment and software will not be further discussed.

In Step 2, cap gripper 406 powered by cap removal servo 407 removes and discards the standard biopsy container cap 405. Cap grippers, as well as the other mechanical equipment necessary to carry out the steps and to practice the invention disclosed herein, will be known to those skilled in the art of creating automated machines, see, for example catalogs such as published by Techno Sommer Automatic of 2101 Jericho Turnpike, New Hyde Park, N.Y. Many standard off-the-shelf components exist as standard catalog items, such as Transfer and Pick-n-Place mechanisms can be esaily modified to interface with the tissue handling invention disclosed herein. In addition, off-the-shelf catalog items such as programmagle logic controllers are available to control a multitude of environmental variables, drive systems, and timing issues to create automated machines of the complexity required to carry out the invention disclosed herein based on the teaching of this disclosure. Accordingly, details of such equipment will not be presented.

In Step 3, the container is tilted and the contents are dispensed into a funnel stage 413 directing the contents first through sectionable filter 400. Again, as discussed above, such elements which hold and manipulate containers such as element 406 which then dispense the contents of the container would be modifications of off-the-shelf components from companies that supply such parts to those skilled in the art of creating automated machines. As depicted, this is a sectionable filter but could alternatively configured as a sectionable filter cassette. The filtrate is normally discarded as waste, however, the filtrate can be directed into a cytospin container 414. When a cytology test has been ordered, it is indicated by the technologist or pathologist by placing a special cytospin indicator 427 on the biopsy container. Such an indicator is machine readable in order to direct a machine to retrieve additional fluid samples dispensed from a container or to command additional testing. These examples illustrate that separate machine-readable indicators are used in conjunction with the sample containers and platforms. However, these indicators could be combined into one machine-readable code. Such indications can be either hand applied or could be coded into a pre-processed or in-process labels. These examples merely illustrate the possibilities of indicating to the machine the pathologist's request for different tests to be applied to the sample. Bar or any other machiine-readable code cold be used to enable this invention and are included to illusrate how the machine designer will process instructions about how to handle individual samples within machine environments. In addition, such machine-readable codes would also need to be compatible with existing machine-readable code in the current pathoogy laboratories. Bar-code reader 402 notes the indicator and directs the appropriate pore size sectionable filter to be automatically installed along with cytospin container 414. The cytospin container is automatically labeled with the biopsy sample's unique accession number with printer head 424 (machine and/or human readable). The funnel 413 could be a single use device which is disposed of after use to prevent cross contamination of specimens.

Whether or not a cytospin container is used, a rinse cycle is initiated after the biopsy container is emptied. Washing wand 409 dispenses rinse solution from reservoir 411 controlled by rinse valve 410. The rinse solution will clean out the biopsy container of any particulate that will then, if large enough, be trapped on sectionable filter 400. The smaller cellular components of the biopsy flow through filter 400 and are either discarded or captured in cytospin container 414 for further processing.

Automated Gross in of Samples

In Step 4, filter stage 400 moves into a gross in station where an image capturing device such as a digital camera or video camera 415 records an image 416 of the tissue samples on sectionable filter 400. A 1 mm (or other gradation) grid reticule on the camera lens may be used for a size calibration. Traditionally, the number and size of tissue samples in a cassette are described at gross in for future reference. With the present invention, the digital picture contains a record of this information, that may be printed on the surgical pathology report, or may be accessed sometime in the future if questions arise. The digital picture is displayed for the histotech to verify that a record has been created for the particular biopsy sample. The information is digitally compressed by CPU 417 and stored on an optical disk or other data storage media 418. In addition, given the information in the digital image, the processor can determine if too much tissue is present on a given platform and reject it for further treatment by the histotech. Additional scanners such as infra red could be used as a diagnosis tool.

In addition, the digital image can be used to transcribe an appropriate gross description of the surgical pathology report of the specimen. One such requirement of the system might include a physical record of the number and sizes of the tissue samples present on the tissue platform. Information gathered by the digitized video image could be stored and analyzed a suitable computer program in order to determine the number and size of the samples present in the tissue container. Digital systems are particularly well suited for this applicaion. The image area can be divided into small coordinate areas, such as the pixels which make up the imaging device. Through a simple computer program, each pixel can be converted to a known physical size, and groups of pixels can be lumped together to create calculated surface areas. Again, this is an area in which a sub-speciality such as pattern recognition and video imaging is integrated into this invention to enable new combinations that were not previously known. In addition, one should not limit the automated gross in procedure to video only. Scanning sonar or radar could be employed to give a more three-dimensional record of the tissue samples. Such a system would involve a scanning head, which would transmit and receive electromagnetic signals that would use a reflected signal to reconstruct a non-contact picture of the tissue samples, much the same way as sonar has mapped the bottom of the ocean surfaces but in a much smaller scale. The digitized image is analyzed by CPU 417 to determine the number and size range of the pieces of tissue in the specimen. This information is passed through an interface to the laboratory anatomic pathology computer system. Through appropriate programming, such as macros similar to ones which are presently in use in the word processing systems of most laboratory systems, the system transcribes an appropriate gross description of each specimen for incorporation into the surgical pathology report.

This system uses a combination of electronic imaging which was captured in the previous step, and in combination with computer matching systems allows printed text to be recorded along with the video image. For instance, in the pattern recognition system described above, the computer would determine that for instance three tissue samples were obtained, each three square millimeters in area. The computer would write a file that stores the proper code for each tissue sample recorded and its individual size. The computer would then print out a written text report with a prerecorded description matching that of three individual samples each with their own respective sizes given in square millimeters. Thus, there would be both a visual record and a text record of the samples obtained and recorded. This would replace the current practice whereby the pathologist dictates a spoken description of the tissue samples onto magnetic tape, which is subsequently listened to by a transcriber who types a written description for the pathology report. This would reduce the cost for each written description of the pathology report. CPU 417 controls all of the stations in steps 1 through 5 and records all events, tracking numbers on digital storage media 418. An accession or tracking number 423 (see FIG. 9) is printed (machine and/or human readable) on the cassette frame to identify the samples. This number relates to the bar code number from the biopsy container if the automated decanting process was used; or to a sequential log number which is also printed on a label and presented to the technician to attach to a requisition form with specific information about the origin of the sample; or the information would be tied to the computerized log book in the histology lab.

Immobilization of Tissue on Platform

The tissue immobilization process on the filter or stage will now be discussed. Both manual and automated immobilization techniques have been proposed. The pathologist or technician is able to properly orient samples as required for sectioning by placing the samples on an appropriate tissue trapping platform just prior to gross in. The immobilizing process maintains the pathologist-specified orientation of the tissue throughout the histology preparation process. No further treatment is required for samples placed on a sectionable immobilizing platform since its gripping features act to hold the tissue in place throughout the histology preparation process. The tissue on a non-sectionable platform or sectionable filter cassette may require further immobilization treatment.

Tissue immobilizing adhesives or the like such as adhesive BIS indicated in FIG. 6, can be included on the tissue support whereby tissue samples are quickly immobilized on contact with the tissue support. For instance, cyanoacrylate adhesive works well to bond larger tissue samples to the non-sectionable stages. The adhesive cures quickly and bonds the tissue securely and further does not break down in the processor fluids. Additional adhesive-like substances can be coated on the surface of the filter or stage making a "dry adhesive" which can be activated by the moisture in the tissue sample. Additionally ultraviolet curing dry adhesives can be used; the adhesives are dry coated and do not become "activated" until catalyzed with ultraviolet light. Still further, coatings with protein affinity can be deposited upon the filter or stage whereby contact with any protein containing material will catalyze the adhesive. Other tissue immobilizing techniques and methods can include the techniques of Dry Net, ballistic particle deposition and use of adhesives are disclosed as well as other methods ranging from simple to complex.

Step 5 of FIG. 8 includes an immobilization step. After gross in, the filter stage is moved by appropriate machinery to be immobilized. Appropriate machinery is available from catalogs such as the Nyden catalog published by Nyden, a subsidary of Nycom, Inc. and from Delta Tau Data Systems, Inc of Northridge, Calif. Delta Tau Data Systems also sells programmable Temperature Controllers. If the sample has been placed onto a sectionable filter, a sectionable filter cassette, or a non-sectionable stage, immobilization is desirable to keep the tissue samples in place while in the fluid medium of the tissue processor. In this embodiment the immobilization device is shown as a ballistic particle head 419 fed by a heated pressurized reservoir 420 of material such as low density polyethylene. The ballistic particle head 419 is on an x-y gantry 424 which enables the deposition of a fine web-like netting to be created over top of the samples. Using information from the digital image taken in Step 4 and described above, an "intelligent net" could be created specifically capturing pieces of tissue rather than covering the whole filter or stage surface.

Although the preferred embodiment is shown as ballistic particle deposition of material, many other ways could accomplish the same result such as the thermal bonding of a net material over the tissue (Dry Net, see FIGS. 17 and 18); or by spraying a thin glue-like substance over the tissue and filter or stage; or by spraying a thin glue-like substance on the sample surface of the filter or stage prior to tissue loading; or by spraying a thin layer of agar or other gel over the tissue and filter or stage; or by using a bio-affinity coating that would allow the tissue to bind to the surface of the filter or stage after exposure to an ultraviolet cure period or without the ultraviolet cure; or by using an ultraviolet cure adhesive coating on the filter or stage surface; or by using a coating of albumin or L-Lysine or some other sticky protein on the surface of the filter or stage. Such alternatives will occur to those skilled in the art based on the teaching of the present disclosure.

Figure 17:
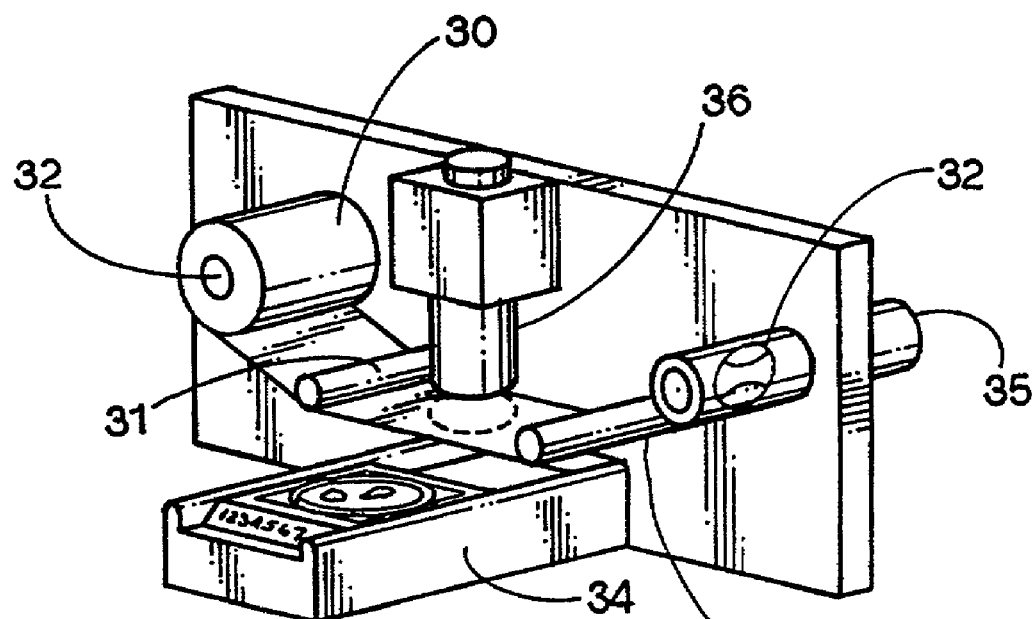
Figure 18:
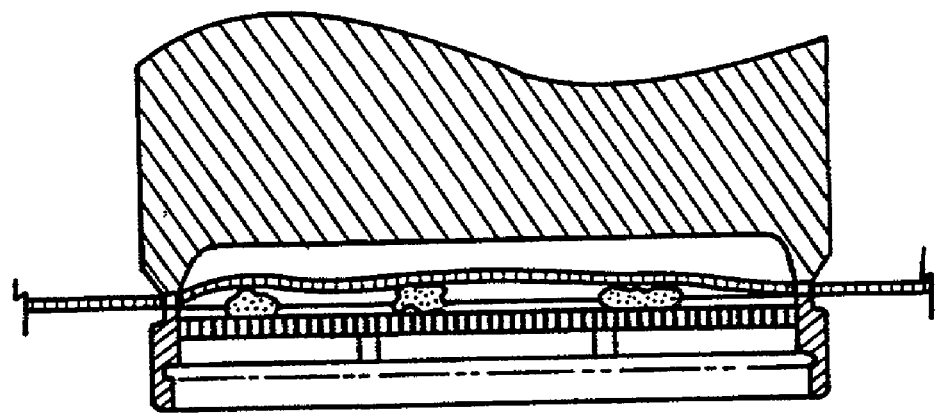

In the Dry Net technique the tissue on a platform is then placed into an immobilizing fixture seen in FIG. 17. The immobilization fixture brings the platform underneath a polyethylene net 30 which is fed by rollers 31 from a feed reel 32 to a take-up reel 33 toward a transfer base 34 on which the cassette is supported. The web is moved by a stepping motor 35 connected to the rollers. The platform is positioned underneath the net and a bonding head 36 is brought down from above to ultrasonically or heat weld the net to the periphery of the platform (FIG. 18). This traps the tissue between the sample surface of the filter or stage and the net. The net is preferably made from the same sectionable material as the filter or stage and is preferably porous so that the tissue processing fluids and the wax can penetrate around the tissue.

Two methods for use of a wet adhesive process to immobilize the tissue on a filter or stage are disclosed whereby either an adhesive is sprayed onto the sample surface of the filter or stage prior to loading with the tissue sample; or the adhesive is applied after the tissue has been placed on the filter or stage. In order to be effective, the latter method requires the adhesive to wick underneath the edges of the tissue and thereby hold down the tissue throughout processing. Adhesives such as cyanoacrylates are well suited for this application since moisture sets off the rapid curing process. Tests have shown that the cyanoacrylate tissue bond is impervious to the chemical and temperature environments of the tissue processor and the wax embedder. It does not interfere with the sectioning or staining of the samples nor does it interfere with the tissue histology.

Any substance which does not interfere with the histologic sample preparation, as described above, can be used to immobilize and affix the tissue to the platform. The immobilization process depicted in FIG. 8 uses ballistic particle deposition in which small particles of molten plastic are ejected from a nozzle towards the filter or stage and tissue. The ballistic particle technology is currently in use in the rapid prototyping process whereby plastic models are constructed from three dimensional CAD files. Since those skilled in the art of ballistic particles and their movements will understand this technology, it will not be further discussed.

If the tissue sample has been loaded onto a sectionable immobilizing stage which does not require an extra process to secure the tissue to its surface, a machine readable code on the platform could identify the platform type and allow for this specific type to bypass the immobilization step and continue on to the tissue processor.

Figure 9:
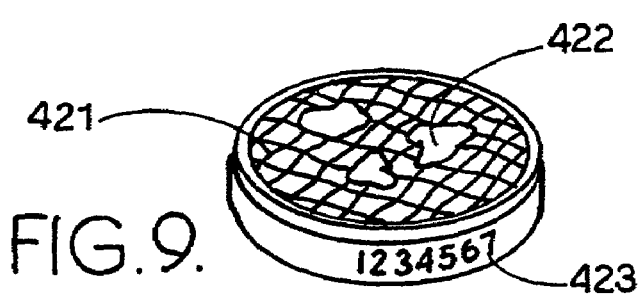

FIG. 9 shows immobilized tissue 422 with immobilizing material 421 retaining the tissue on a sectionable filter. The tissue will not be dislodged from the sample surface during further processing.

Once the tissue is immobilized on the filter or stage, the platform can be placed in a standard storage rack or automatically introduced into the tissue processor. If the filter or stage is not already in a platform configuration, it will be automatically placed into the appropriate four sided cassette frame before progressing to the tissue processor.

The teaching of the present inventors has also shown that immobilization can be carried out in a variety of ways, including glues, nets and the like. However, tissue immobilization can also be achieved in other ways as well, including capturing the tissue sample in a special container. To keep the tissue from being cross-contaminated and properly oriented and spaced during processing and embedding, the container can be closed and sealed. To gain access to the tissue after embedding, the container can be formed of sectionable material so the container can be sectioned along with the tissue. Since those skilled in the art are used to working with containers, using a container in this manner will permit them to use familiar items.

Therefore, by adapting the herein-disclosed teaching to containers, the present invention can be made into a form that will be acceptable to those skilled in the art who wish to continue working with familiar items.

Automated Wax Embedding Process

In general, the automated process prepares the tissue sample for embedding in wax, and embeds the tissue sample in wax. Then, the tissue sample can be sliced into thin slices using a microtome and at least one of the slices mounted for microscopic examination. Broadly, the method of preparing biopsy tissue samples for histological examination comprises: removing a tissue sample from a patient; storing the tissue sample in a container; dispensing the contents of the container onto a support; immobilizing the tissue sample on the support; subjecting both the support and the tissue sample immobilized thereon to a process for replacing tissue fluid with wax and impregnating the tissue sample with wax, and embedding the tissue sample in a wax mold to form a solid block of wax. As above discussed, one form of the invention includes a porous tissue support while another form of the invention includes a tissue support that can be successfully sectioned by a microtome. A microtome is then used to slice the solid block of wax into thin sections which can be used for further examination. If the tissue support is microtomable, it, or part of it, can also be embedded in the wax block.

Figure 11:
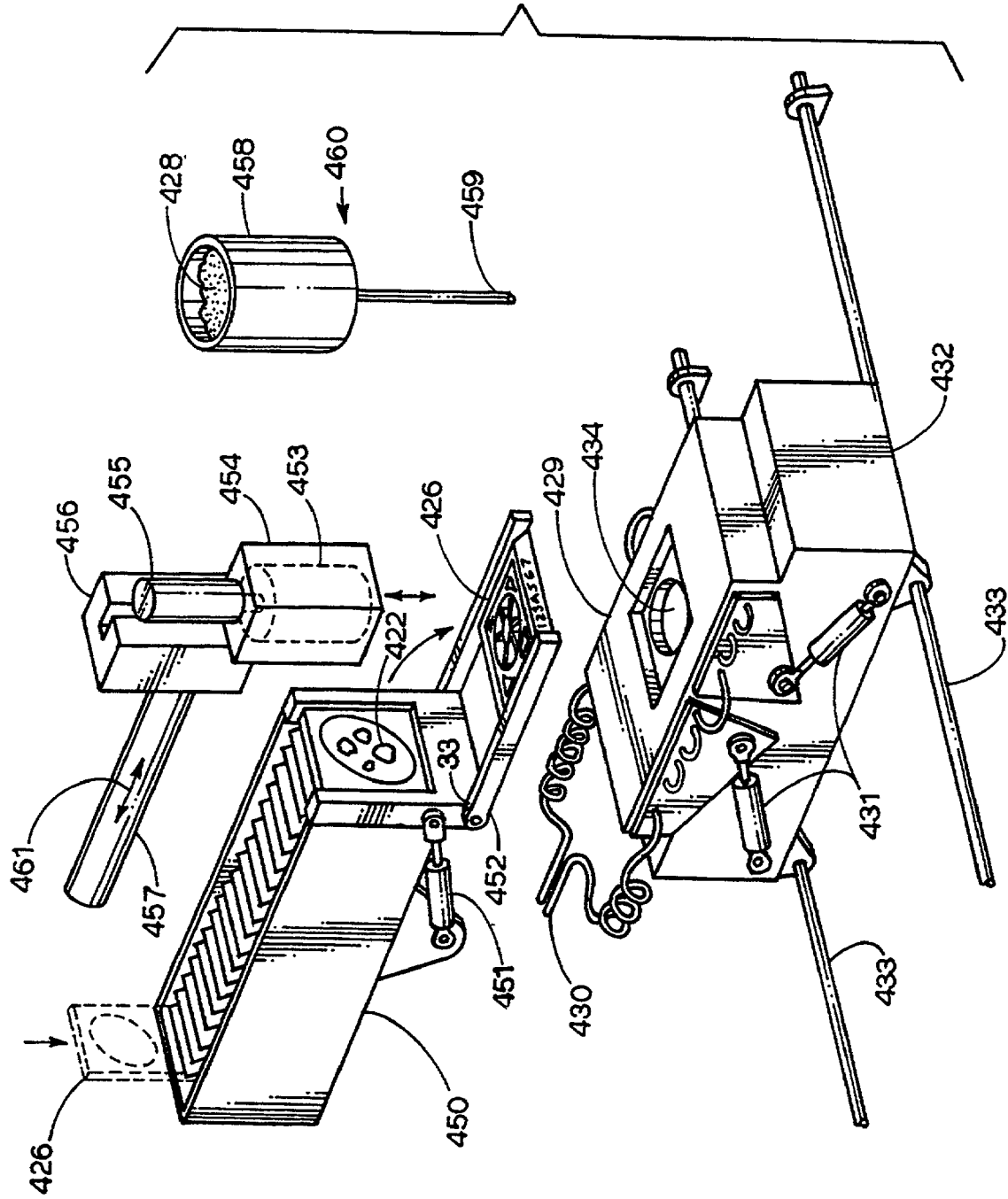
Figure 12:
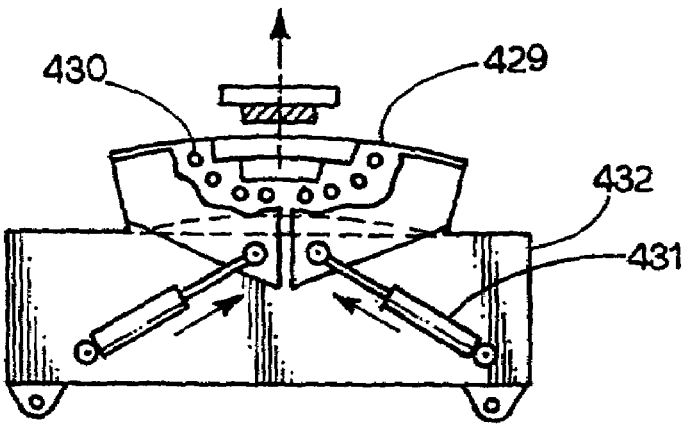

More specifically as shown in FIG. 11, as platforms 426 emerge from the tissue processor they can be stored in a rack 450 for batch processing or sent directly to the automated wax embedding station. FIGS. 11 and 12 illustrate an automated wax embedding station. Flip down fixture 452 at the end of the storage rack 450 includes apparatus to transfer and orient the platform with the tissue face down in the wax mold. When the platform comes into position in the rack, sensors note this and activate actuator 451. Actuator 451 includes a cylinder and is operated by a motor (not shown) to rotate flip down fixture 452 into the horizontal orientation to enable the pick and place head 457 to access the upside down platform. An ear 33 is rotatably connected to rack 450 to facilitate this movement. Pick and place head 457 has three functions: a longitudinal function shown as an arrow 461; a vertical picking head 454 and a setting head 453. Vertical picking head 454 can move vertically on stage 456 by means of a motor (not shown). Actuator 455 moves setting head 453 vertically via a motor (not shown). Mold base 432 is one of a pair of mold bases used in this machine. Each mold base has a mold sub base 429 which houses molding cavity 434. Additionally, the system has two paraffin dispensing stations 460 which include hot molten paraffin 428, heated reservoir 458 and dispensing tip 459. Mold base 432 can be actuated to move in a linear fashion from left to right. Movement of the elements of the wax embedding processor are controlled by motors which are, in turn, controlled by computers. Movements of the elements for wax embedding can be controlled by a microprocessor such as a PLC (programmable logic controller) or the like. Such controllers are available off the shelf and are capable of controlling sensors, drive motors, switches and valves and other electromechanical components. Again, a machine design engieeer skilled in this area would be capable of performing automted wax embeddding tasks. It is noted that each individual station may be controlled with its own PLC, or many PLCs depending on the number of parameters to be controlled. It is also noted that numerous PLCs can be controlled by a central microprocessor which would oversee each of the individual components and make sure that the throughput is timed accordingly. In this manner, while individual controllers may be able to sense and control small subsystem areas such as wax embedding, one central processor can keep track of all subsystems and batch conrols and can prevent sequential backups.

Figure 13:
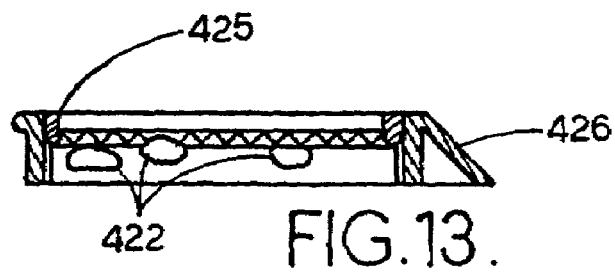
Figure 14:
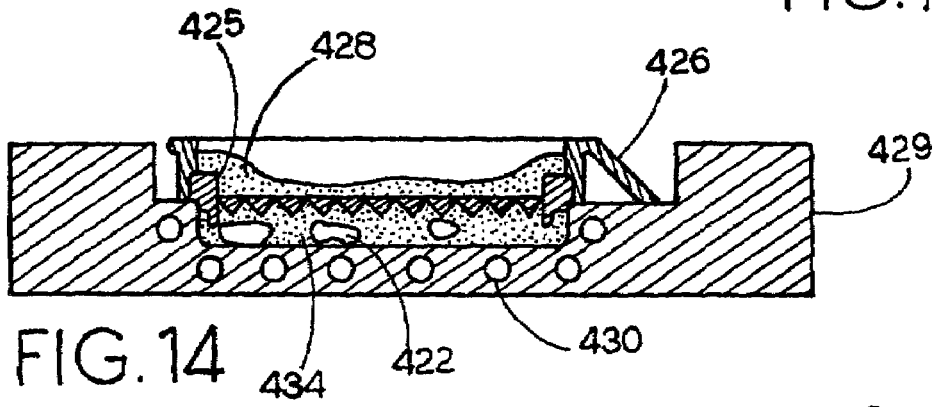
Figure 15:
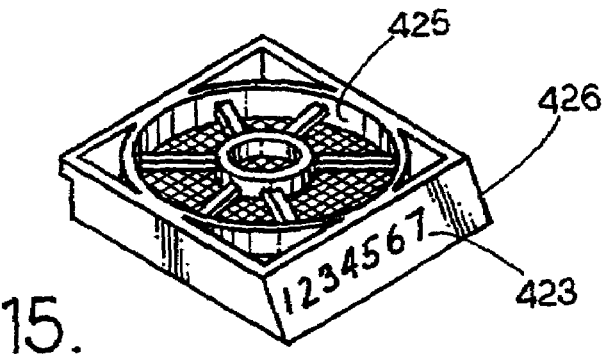
Figure 16:
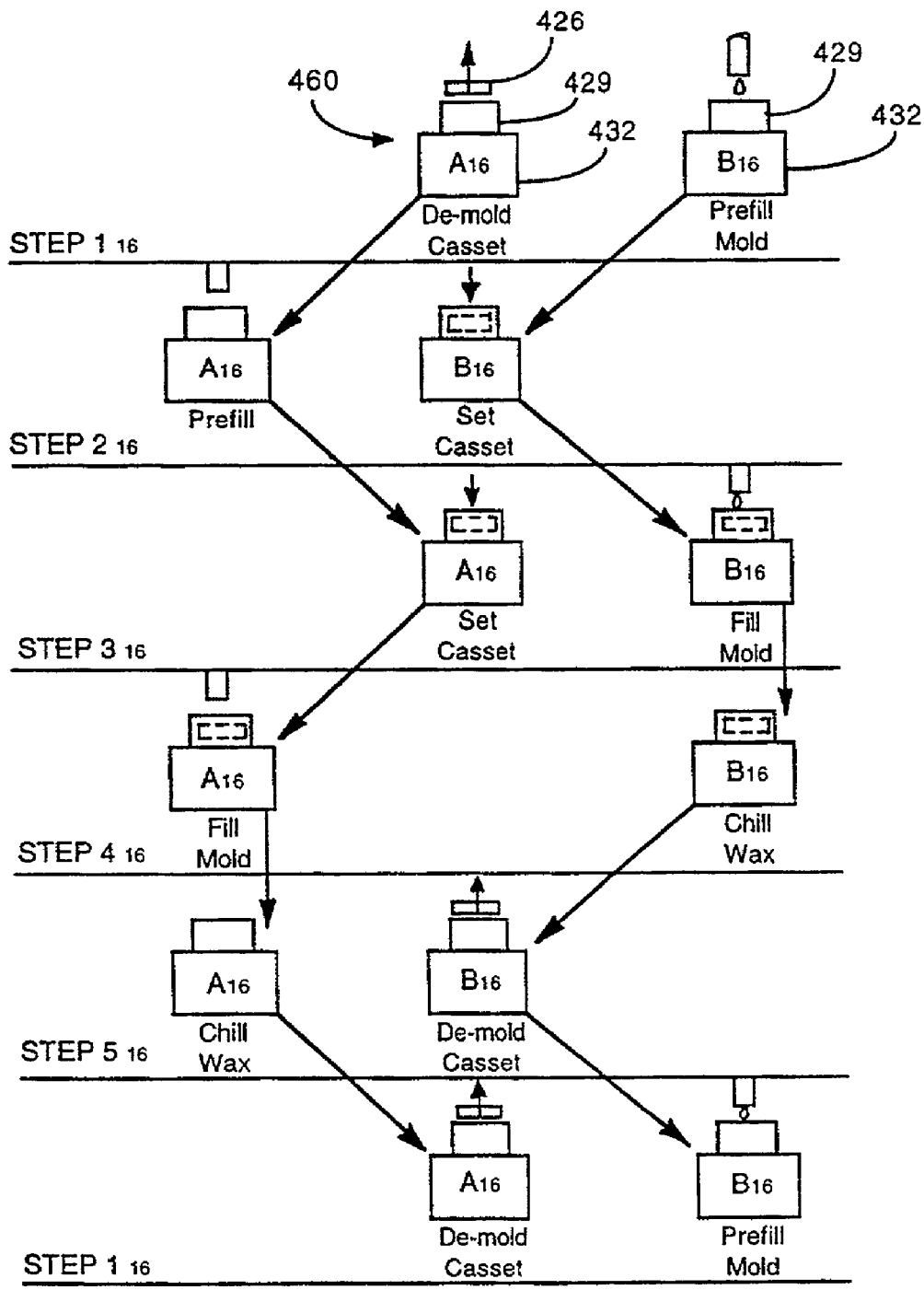

FIG. 16 depicts the operating sequence for the pair of mold bases. Referring to FIGS. 11 and 16, it can be understood that in Step $1_{16}$, the available mold base (labeled $A_{16}$) is moved over to the paraffin dispensing station 460 where in Step $2_{16}$ a small quantity of paraffin is dispensed into mold cavity 434 prior to the platform being positioned in the mold. This provides a thin rapidly cooling layer of paraffin in the bottom of the mold, for the tissue and filter or stage surface to be set into. In Step $3_{16}$ the mold base then traverses under flip down fixture 452. The pick and place head 457 comes down onto the platform, grips it and sets it into the paraffin layer in the mold cavity. FIGS. 13–15 depict a sectionable filter 425 that has been dropped into a filter cassette frame 426 and is shown flipped over, ready for embedding in the wax mold form. The process is identical for the other platform configurations.

In FIG. 13, immobilized tissue 422 is protected by cassette frame 426 while in the tissue processor since the sample surface is vertically centered within the cassette.

Setting head 454 (FIG. 11) applies and maintains pressure on the sectionable platform which translates vertically downward within the cassette frame into mold cavity 434. This downward vertical translation is depicted in FIG. 14 and can be seen by comparing FIGS. 13 and 14. This insures that the tissue samples are set in the bottom-most position in the mold cavity and therefore, when sectioning, the microtome will have easy access to the tissue sample. As can be seen in FIG. 12, to facilitate the setting of the paraffin layer, mold sub base 429 is cooled via cooling channels 430 which surround the cavity 434. The cooling channels are connected to tubes which lead to a separate chilling unit for circulating cooling fluid to maintain a temperature at the mold sub base of approximately −7° C.

Once the platform and tissue samples are set in the pre-fill layer of paraffin, the pick and place head is raised and the mold base is again translated laterally to the paraffin dispensing station 460. In Step $4_{16}$ the mold is automatically filled to the final level. Mold base 432 dwells at this station for a period of time (Step $5_{16}$) post filling during which time the sub base is chilled to set the newly added paraffin.

In Step $1_{16}$ again mold base 432 translates back to the center position where the pick and place head 457 comes down and removes the platform from mold sub base 429. In order to facilitate easy removal of the hardened paraffin block and attached platform 426 from the mold sub base, the mold sub base is pivotally mounted on the mold base with actuating mechanisms 431 that are operated and controlled by computer controlled motors (not shown). Mold sub base 429 is preferably made of a flexible material such as urethane, which allows the mold to be flexed, popping the hardened paraffin block out as shown in FIG. 12. Additionally, the paraffin will not stick to the urethane material. With the paraffin block removed, the cycle for one mold base is complete. FIG. 16 depicts how two mold bases ($A_{16}$ and $B_{16}$), one pick and place head and two paraffin dispensing stations can be used to improve efficiency of the embedding process. $A_{16}$ and $B_{16}$ mold bases alternate stations in an efficient work flow pattern.

The automated process will allow the completed paraffin block to be transferred directly to the microtomy station where it is sectioned, applied to a glass slide and stained.

Any or all of the above described automated stations could be configured into a package to best meet the needs of a particular laboratory. Automation of every step would not be a requirement.

Figure 10:
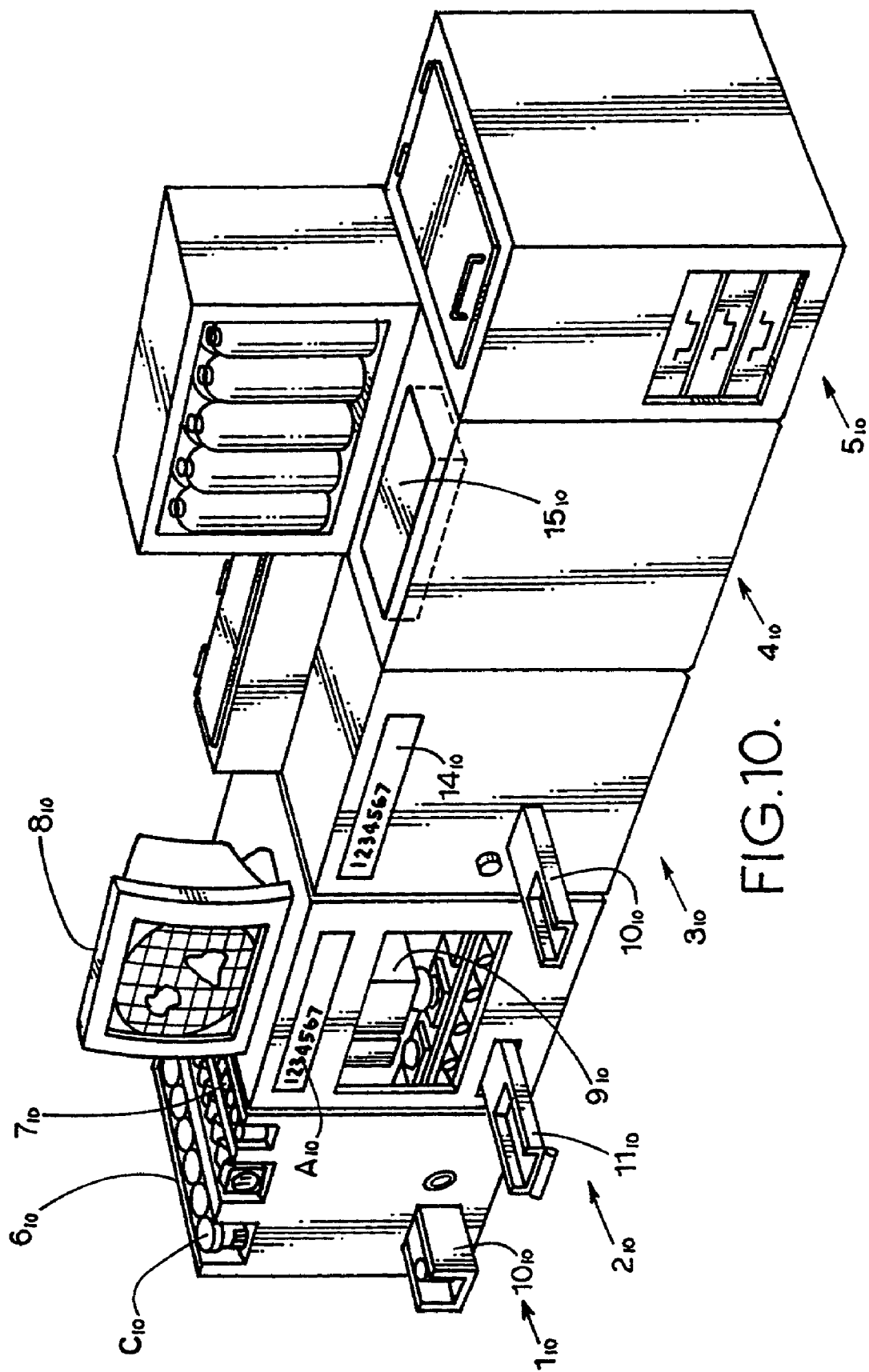

FIG. 10 shows a finished product design of a fully automated system. It is comprised of automated processing stations for each of the major steps for histology sample preparation; each could be used individually or as a completely automated system. There are five automated stations shown:

$1_{10}$. automated sample dispensing and platform selection
$2_{10}$. printing and video gross in unit
$3_{10}$. immobilization
$4_{10}$. tissue processing (prior art technology) and
$5_{10}$. automated wax embedding.

Additionally, biopsy container storage $6_{10}$ is located adjacent to a gross in location.

In the first station, automated sample dispensing and platform selection, biopsy sample containers $C_{10}$ are stored in a rack awaiting automated dispensing. Blank platforms and cytospin containers are stored in an area $7_{10}$. Sample containers are brought into the automated processing system. A bar code reader deciphers the machine readable code on the container, which indicates whether a cytospin container is required for this particular sample. The sample container is automatically opened and the contents are decanted onto a sectionable filter. If required, the eluate is collected in a cytospin container for further processing. There is also a single container entry tray which can be used to accommodate a sample which needs to be processed immediately; samples entered there are given priority over samples that may already be in storage.

In the second station a printer head prints a laboratory accession number $A_{10}$ from the laboratory log records onto the cassette frame and cytospin container if one was required. The platform is moved for digital or video gross in and display on screen $8_{10}$ by video camera $9_{10}$ and a single digital or video image is recorded of the tissue samples on the platform, capturing the identifying accession number as well. A manual loader $10_{10}$ can also be used.

A single entry tray $11_{10}$ can be provided at this station as well to allow entry of platforms which are loaded manually such as the sectionable or non-sectionable stage platforms or a sectionable filter cassette that has been manually prepared. The printing and video gross in functions are performed on these samples as well.

The platforms are then moved individually into the third station $3_{10}$ for immobilization of the tissue samples. The immobilizing technique is applied to the tissue and filter or stage and current sample number is displayed on screen $14_{10}$.

The platforms with immobilized tissue samples are transferred into a holding tank $15_{10}$ for batch processing or are sent directly into the tissue processor for continuous processing.

From the tissue processor, the platforms move into the automated wax embedding station (station $4_{10}$). They may also be held in storage there and processed in a batch, if required. The automated wax embedding system described in FIGS. 11, 12, and 16 is housed within this unit.

Finished paraffin block storage trays are provided in which the system will store finished embedded platforms awaiting sectioning.

Figure 38:
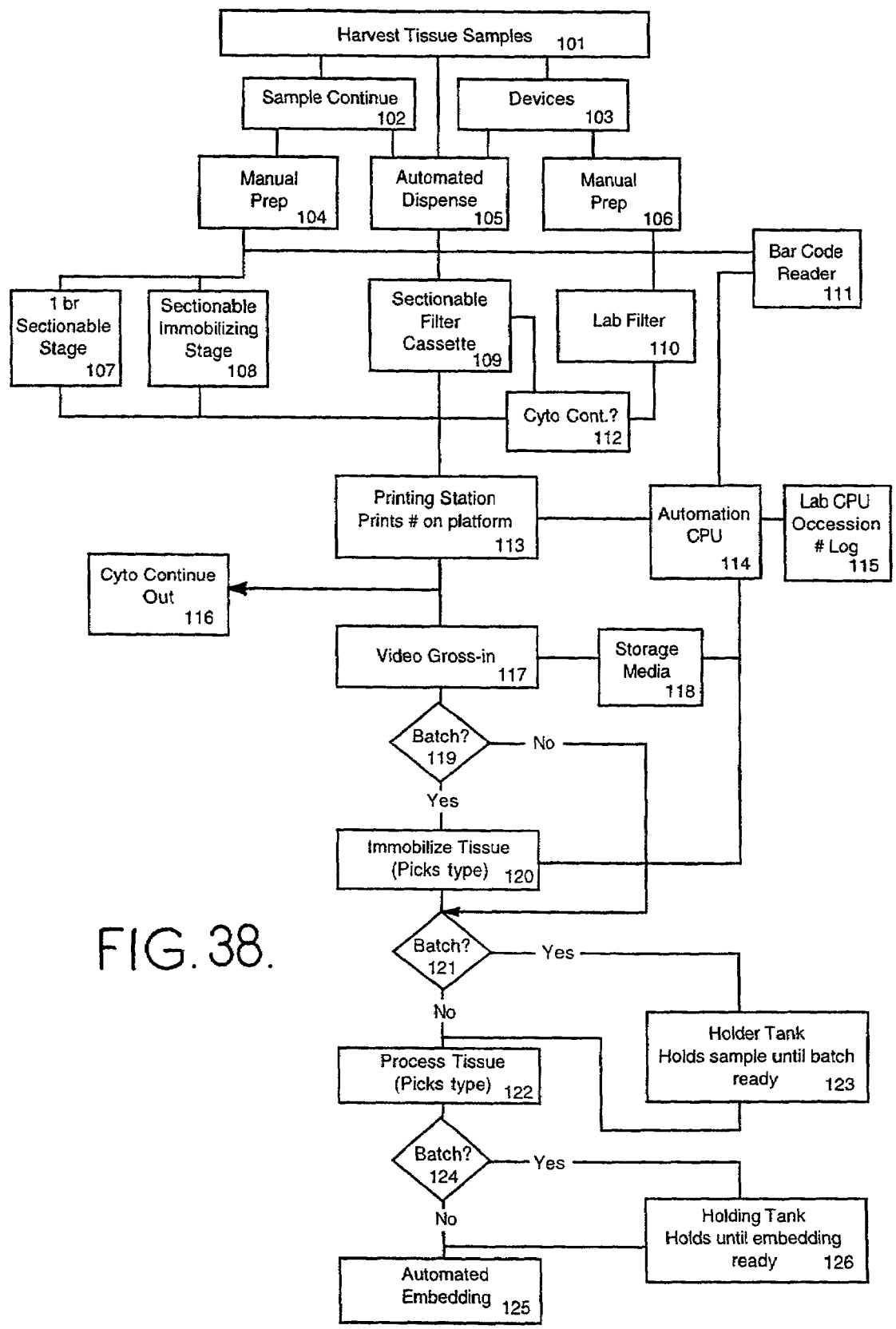

FIG. 38 is a flow diagram depicting the process flow of automated histology sample preparation. Process 101 is tissue harvest. Tissue harvest can be accomplished with any surgical device such as fine needle biopsy aspiration or a surgical biopsy sample device. If appropriate, a tissue sample container can be fed into the automated sample dispensing device. A bar code reader can read any machine readable information on sample containers or devices which will then match up with the laboratory accession number from data base 115. If a cytology sample has been ordered, it is noted in box 112 and a cytospin container is automatically provided to collect the eluate.

In Step 1 other samples are manually loaded onto the appropriate tissue trapping platforms. The printing station 113 then prints the accession number assigned by the automation CPU form accession log data base 115. This is printed both onto the cassette frame and the cytospin container if one was required. The cytospin container is exited from the system in Step 2.

Automated gross in 117 is performed and the information is stored on storage media 118. Decision process 119 determines whether further immobilization of the sample is required. For example, sectionable immobilization stages which have been manually prepared will not require application of additional immobilization techniques. A machine readable feature on the stage determines whether the immobilization station should be bypassed or not. If immobilizing is required, the platform is treated with the appropriate technique at box 120.

After immobilization, the platforms are held in batch in a process holding tank awaiting tissue processing or are sent continuously through the processor. Step 4 is tissue processing which relies on standard prior art technology.

After processing another decision block determines whether the platforms will be held for batch wax embedding or will be embedded as available from the processor. Step 5, box 125 is the automated wax embedding process.

Tissue Specimen Container with Integral Sectionable Filter

The object of the container embodiment (shown in FIGS. 19, 20, 21 and 22) is to provide a simple and easy convenient way to place tissue samples on the sectionable filter; to detachably hold the sectionable filter in place on the container while depositing the samples, to retain the samples on the sectionable filter, to keep the sample wetted with fixative and to provide a convenient way to remove the sectionable filter and sample from the container without leaving behind any useful samples.

In general, one form of a tissue sample container 200 is shown in FIGS. 19–22 and includes: apparatus supporting histologic tissue biopsy samples which includes a tissue support for supporting tissue samples during tissue—processing, embedding and micotomy and including means for permitting said tissue supporting means to be sucessfully sectioned in a microtome, means for resisting histological stains, means for resisting degradation from solvents and chemicals used to process and stain the tissue, and means for maintaining said tissue supporting means non-distracting during tissue preparation and slide preparation. As above discussed, one form of the invention includes a tissue supporting means that can be successfully sectioned in a microtome, while another form of the invention includes a tissue supporting means that is porous. Specifically, container 200 includes a body 201, a sectionable filter 202, a cap 203, and a gasket 204. An injection site 202' is located adjacent to the filter whereby samples can be placed on the filter. Container body 201 is configured as a wide mouth vessel with concentric flexible release fingers 205 projecting from bottom internal surface 206. These fingers are adapted to detachably engage and retain sectionable filter 202. A small retention ridge 207 on an extending lip of each finger engages the sectionable filter collar or ring 202 to lightly retain the sectionable filter on fingers 205 during tissue placement and transportation. The sectionable filter ring has a corresponding undercut 208 to engage the retention ridge 207 on each finger. The sectionable filter is positioned close to the same height as the container's outer lip 209. This allows samples to be placed or scraped onto the sectionable filter without reaching down into the container. Further, if the sample is being transferred from a long scraping tool is must be able to lie flat on the sectionable filter to transfer the sample. The height of fingers 205 in the container also space the sectionable filter just above the fixative level 210 in the container.

The sectionable filter ring is adapted to have an outer ring 211 and spider ribs 212 (FIGS. 20 and 21) that create a support structure for the filter or screen. It is envisioned that the sectionable filter will be injection molded in a single unit. The ring has an outer edge 211' that is larger in diameter than the inner diameter of the ring to act as a deformable sealing lip which will allow it to create a seal to the inside bore of displacement cylinder 215 in the cap. Screen 213 is molded to provide openings in the 0.006" to 0.008" range. Smaller or larger openings could be manufactured to accommodate the tissue sample sizes desired. The sectionable filter has a small ring 214 that protrudes above the screen surface 213'. Ring 214 allows fluid to be poured through the screen so that it will and not spill over the edge. It is also utilized as a standoff when the sectionable filter is placed in the wax mold to allow any protruding tissue to stand above the screen surface. This prevents any flattening or distortion of the tissue sample prior to wax embedding. It also provides a surface for heat-sealing an immobilizing net (Dry Net) over the tissue samples.

Yet another feature of the container is the fixative fluid displacement apparatus, such as cylinder 215 on cap 203. The cap has an elongated cylinder which extends below attachment section 216 which is shown as threaded, but could take on any of a number of configurations, such as: ¼ turn locking; friction or snap fit. The displacement cylinder 215 acts to raise the fixative level 210 above the sectionable filter 202 inside the container when the cap 203 is installed. FIG. 19 shows a sectional view of the cap and sectionable filter in place raising the level of fixative 210B above the screen upper surface 213' helping to keep the tissue samples wetted during transport. This will help to prevent the samples from becoming dried out and will additionally keep them confined in an area that will strain the fluid contents through the sectionable filter as the cap is removed and the fluid level drops inside the container.

Figure 21:
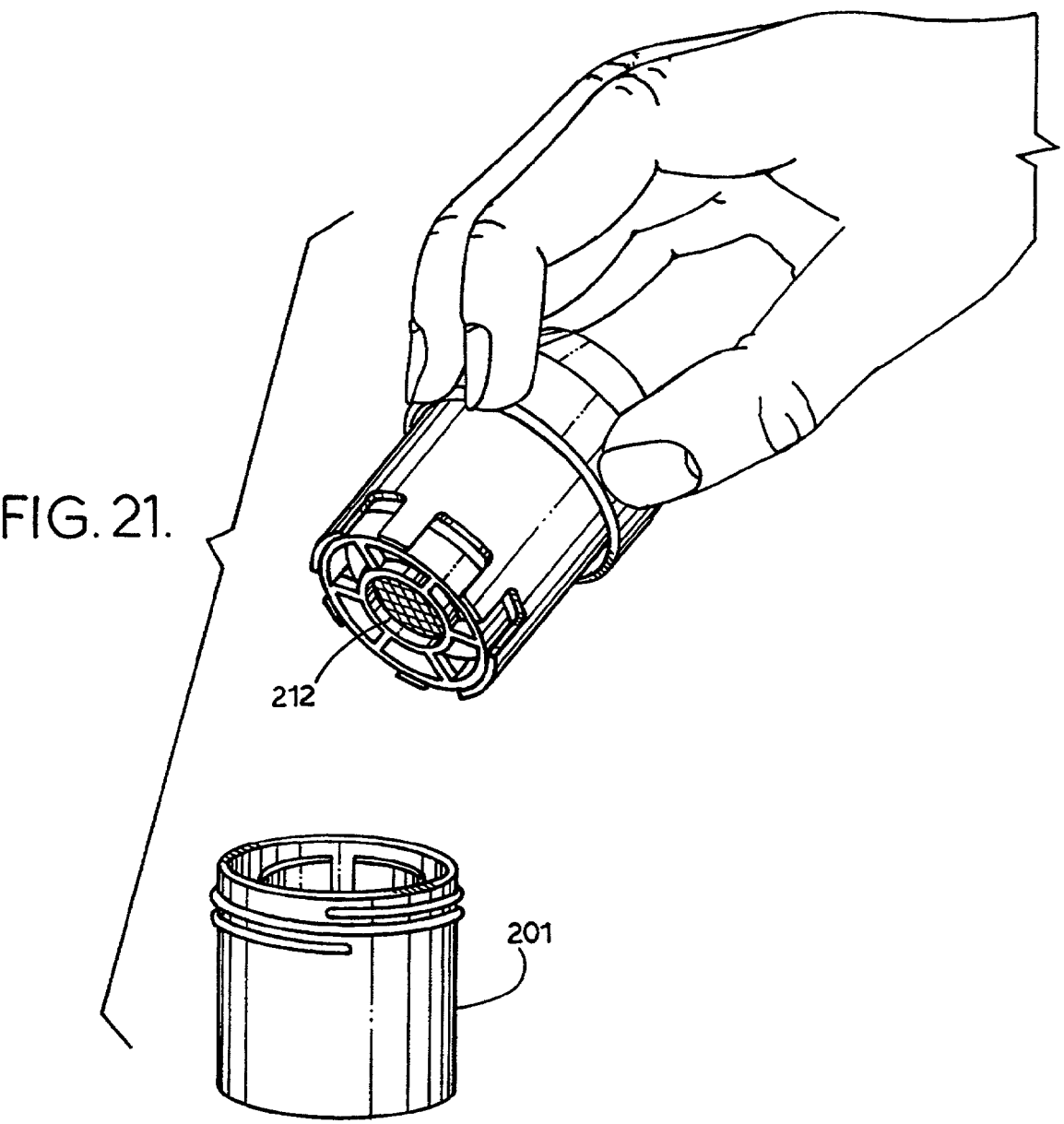
Figure 22:
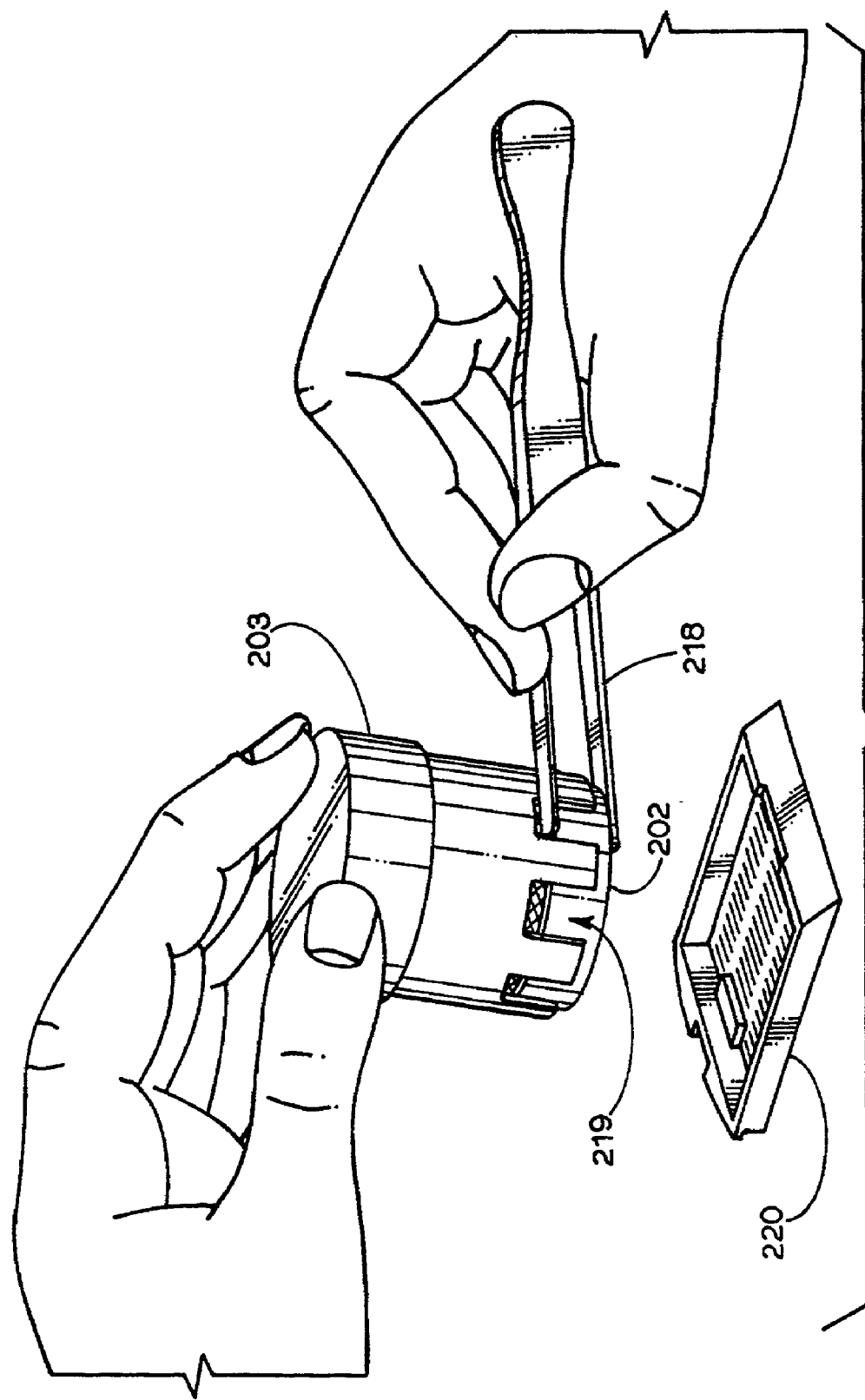

To facilitate the removal of the sectionable filter from the container, retention ridges 207 on fingers 205 and grooves 217 are fashioned on the inside diameter of displacement cylinder 215. As shown in FIGS. 20 and 21, as the cap is lifted up (FIG. 21) grooves 217 engage outer sealing edge 211 of sectionable filter 202 transferring it from container 201 to cap 203. Fixative level 210 will drop as the displacement ring is withdrawn from the container straining the tissue fragments through the sectionable filter. Sectionable filter 202 can be removed from the cap by placing forceps 218 (FIG. 22) into cutouts 219 in the displacement ring and disengaging it from the cap. The sectionable filter with tissue samples are then placed into either a standard prior art tissue cassette 220 for non-automated processing, or into a specialized filter cassette frame for automated processing as discussed above.

Alternately the displacement cylinder would have no grooves to engage the sectionable filter. This would be necessary case one wants to inspect the filtered contents before removing the sectionable filter from the container. In that case, it is envisioned that the sectionable filter would reside above the lip of the container to facilitate access to the edge of the sectionable filter with forceps for easy removal of the sectionable filter. The cap would retain the fixative displacement ring but would not include the retaining grooves.

Fine Needle Aspiration Biopsy Device.

In general, the invention includes a tissue sample container comprising: a means for supporting histologic tissue biopsy samples which includes a tissue support for supporting tissue samples during tissue processing and embedding and micotomy including, means for permitting the tissue supporting means to be successfully sectioned in a microtome, means for resisting histological stains, means for resisting degredation from solvents and chemicals used to process and stain the tissue, and means for maintaining the tissue supporting means non-distracting during tissue preparation and slide preparation. As before, one form of the invention includes the tissue supporting means being porous as well.

Figure 25:
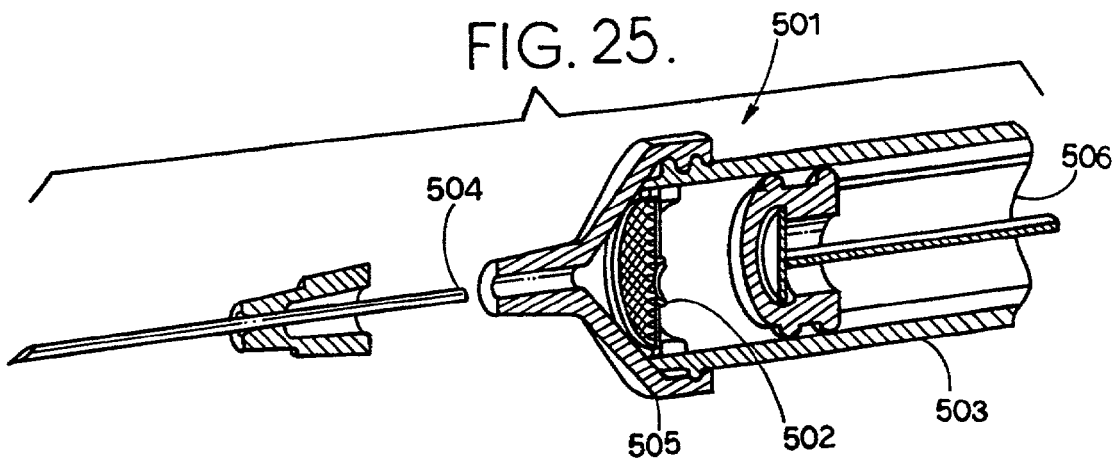

FIG. 25 depicts a fine needle aspiration device 501, with an integral tissue trapping sectionable filter 502. The sectionable filter is positioned within the body of the syringe 503, opposite the proximal end of fine needle 504. This allows the physician to take the sample by prior known procedure but assures that larger tissue samples will be retained by the filter in preparation for histologic cell block preparation. Retaining cap 505 is threaded for easy removal. This allows for removal of the filter by unscrewing the retaining cap and pushing plunger 506 forward to eject the filter. In addition, the physician can elect to prepare a direct smear on a glass slide by first taking the biopsy then aspirating any fine cellular particles out onto a glass slide.

Figure 26:
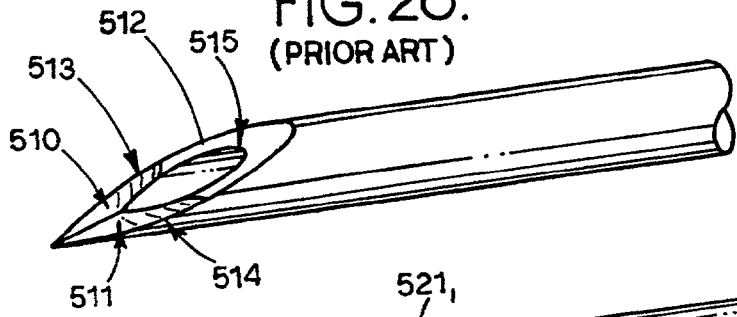

In order to provide tissue specimens for histologic exam one must first obtain sufficient quantity and size from the biopsy. As prior art has shown many attempts have been made at providing fine needle aspiration biopsy needle configurations that provide improved sample harvesting properties. Yet in most cases physicians continue to use standard three bevel grind venipuncture needles such as is shown in FIG. 26, most likely due to their low cost and accessibility. However, pathologists have noted that there is a high incidence of insufficient or poor quality samples obtained by the standard venipuncture needle.

Figure 27:
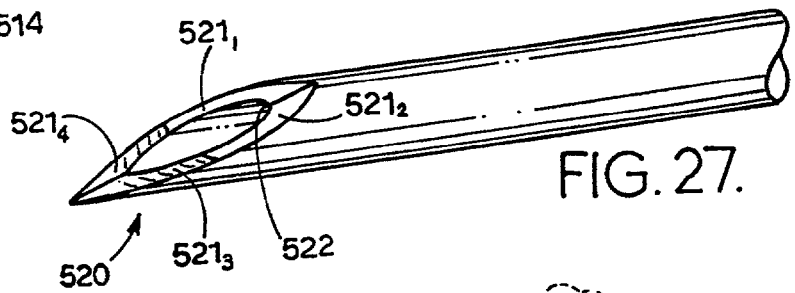
Figure 28:
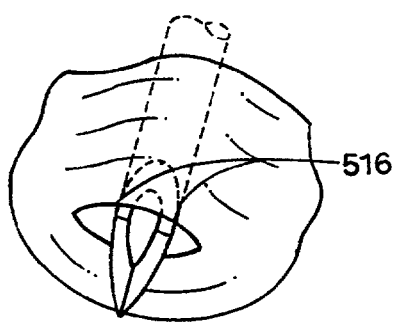
Figure 29:
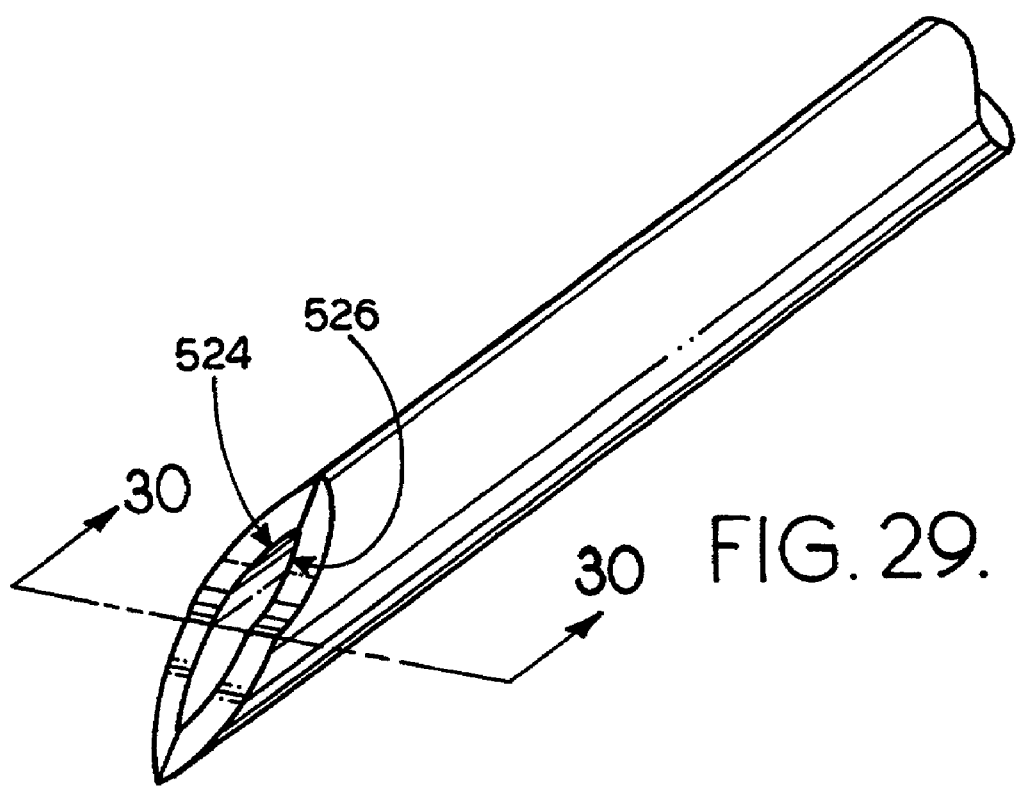
Figure 30:
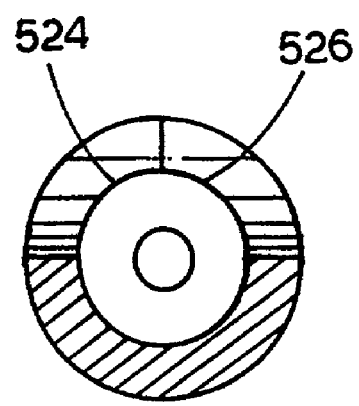

If one looks at a venipuncture needle tip under magnification, it will be found that the tip has three flat faces 510, 511, 512, two of which 510, 511 create the sharp tip and a third 512 which is transverse to the axis at a very acute angle usually 18–20 degrees. The two tip bevels are very finely ground and produce exceptionally sharp edges 513, 514 that part the tissue on insertion. Third surface 512 is less fine and in fact has one serious flaw that creates problems for the cutting of biopsy samples. Edge 515 which is created from the inside bore and the third surface is not well controlled and most often is found to have been treated by an abrasive grit blast to de-burr the edge. For venipuncture this is advantageous since it is not desirable to cut holes in a blood vessel which would cause trauma and bleeding. But when it is desired to take tissue samples, it produces poor and unpredictable results. It might be assumed that just honing the third surface to produce a fine sharp edge would produce better results, and while this is partially true, the inventors have discovered that the tissue tends to "tent" upon passage through tissue. FIG. 28 shows the outer edges of the prior art needle 516 creating "tent poles" stretching the tissue taught between edges 516. This prevents the tissue from contacting internal edge 515 even if it is sharp. The present invention overcomes this limitation by including a four bevel grind 520 shown in FIG. 27 with areas $521_1$, $521_2$, $521_3$, and $521_4$ which in effect moves sharp tissue severing edge 522 to the outside or top of the tent. FIGS. 29 and 30 show the two new edges 524 and 526 that are created from the inside bore of the needle where they intersect the two new flats. This configuration cuts well and provides adequate tissue samples for histological exam.

Figure 33:
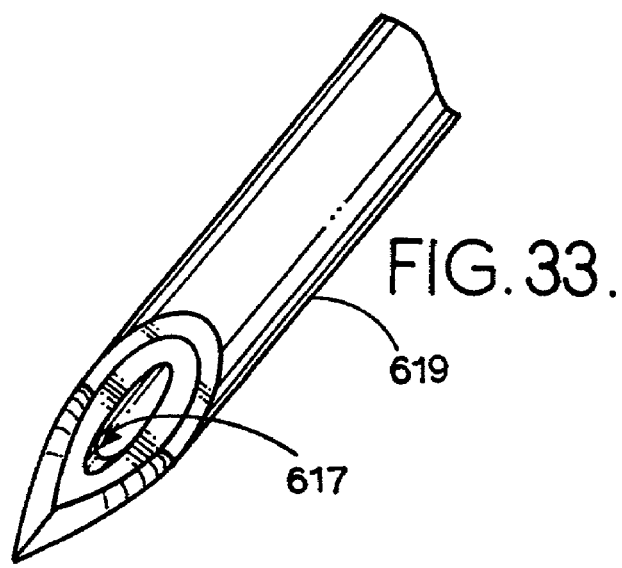

When creating a design for FNAB, it must be kept in mind that although standard venipuncture needles are less than optimal, they are inexpensive. Therefore, it is desirable to make the FNAB needle of the present invention inexpensive to manufacture. The four bevel grind is relatively inexpensive to manufacture. However, it is very aggressive and cuts on the entry stroke. The entry stroke leads to tissue samples from the path to the target site in addition to the target. Another configuration allows for sampling on the removal stroke. FIGS. 32 and 33 disclose a back-eye 617 which is cut through the needle 619 directly opposite the bevels. This can be manufactured by drilling or EDM machining. The eye 617 is cut at a severe angle (18–20 degrees) back towards the proximal end to produce a sharp cutting edge 618 at the needle's outside periphery. This needle can be inserted to the proper depth and then stroked in and out while applying suction from the syringe to harvest the samples. The suction has been shown to increase the quantity of samples retrieved, so it is believed to bring the tissue in closer approximation to the sharp cutting edge.

In yet another improvement the inventors have discovered that any ledges or interstices in a syringe will create traps where the tissue samples may become lodged and therefore become trapped and not retrieved from the device for examination. One such area in the standard needle and syringe is the luer fitting. A prior art needle NP is shown in FIG. 31A and has a ledge L formed at the exit of the proximal end of needle tubing TP in front of tip T of male luer fitting MP on the syringe. This ledge often traps small tissue fragments as indicated in FIG. 31A. The inventors have designed their needles 620 to protrude all the way up the central bore 621 of the luer fittings eliminating this tissue trapping ledge. This can be understood by comparing FIGS. 31A and 31. As shown in FIG. 31A, the adapter MP has an entrance/exit location E formed by the intersection of the inner surface SI of sidewall S and the inner surface MPI of luer adapeter fitting MP. The inventors have extended tubing TP so that the proximal end thereof lies in a place containing intersection E.

In still another way to implement the sectionable filter technology there is provided an improved tissue harvesting fine needle such as the ones described above, but which deletes the sectionable filter in the syringe body. This then allows the physician to use a better method of ensuring complete capture of the harvested biopsy samples. Since many times the physician will request cell cytology and cell block preparation for histology, it must be assured that all sample material is collected and preserved in fixative immediately after harvest.

Figure 34:
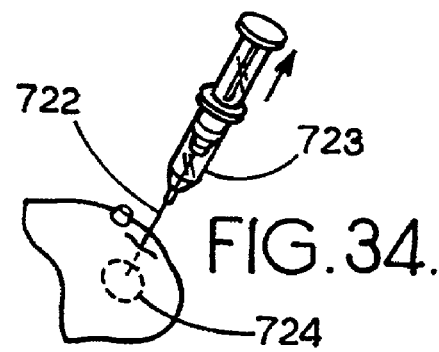
Figure 35:
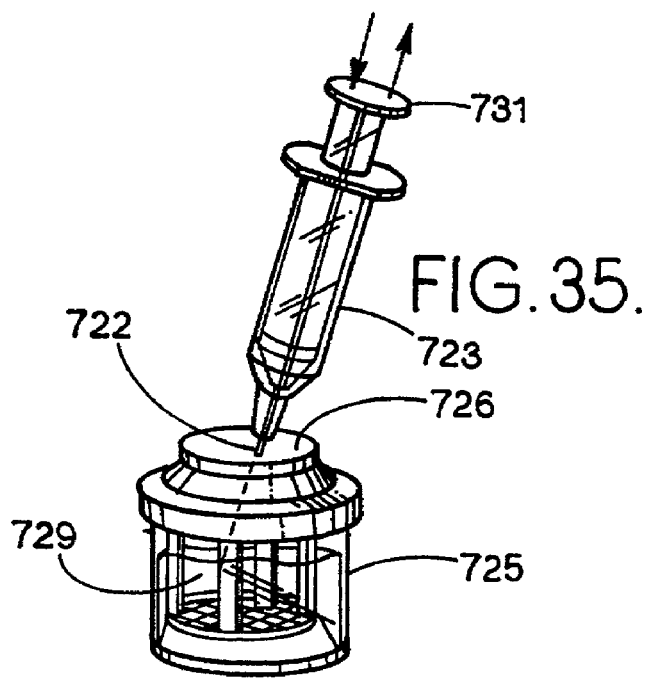
Figure 36:
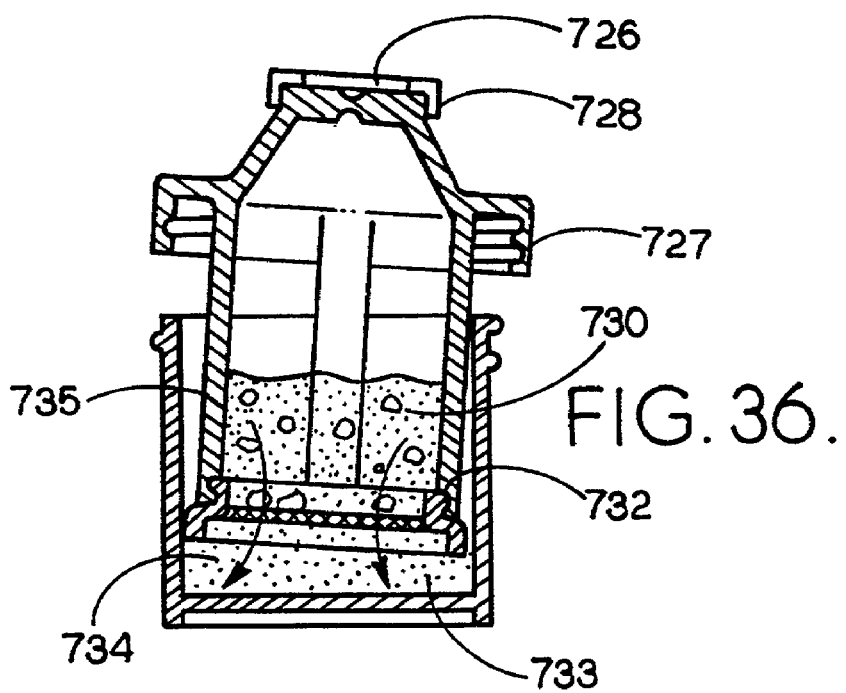
Figure 37:
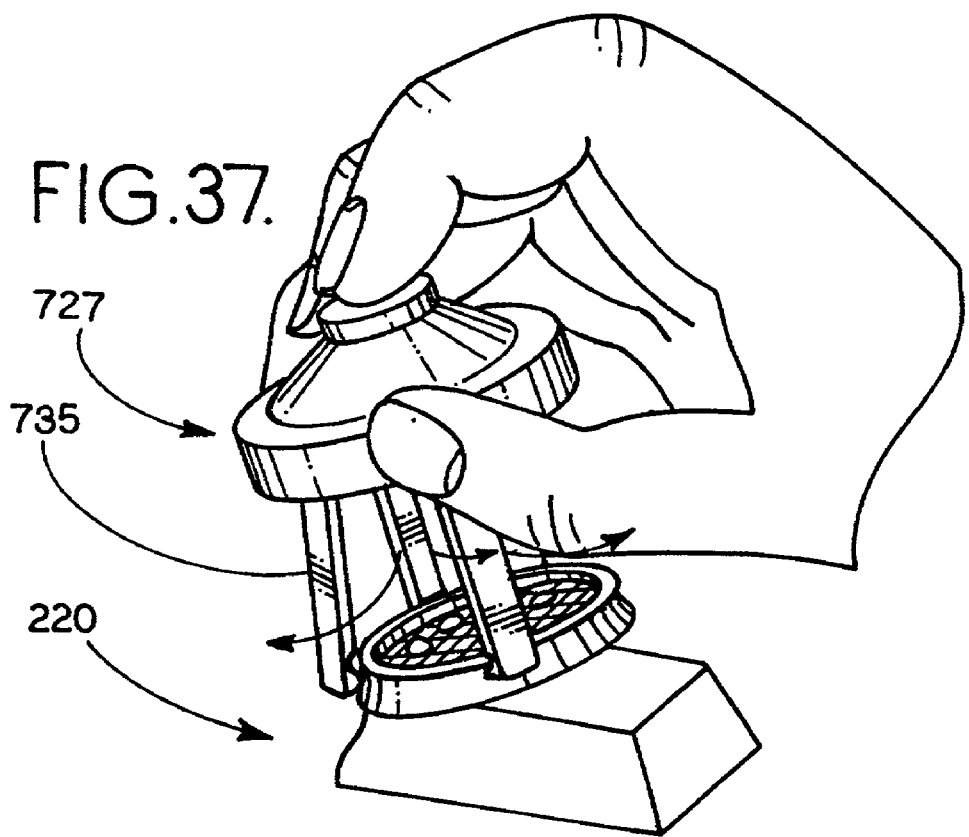

FIGS. 35, 36 and 37 disclose an improved container that provides this advantage. Syringe 723 and special needle 722 are used to obtain the samples of target lesion 724 by prior art techniques (FIG. 34) and are then used for introducing tissue specimens into a container 725. A fine 20: needle aspiration device can also be used in place of syringe 723. Syringe needle 722 is then inserted into special container 725 through an injection port 726 in the cap 727 of the container, here cap 727 is molded of an elastomeric material which allows for an integral injection port 726 to be included in the cap. The cap has a metal ring 728 which imparts a compressive force on the injection site to keep it from leaking when the needle is removed. Fixative solution 729 is sucked into the syringe body which flushes harvested biopsy samples 730 into the bore of the syringe. Plunger 731 is depressed and the fixative and samples are then transferred into sectionable filter container 725. This procedure can be repeated as necessary to dislodge any samples. The needle is removed from the injection site and the syringe and needle are discarded. The biopsy samples can now be transported to the histology lab for preparation. Another feature of the system involves the removing of sectionable filter 732 which strains the fixative 733 solution through sectionable filter 732 leaving larger samples 730 on the sectionable filter for cell block preparation and allowing smaller cells 734 to pass through the sectionable filter. These smaller cells can then be processed as a cytospin cytologic preparation. Still further, FIG. 37 depicts cap, 727' fashioned from an elastomeric material, which can be flexed in the correct way to move retaining legs 735 which hold the edge of sectionable filter 732, outwardly to release the sectionable filter from the cap. This allows the histotechnologist to deposit the sectionable filter and samples into the standard prior art tissue cassette 220 with one hand.

Since this sectionable filter fits into the smallest inner dimension of the wax mold form, it is not necessary for this particular platform to have the vertically translatable sample surface feature of the inventive filter cassette frame. When the sectionable filter is removed from the cassette frame and placed into the wax mold form, the sample surface will be automatically oriented in the sectioning plane close to the sectioning surface of the wax mold.

Surgical Biopsy Devices with Sectionable Filter

FIG. 23 depicts a surgical biopsy device 800 which uses a tissue support, such as the above-discussed sectionable filter to trap and transport tissue samples from the surgical suite to the pathology laboratory. Surgical biopsy device 800 includes a device handle 802 and a hollow shaft 804 and biopsy jaws 806 with an integral filter housing 808. Biopsy jaws 806 can take the form of any number of biopsy jaw configurations.

Shaft 804 which connects handle 802 to jaws 806 actuates the biopsy jaws and allows for a hollow central channel to transport the biopsy sample from the patient's body at the biopsy jaws to the filter surface where it is trapped. Filter assembly 810 is shown in FIG. 24 and contains sectionable filter 812. The filter assembly is installed in a filter housing 814 which is a transparent housing so that the surgeon can visualize when tissue has deposited on the filter.

A suction trigger 816 couples to a suction port 818 for controlling suction, with the port 818 being a source of suction for device 800. When the suction trigger is pulled back, the suction port opens. When the suction port is connected to a vacuum source 819 the suction is coupled through the filter and hollow shaft to the biopsy jaws. This transports any loosened tissue pieces from the biopsy jaws back to and trapping them in the filter. Any fluid that is suctioned into the hollow shaft will pass through filter 820 into the filter housing and out through the suction port. Once the sample has been deposited on the filter, the filter housing is rotated up and opened. The surgeon can then remove valve cap 822 and the filter (the filter assembly) from the filter housing. This filter assembly is placed into a container for transport to the pathology laboratory. Another filter assembly can be inserted into the filter housing to collect more samples. The valve cap has a one-way valve, such as duck bill valve 824, preferably made of silicone, which allows for one way passage of suction from the biopsy jaws onto the filter. Once the filter assembly is placed into the container for transport, the contents of the container cannot leak out through the one way valve.

Sectionable Filter adapted for histological laboratory use and manual loading.

Figure 39:
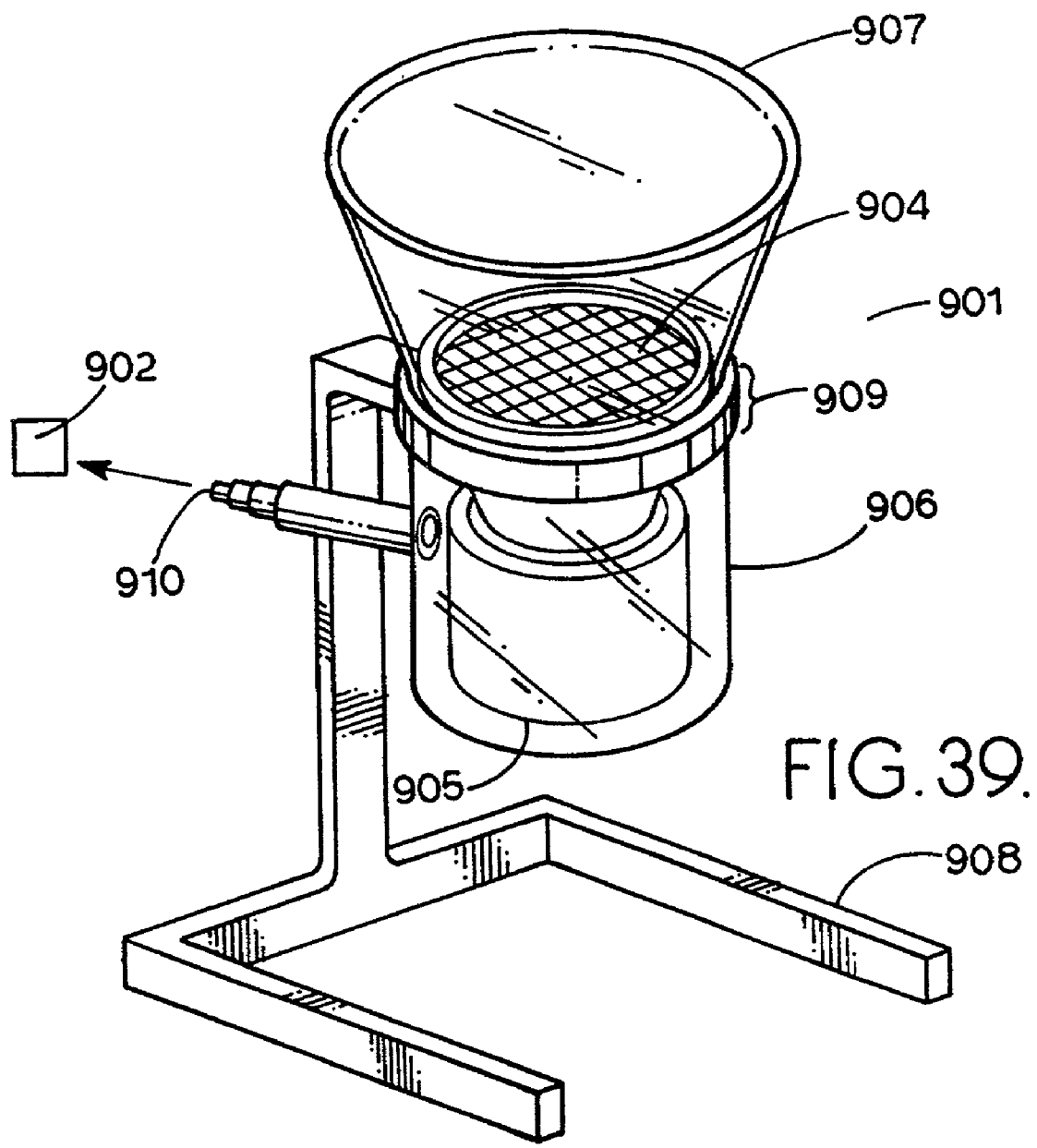
Figure 40:
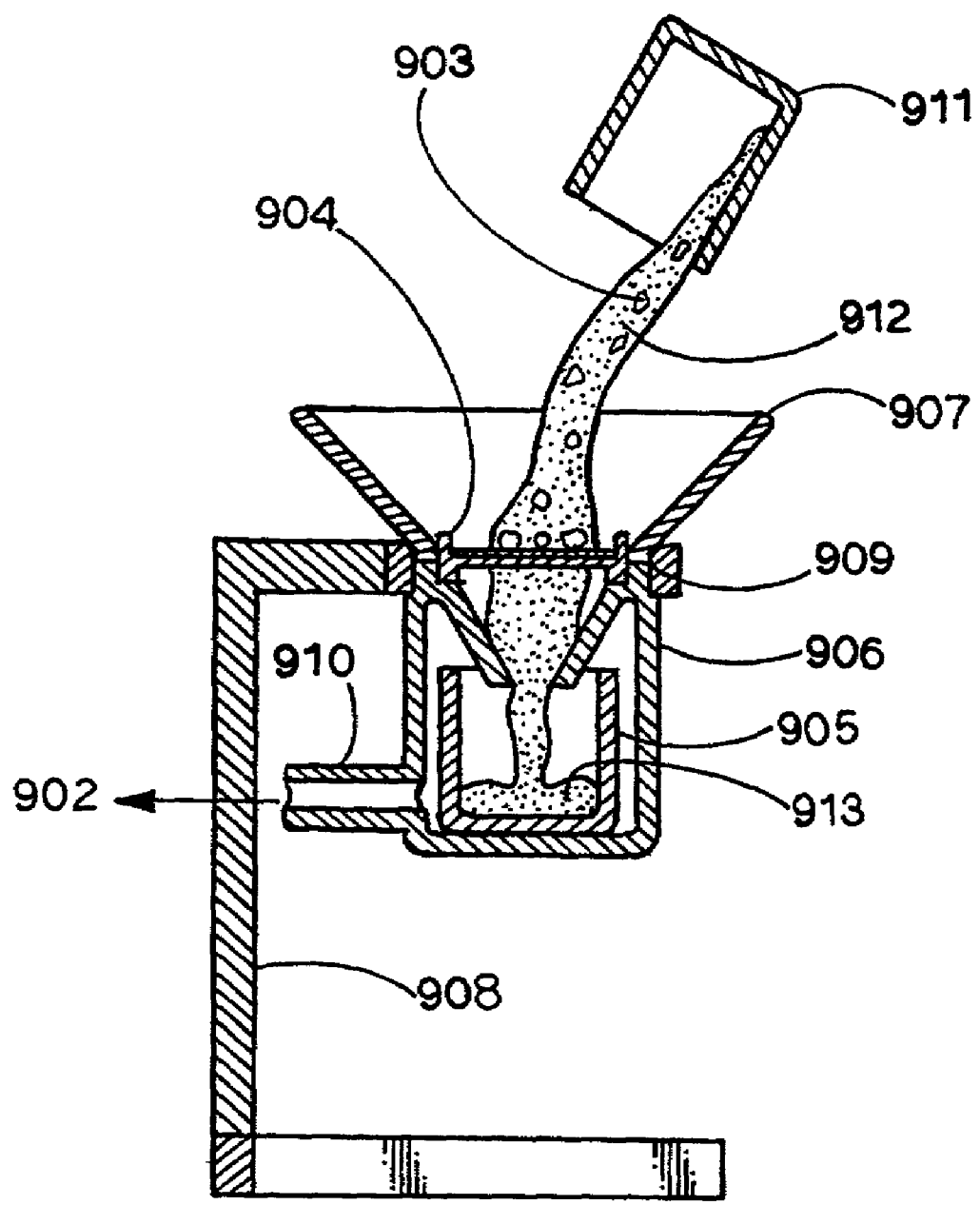
Figure 41:
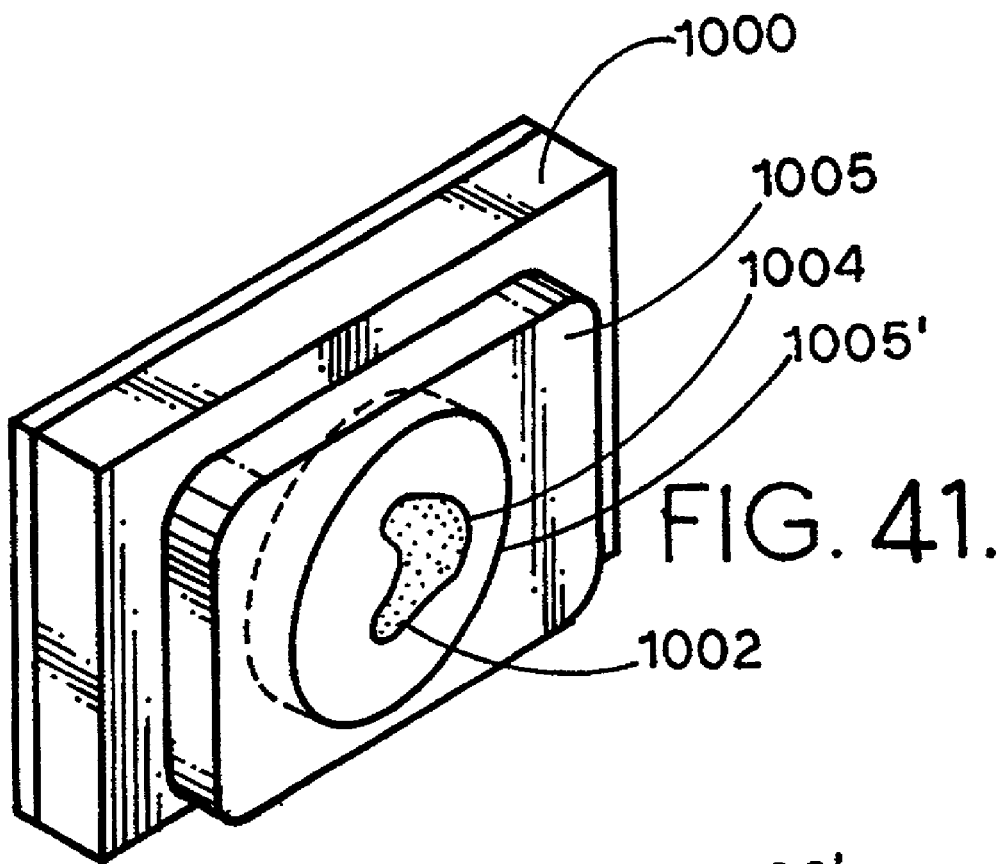

Additional uses for the sectionable filter are shown in FIGS. 39 and 40, whereby the filter is used in the pathology lab to separate tissue samples from the fixative or body fluids which may come to the lab from any number of sources. This adapted sectionable filter can be configured identically to the ones integral to the biopsy collection container and used in conjunction with a standard prior art tissue cassette frame, or could be configured as a sectionable filter cassette in a stage cassette frame (rectangular version). Currently, these small tissue samples in fixative are separated using a "tea bag" filter which separates the fluid from small tissue fragments. The tea bag then goes into the tissue cassette and the processor. When removed from the processor, the tissue fragments have become dried and are usually adhered to the tea bag, which requires scraping them loose and further manipulation to get them placed into the paraffin mold form.

The sectionable lab filter or cassette configuration as shown in FIGS. 39 and 40 is be adapted for use with a suction device 902 that can draw the fluid through the filter quickly leaving tissue fragments 903 in filter 904 for cell block processing. The effluent could also be trapped in a cytospin container 905 inside the vacuum chamber 906 to make a cytospin cytologic preparation.

FIG. 40 shows a sectional view of laboratory device 901 described above. Funnel 907 is attached to the instrument stand 908 and is adapted for placement of a sectionable filter 904 or the cassette configuration in the central bore. Suction container 906 below the filter is threaded at 909 for attachment to the stand, a vacuum fitting 910 is in communication with the inside of vacuum container 906. In use, a biopsy sample arrives in a transport container 911 in fixative solution. The cap is removed from the container and solution 912 is dispensed into funnel 907. Large samples 903 and small samples 913 are strained through sectionable filter 904 or sectionable filter cassette 904. Vacuum 902 may be applied at this stage to speed up the process. The solution with smaller fragments 913 passes through the filter and can be collected in a cytospin container 905 below the sectionable filter. The sectionable filter or sectionable filter cassette is removed from the lab device and processed in a manner described herein.

Sectioned Paraffin Block

In general, the finished product is a sample of a tissue for analysis comprising: means for supporting histologic tissue biopsy samples including a microtome sectionable tissue supporting means for supporting tissue samples during tissue processing, embedding and microtomy including means for permitting said tissue supporting means to be successfully sectioned in a microtome, means for resisting histological stains, means for resisting degredation from solvents and chemicals used to process and stain the tissue, and means for maintaining the tissue supporting means non-distracting during tissue preparation and slide preparation;

and a supporting surface for supporting the sample for microscopic examination. One form of the invention includes a porous tissue supporting means.

Figure 42:
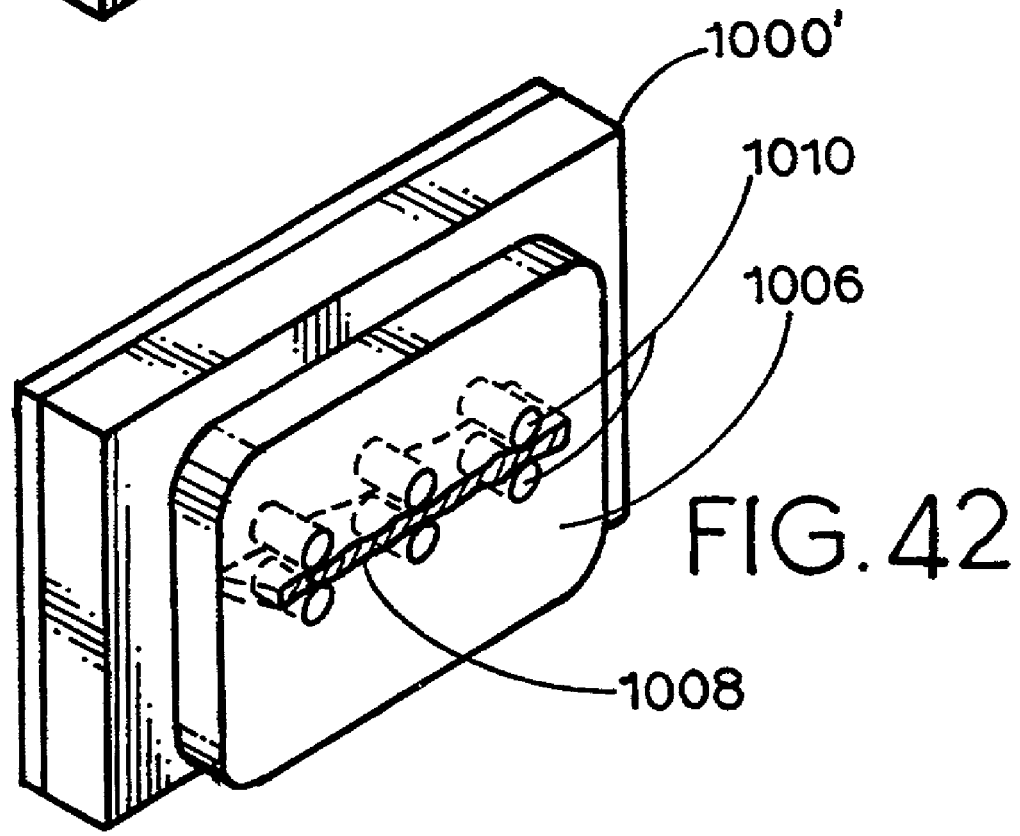

A finished product is specifically illustrated in FIGS. 41–46. Thus, in FIG. 41, a finished cassette 1000 has a tissue 1002 and tissue support 1004 and 1005' embedded in wax 1005; while FIG. 42 shows a cassette 1000' which has wax 1006 embedding a tissue 1008 held on pegs or posts 1010 in a manner similar to that indicated in FIG. 3.

Figure 43:
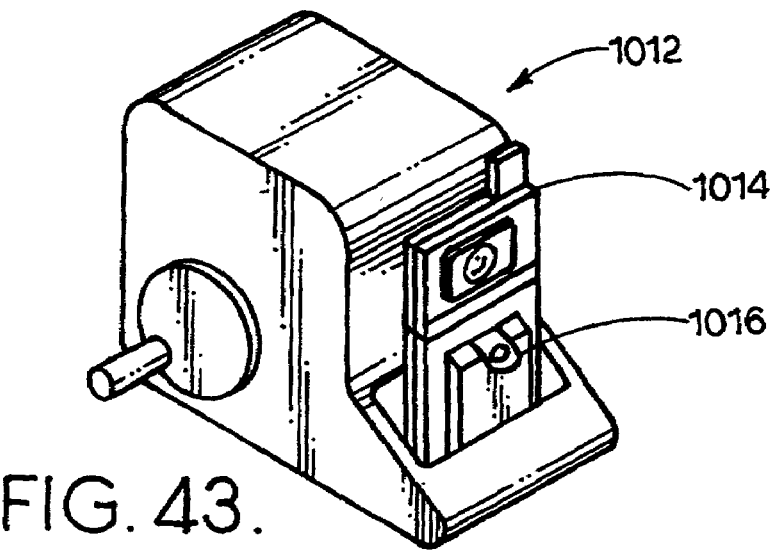
Figure 44:
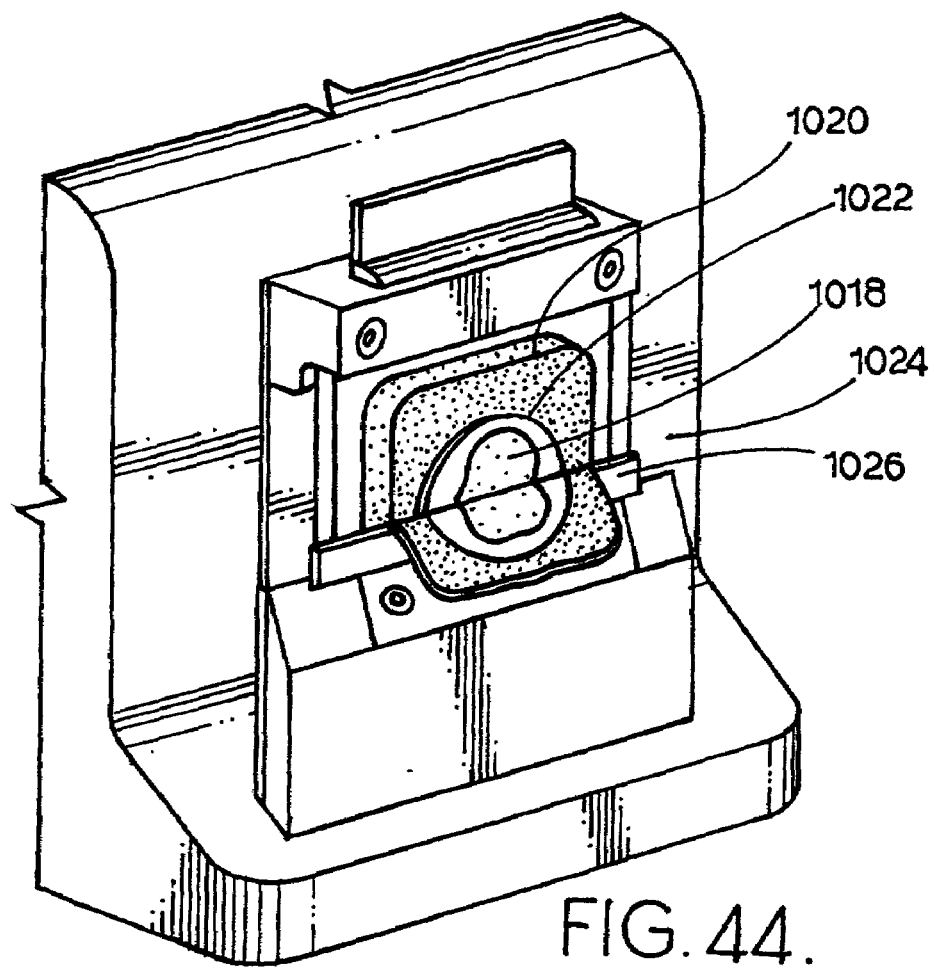
Figure 45:
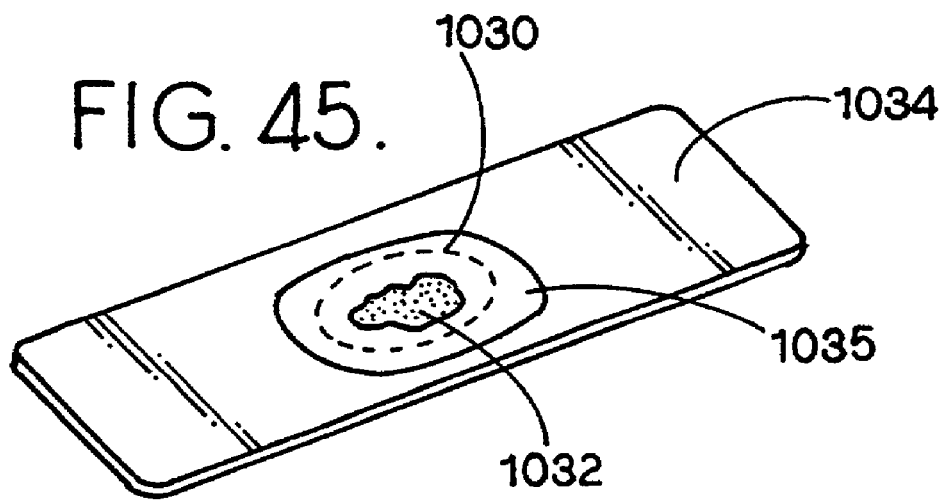
Figure 46:
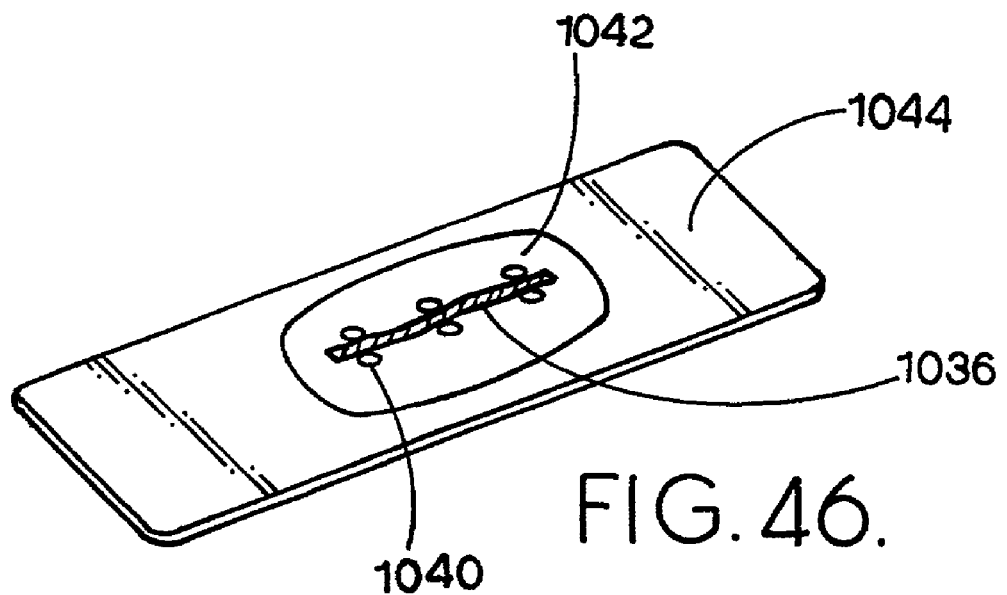

Slicing the wax embedded tissue and tissue support (filter) is indicated in FIGS. 43 and 44. It is emphasized that the filter material is sectioned in the microtome along with the wax and the tissue sample. Thus, in FIG. 43, a microtome 1012 has a cassette 1014 thereon with a tissue specimen indicated at 1016. A further view is shown in FIG. 44 with tissue being indicated at 1018, wax at 1020, filter material (tissue supporting material) at 1022 and the cassette being indicated at 1024. The microtome blade is indicated at 1026 as it slices the wax/tissue/filter combination. A mounted specimen is shown in FIG. 45 with the sliced filter being shown at 1030 and the sliced tissue specimen being shown at 1032 and the mounting slide being shown at 1034. Wax is indicated at 1035. A tissue specimen 1036 is shown in FIG. 46 with holding posts 1040 and wax 1042 on a support, such as slide 1044, for supporting the sample for microscopic examination.

In summary, some of the components and advantages of the present invention include the following.

1. The invention of tissue trapping filters or stages including those that are microtome sectionable or not and those that act as filters as well as those that act as immobilizing stages; all can have a vertically translatable sample surface within a cassette frame which facilitates sample loading, confers protection from crushing of the tissue samples during the processing steps and allows the sample surface to be pushed into the wax mold; use of the tissue trapping platforms (filter or stage in combination with a cassette frame) allows the tissue processing and wax embedding procedures to be automated.

2. An immobilization process, whereby the tissue is secured to a filter or stage by various apparatus (Dry Net, Ballistic Net, etc.) allowing it to be properly oriented for sectioning at the initial gross in, which eliminates the need for further handling of the samples during tissue processing and wax embedding and therefore makes automation of these processes possible.

3. Proper orientation of tissue samples is assured throughout the process.

4. The invention of sample trapping containers which contain a sectionable filter and help to preserve the quality of the sample from collection to gross in and again reduce the amount of handling required for the samples.

5. The invention of a Fine Needle Aspiration Device and needle configurations which can be used with the sectionable filter;

6. The invention of a surgical biopsy device with integral tissue trapping sectionable filter.

7. The automation of the gross in procedure.

8. The automation of the tissue processing and wax embedding processes together.

9. The automation of the dispensing of Fine Needle Aspiration Biopsy as well as mucosal scrapings, endometrial curettes, bristle brush scrapings etc., with collection of larger tissue pieces onto a sectionable filter and if desired the collection of eluate into a cytospin container for cytology.

10. A method for conducting tests on histology tissue biopsy samples comprising: removing a tissue sample from a patient; placing the tissue sample onto a support, which can be microtomable if desired and which can, in one form of the invention, be porous; immobilizing the tissue sample on the support; subjecting both the support and the tissue sample immobilized thereon to a process for replacing tissue fluid with wax and impregnating the tissue sample with wax, embedding the tissue sample in a wax mold to form a solid block of wax, using a microtome, slicing the solid block of wax into thin slices; and mounting at least one of the thin slices on a support member for examination. If the tissue support is microtomable, then this element, along with the tissue sample, can be embedded in the wax, and both the sample and the support can be sliced by the microtome when the microtome slices the block of wax.

By way of example, the above-discussed methods of obtaining tissue samples is repeated herein along with the preferred form of tissue support:

Fine Needle Aspiration Biopsy—very small pieces of tissue taken from the core of a fine needle; usually transported in fixative solution; decant off fixative solution through a sectionable filter (180 µm filter);

GI biopsy—characterized by a few small tissue pieces; it is desirable to concentrate the tissue pieces in close proximity to each other—decant off fixative solution through a sectionable filter (¼ mm filter);

Prostate chips—orientation is irrelevant for these samples—sectionable filter (1 mm filter);

Endometrial Curettings—characterized by varying size samples; orientation is irrelevant—sectionable immobilization stage (½ mm filter);

Vessel—orientation is critical; sections need to be transverse—sectionable immobilizing stage—manually position over vertical pegs;

Core Biopsy—i.e. from the prostate—orientation is critical; the tissue should lie flat all in the same plane—sectionable immobilization stage;

Gall bladder—orientation is critical—the tissue should be embedded on edge—sectionable immobilization stage;

Uterine Wall, breast or large tumors—orientation is not critical—sample lies flat in a plane—non-sectionable stage.

As discussed above, the cassette is subject to heat and chemicals during the tissue processing. Such heat and chemicals can cause the cassette to change shape. In order to accommodate the changing size of a cassette during tissue processing, a cassette frame interface can be used which accommodates the cassette in both the swelled and the un-swelled configurations. In the unsewelled configuration, the cassette has extra room to move around inside the frame. However, as the cassette grows from heat and exposure to chemicals, its size changes due to swelling.

Still further, as discussed above, it is an object of the present invention to provide a histologic tissue biopsy sample support comprising a microtome sectionable tissue support for supporting tissue samples during tissue processing, embedding and microtomy including means for permitting said tissue supporting means to be successfully sectioned in a microtome, means for resisting histological stains, means for resisting degradation from solvents and chemicals used to fix, process and stain the tissue and means for maintaining said tissue supporting means non-distracting during tissue processing and slide preparation. The above-discussed means achieves this object. However, to achieve this object as well as the just-stated object of accommodating a changing size, the present invention also teaches additional cassettes. These additional cassettes achieve the just-stated objective as well as for cassettes that can accommodate changing shapes as well as including means for resisting chemicals used in replacing tissue fluids with wax, and means for resisting molten wax used to embed the tissue sample and a low density thermoplastic material. The means discussed above in relation 35' to these functions also applies to the following disclosure as well.

Figure 47:
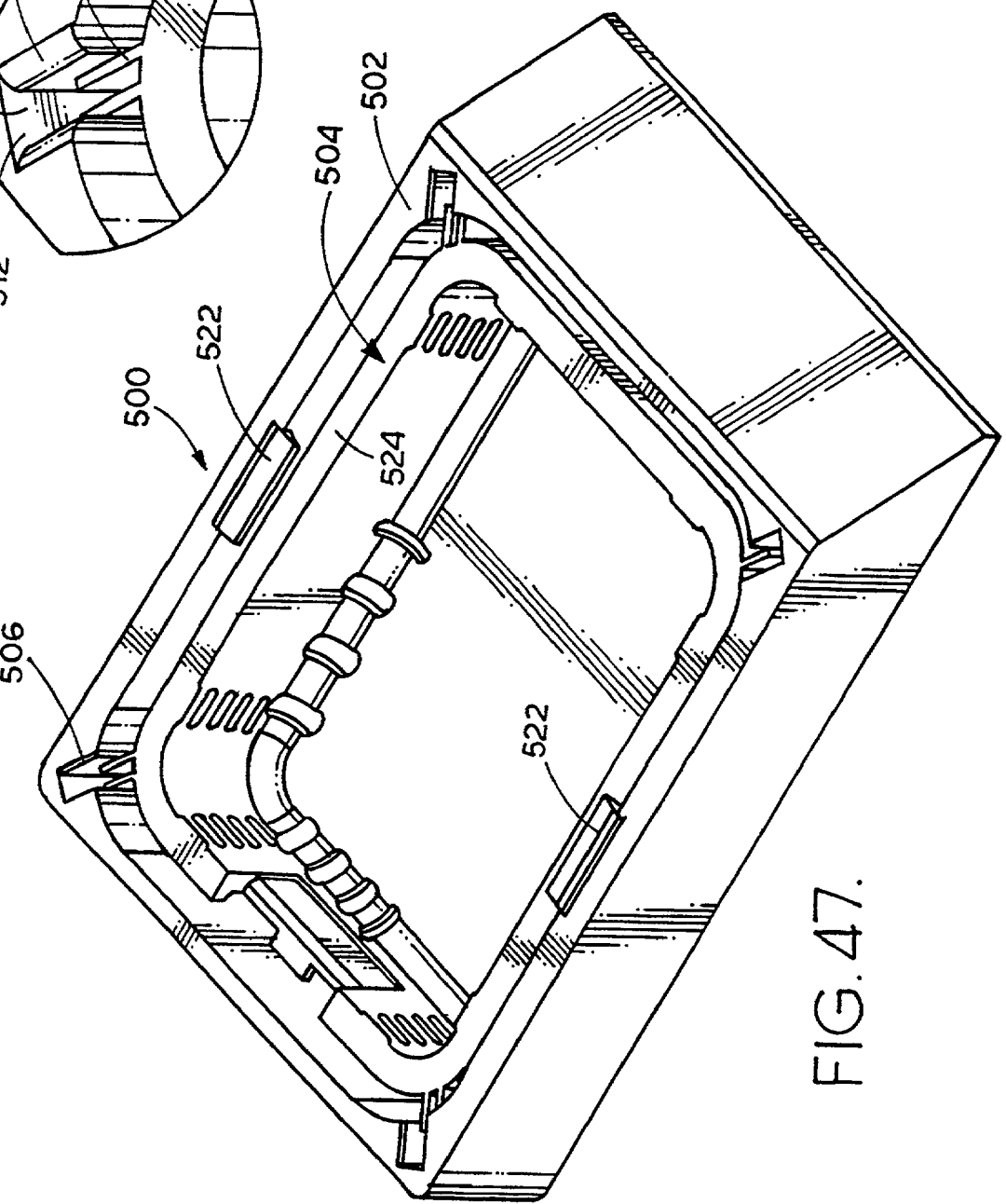
Figure 49:
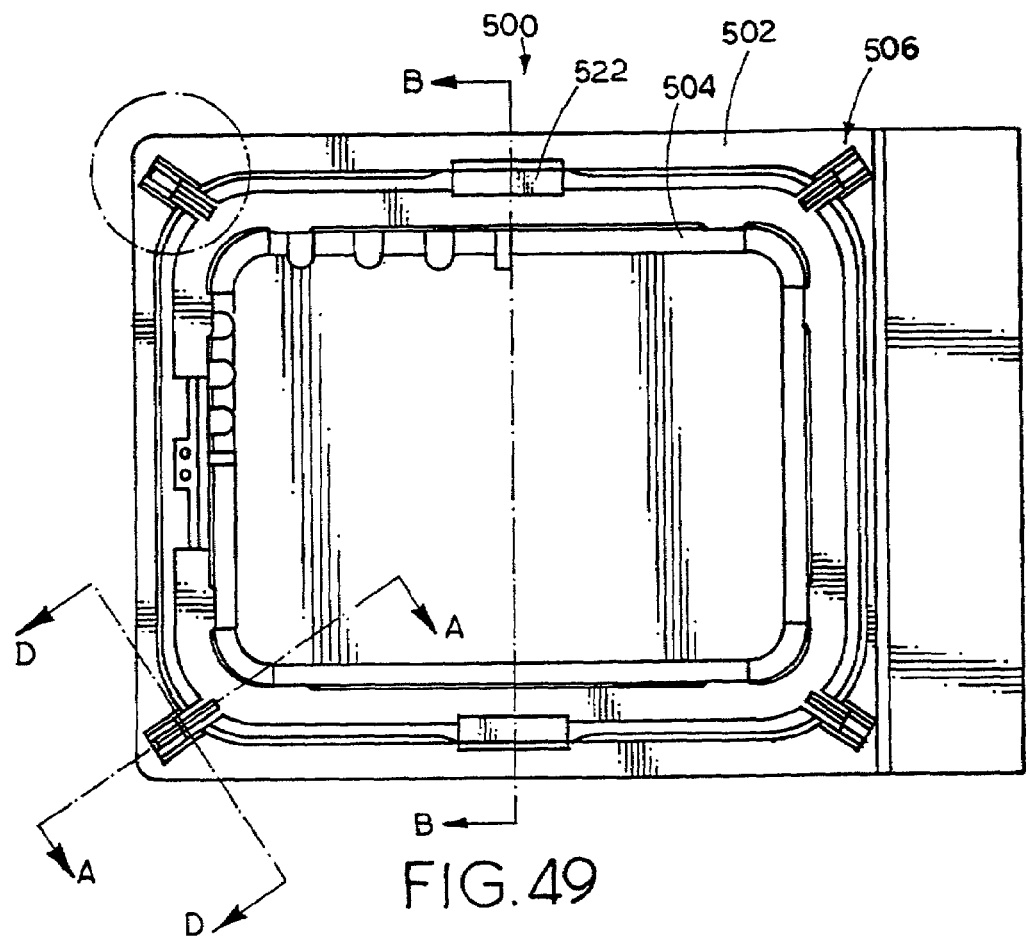
Figure 51:
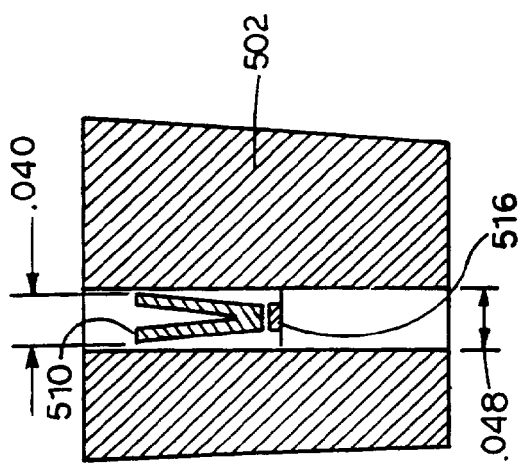

Shown in FIG. 47 is a tissue biopsy sample holding unit 500 which includes a universal frame 502 which releasably holds a sectionable cassette 504. Cassette 504 is movably connected to frame 502 to accommodate movement of the cassette due to a shape or size change caused by the exposure of heat and chemicals to the cassette. Furthermore, the cassette lid is removable for clarity. Accordingly, cassette 504 is movably connected to frame 502 by apparatus, such as slidable connections 506 shown in FIGS. 47, 48 and 51 as including a V-shaped projection 510 on cassette 504 slidably accommodated in slot 512 defined in frame 502. Slot 512 has rounded entranceways 514 to facilitate entry of the projection into the slot. As can be seen in FIG. 51, the frame has a frangible frame support tab 516 which supports the projection located in the slot whereby cassette 504 is supported in the proper position in the frame during processing. A slidable connection 506 is located at each corner of the frame whereby the cassette is properly supported.

Figure 48:
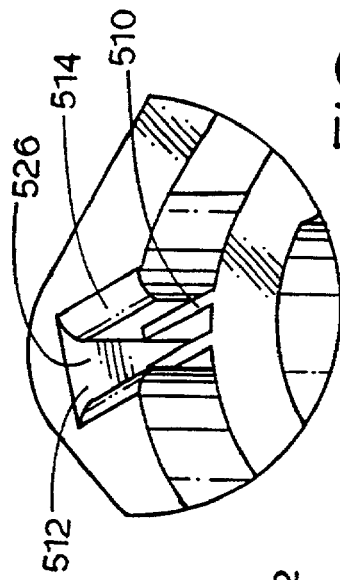
Figure 54:
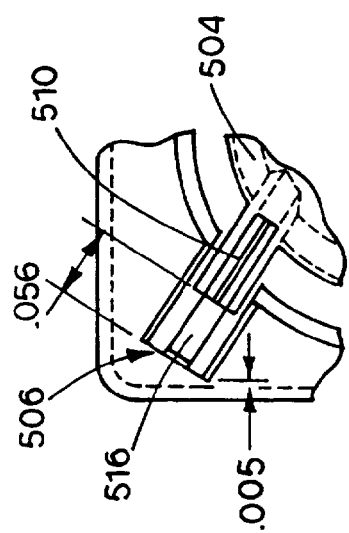
Figure 52:
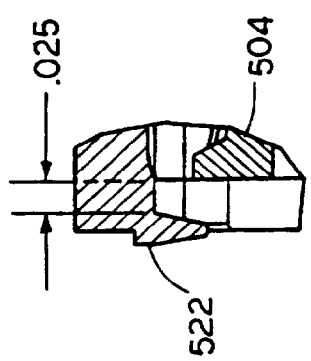

As can be seen in FIG. 51, frame 502 has an open bottom plane with cassette 504 being supported in the frame so bottom 520 is located in the bottom plane of the frame. Thus, the only support provided to the cassette is from tabs 516. Movement of cassette 504 in a direction opposite to the support associated with tabs 516 is prevented by cassette retainer elements 522 on frame 502 near the top plane of the frame and which engage top rim 524 of cassette 504. As can be seen in FIG. 52, retainer elements 522 are flexible in a direction which will permit movement of cassette 504 past the retainer element toward the bottom plane of the frame, but are not flexible in a direction which will permit movement of the cassette in the opposite direction. This feature permits cassette 504 to be forced into frame 502 from one direction, but will be held in that frame once in place such as shown in FIG. 47. The cassette can move within the frame to accommodate swelling of the cassette, but will not separate from the frame due to the limit stops provided by tabs 516 and retainer elements 522. The V-shape of projections 510 permits these projections to slidably engage the walls of the frame adjacent to the slots to control movement of the cassette in the frame yet provide support to the cassette in the frame. As shown in FIGS. 48 and 54, the projections do not engage rear wall 526 in the unswelled condition of the cassette so swelling will not create an interference between the projections and the frame.

Figure 50:
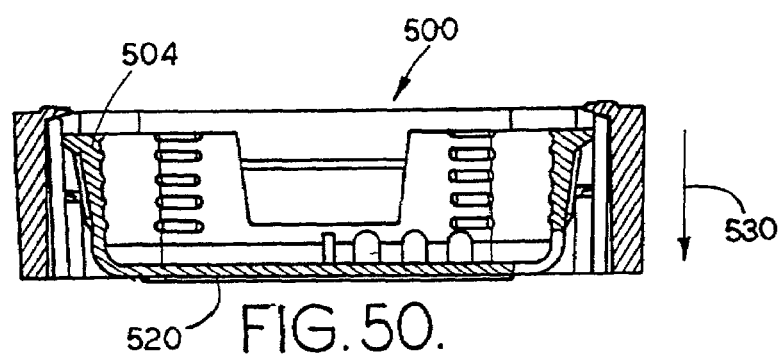
Figure 53:
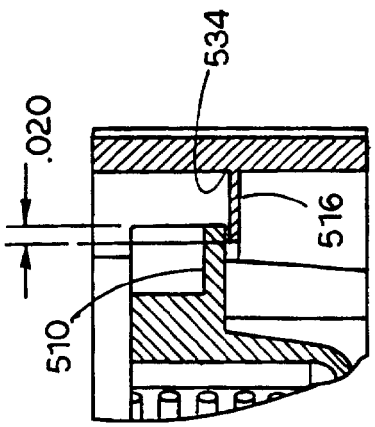

Once a tissue sample has been processed, the cassette can be removed from the frame by pressing on the cassette in a direction indicated in FIG. 50 by the arrow 530. This forces the cassette out of the frame into a bed that is adapted to receive the treated cassette, such as paraffin or the like. Movement in direction 530 is resisted by tabs 516. However, these tabs are frangible, and can even include stress notches, such as notch 534 shown in FIG. 53, to break away thereby permitting further movement of the cassette in direction 530.

Figure 71:
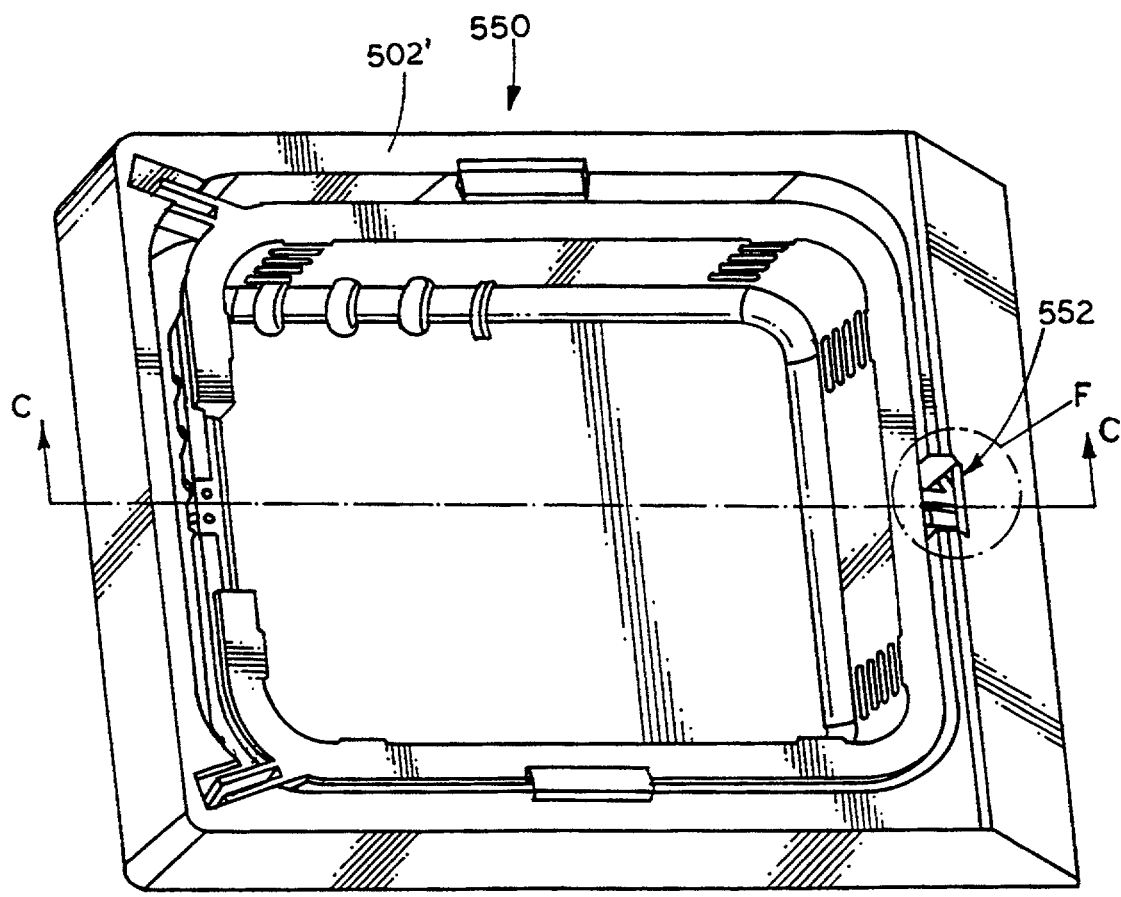
FIG. 71 is a top perspective view of a tissue biopsy sample holding unit.
Figure 73:
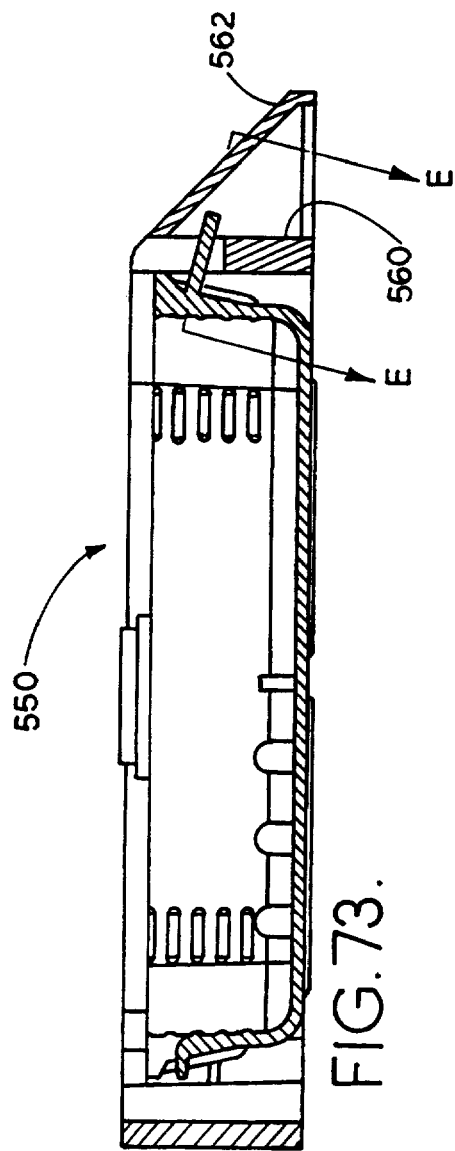
FIG. 73 is a side elevational view of the unit shown in FIG. 71.
Figure 72:
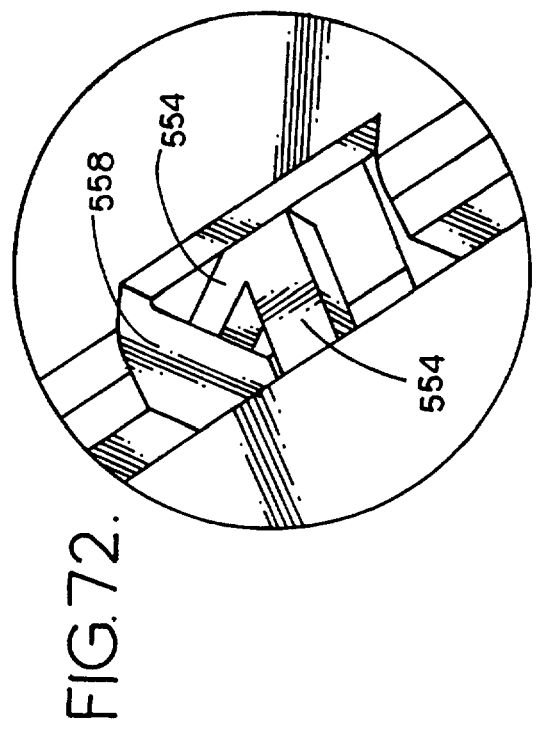
FIG. 72 is a detail of FIG. 71.
Figure 74:
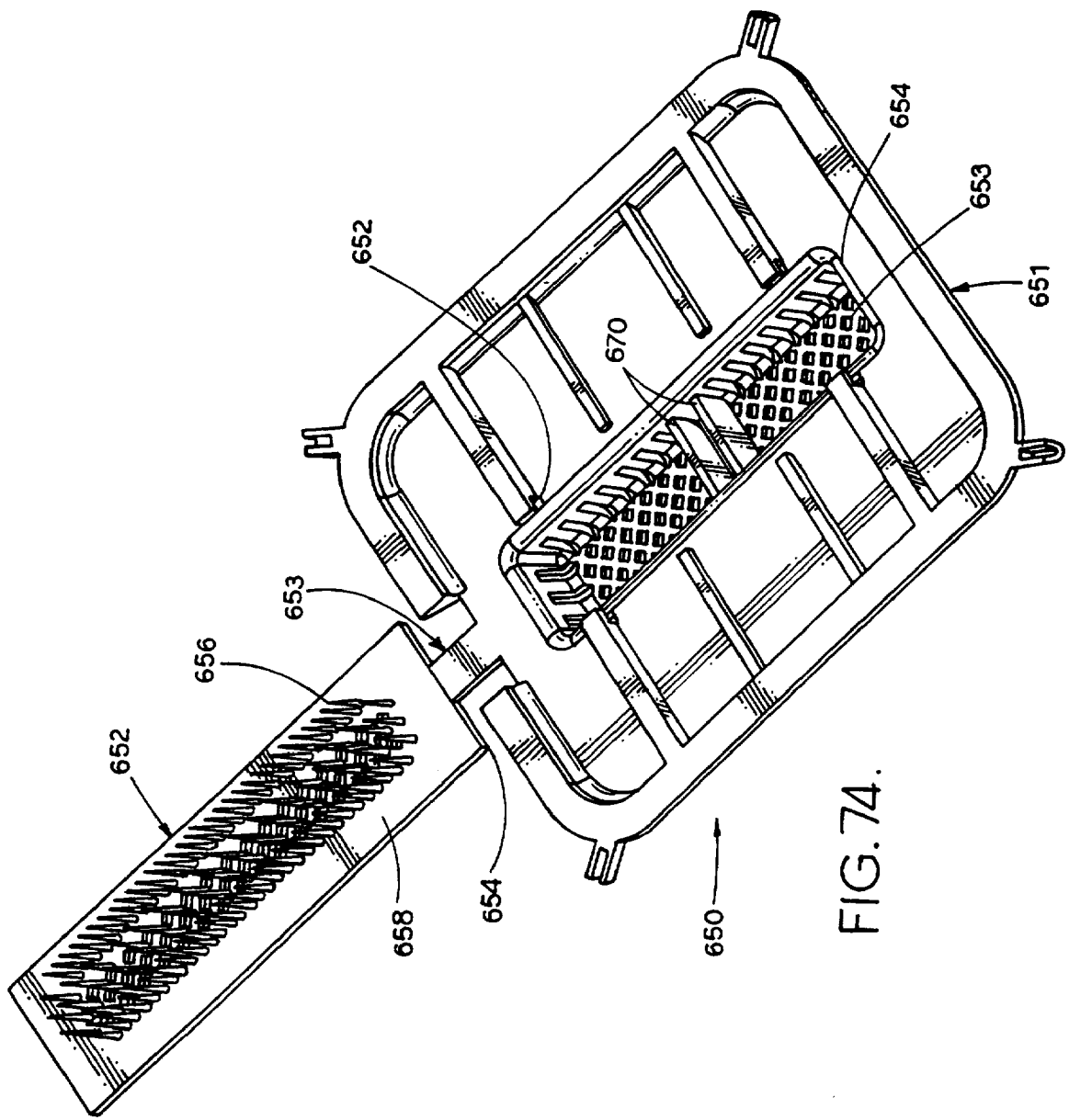
FIG. 74 is a top perspective view of a cassette.
Figure 75:
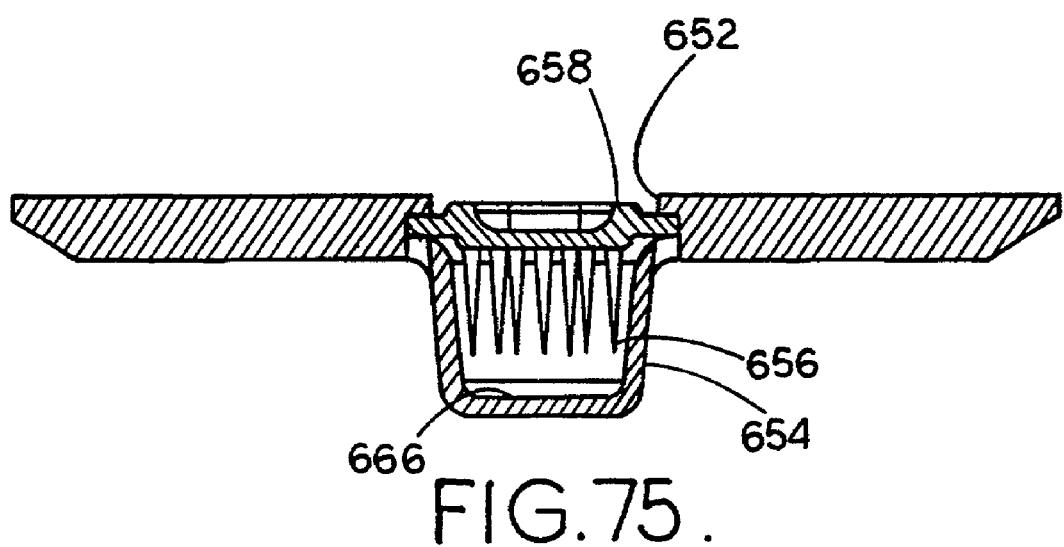
FIG. 75 is an end elevational view of the cassette shown in FIG. 74 in the closed condition.
Figure 78A:
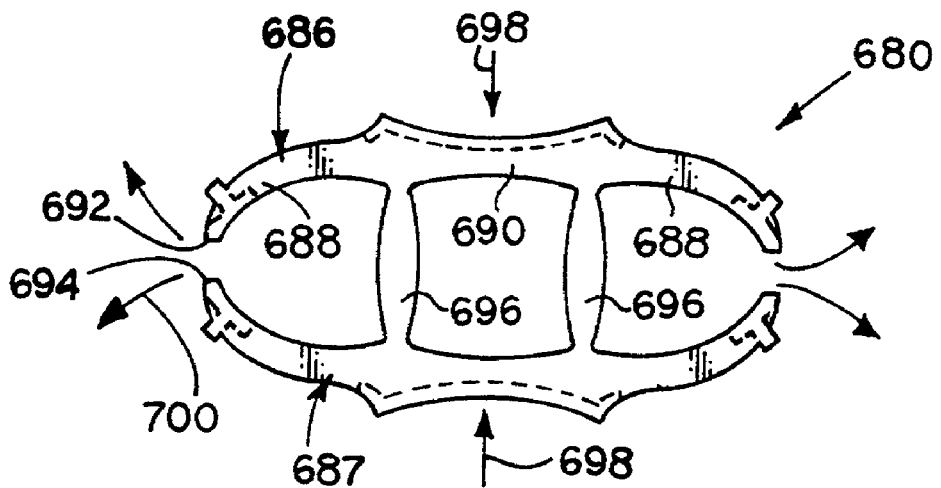
FIG. 78a is a top plan view of a tissue orientation device.
Figure 78B:
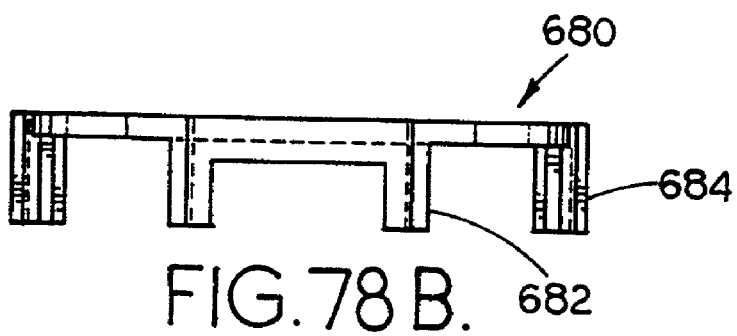
Figure 78C:
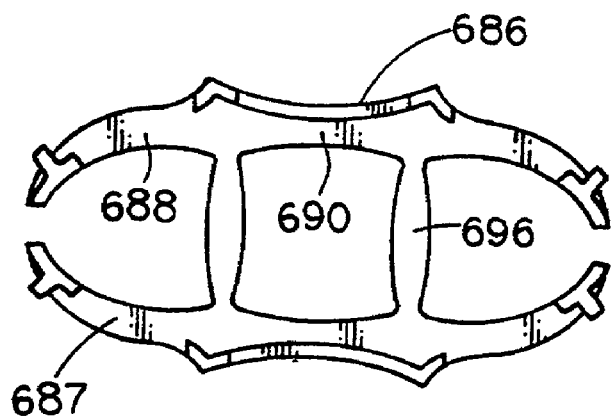
Figure 78D:
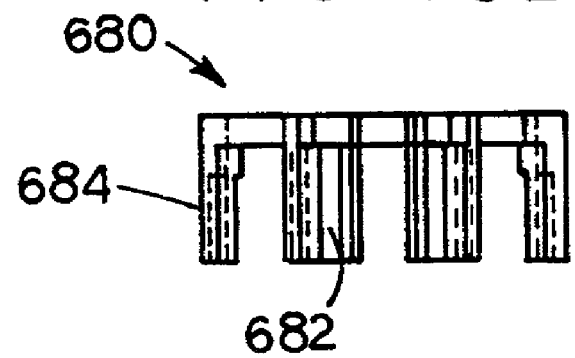
Figure 79:
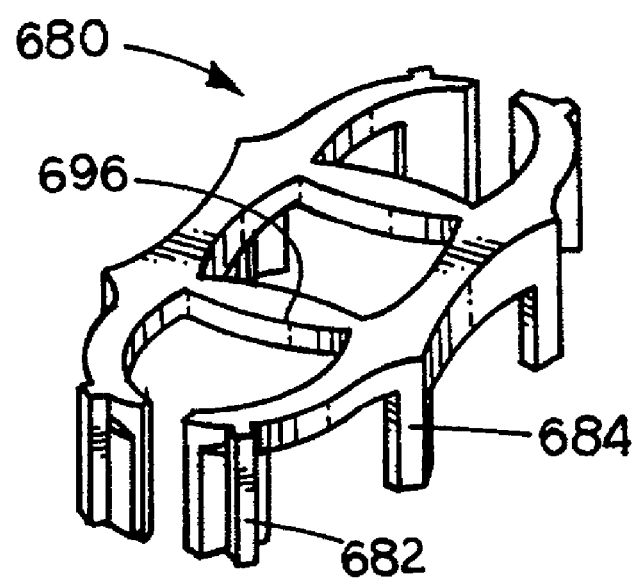

Unit 500 is one form that will accommodate swelling of the cassette, another unit 550 is shown in FIG. 71. Unit 550 is similar to unit 500 but also includes a lock 552 which replaces two of the corner elements 506 (compare FIGS. 47 and 71) so unit 550 only has two corner elements and lock 552 to serve the function of the four elements 506 in unit 500. Lock is shown in FIGS. 71 and 72 as including two arrow-shaped projections 554 attached to the cassette and which extend into a slot 558 defined in frame 502'. The elements 554 are flexible and include first frame engaging elements 558 which can flex in a direction that permits the elements 554 to pass into slot 558 and lock against the frame adjacent to the slot, but will prevent retrograde movement of the elements 554 back out of the slot thereby locking the cassette to the frame once the elements are located in the slot. As shown in FIG. 73, the lock 552 is angled downwardly and is supported by a portion 560 of the frame to add further support to the cassette in the frame. As indicated in FIG. 73, frame 502' can include a writing surface 562 for receiving appropriate tissue information. All frames disclosed herein can include appropriate writing surfaces if suitable. By comparing FIGS. 47 and 71, it can be seen that the two corner elements in unit 550 are angled differently from the corner elements in unit 500 so the unit 550 elements will co-operate with lock 552 whereas the corner elements in unit 500 co-operate with each other.

Figure 57:
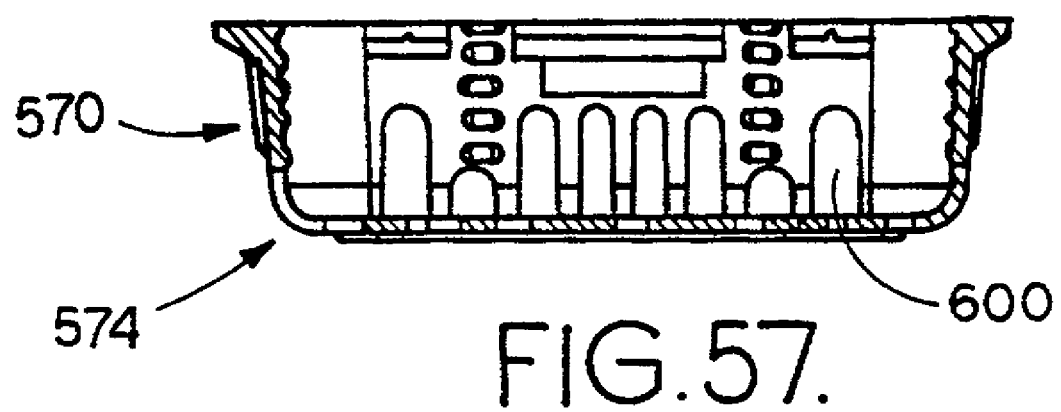
Figure 62:
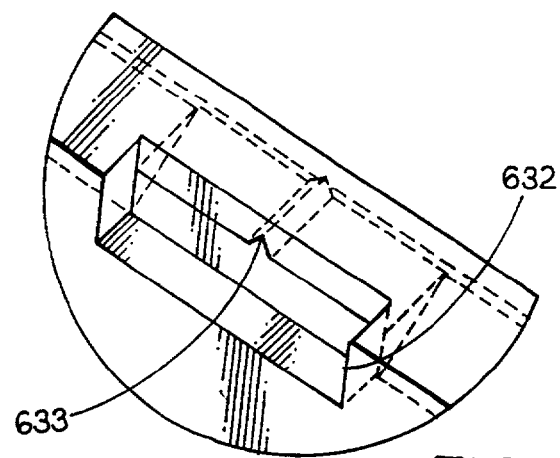
FIG. 62 is a detail view of FIG. 61.

A cassette 570 is shown in FIGS. 55–57. Cassette 570 is not shown with tabs or locks. This cassette design uses side slots in the cassette which correspond to previously discussed frame tabs 516. A Break away notch in FIG. 62 is breakable at the notch. However, as will be understood by those skilled in the art, cassette 570 can be modified to include tabs and locks as above discussed. Cassette 570 includes a bottom portion 572 and a lid 574 which is movably connected to the bottom portion by a hinge 576. Bottom portion 572 is divided into four quadrants, such as quadrant 580, and includes a multiplicity of slots, such as slot 582, which are elongated and have a long axis that is directed toward the center 590 of the cassette. The slots are shaped and oriented in this manner so that a microtome blade will smoothly slice through the bottom surface. With the slots at an angle, the interface edge between the paraffin and the plastic will be presented to the blade as a point instead of a parallel surface thereby efficating the cutting process. In this manner, the microtome blade slices a consistent slice no matter which way the cassette is oriented in the microtome chuck. In addition, a very open pattern of slots is used to allow for a free exchange of fluids in the processor.

As shown in FIG. 56, the slots are oriented to rise up the sides of the cassette. The slots remove as much plastic as possible from the side walls of the cassette. In addition, the plastic cuts easier when surrounded by paraffin, therefore with large slots in the side walls of the cassette, the sectioning process is more efficient.

Lid 574 cooperates with bottom portion 572 to capture tissue inside the sectionable cassette. The lid not only prevents tissue loss but also maintains the orientation and placement of tissue in the cassette once the lid is closed. Because tissues of different thicknesses will be used in the cassette, the cassette must accommodate such different sized samples, and lid 574 achieves this. Lid 574 is attached to bottom portion 572 by hinge 576 that is movable in several directions, including a direction that permits the lid to move toward and away from the bottom portion as well as a direction that permits the lid to move in directions 592 and 594. Hinge 576 is a double hairpin which can be stretched to permit the lid to be placed over, or into, the bottom portion while tissue is located in the bottom portion. Movement of the lid on the hinge with respect to the bottom portion will accommodate tissue of a thickness that differs from a tissue that is accommodated prior to movement of the lid with respect to the bottom portion. The lid also has a multiplicity of slots, such as slot 600, that are organized in four quadrants, such as quadrant 602, and are elongated to have the long axis thereof extend parallel to a diagonal of the lid. The lid is held in place on the bottom portion by a friction fit between the walls of the lid and the walls of the bottom portion. Ladder like elements on the sides of the cassette can also be included.

The lid can include tissue-retaining projections, such as projection 604, which hold tissue in place in the cassette.

The lid can thus be moved with respect to the bottom portion to be positioned to accommodate tissue samples of nearly any thickness and such samples will be securely held in the cassette. Thus, once tissue is captured in the cassette, the tissue need not be manipulated again after tissue processing. The tissue will not move around inside the cassette and will thus maintain its spacing and orientation throughout the embedding process. The lid is locked to the bottom portion by a lip or projection 605 on the lid engaging grooves, such as bump or groove 606 shown in FIG. 59, on the inside wall of the bottom portion.

As shown in FIG. 55, a T-shaped projection 610 is located on one wall of the bottom portion. This is received in a slot defined in the frame to attach the cassette to the frame. The slot is similar to slot 558 (shown in FIG. 72) and captures projection 610. The engagement of projection 610 with the frame keeps the cassette attached to the frame. If information about the tissue in the cassette is noted on writing surface 562 of the frame, it is important to keep the cassette attached to the frame. The lock between the cassette and the frame accomplishes this objective.

Figure 70:
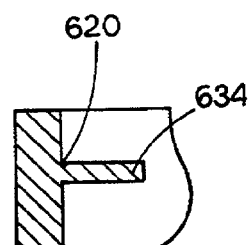
FIG. 70 is a detail view of FIG. 69.

Another form of the frame is shown as frame 611 in FIGS. 67–70 and as frame 611' in FIGS. 64–66, with retainer projections 612 located near the top surface of top rim 614 and extending inwardly of the bottom portion of the frame unit, and supporting tabs, such as tab 616, on the inner surface of wall 618 of the frame unit bottom portion. The cassettes shown in FIGS. 55–63 uses side supporting tabs instead of V-shaped projections. As shown in FIG. 70, tabs 616 can include a stress notch or joint 620 to ensure that the projection will properly fold out of the way of the cassette as the cassette is passed through the frame. The cassette rests on tabs 616 while projections 612 prevent movement of the cassette out of the top of the frame. When desired, the cassette can be forced out of the bottom of the frame by pushing in direction 622 to break the tabs 620 and free the cassette to move into the paraffin as above discussed.

Figure 61:
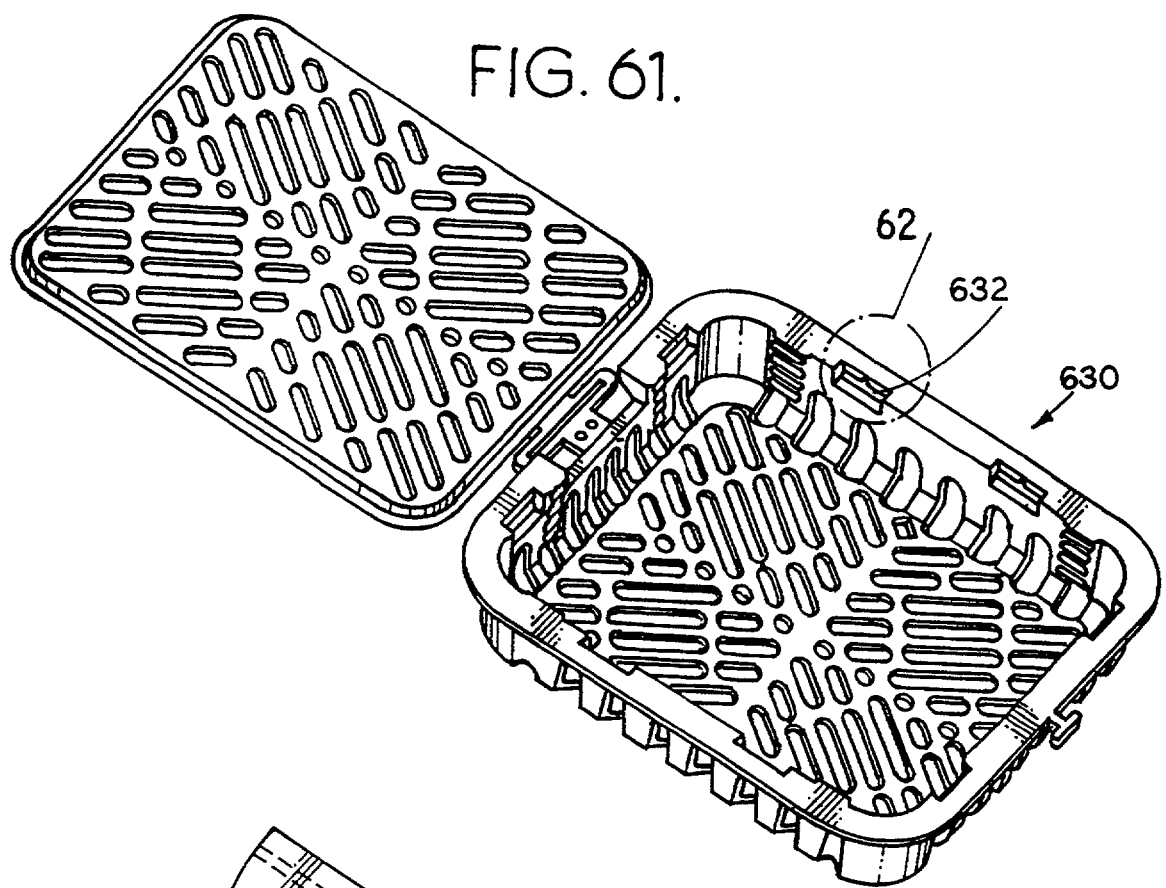
FIG. 61 is a to perspective view off a cassette with a lid attached thereto.
Figure 63:
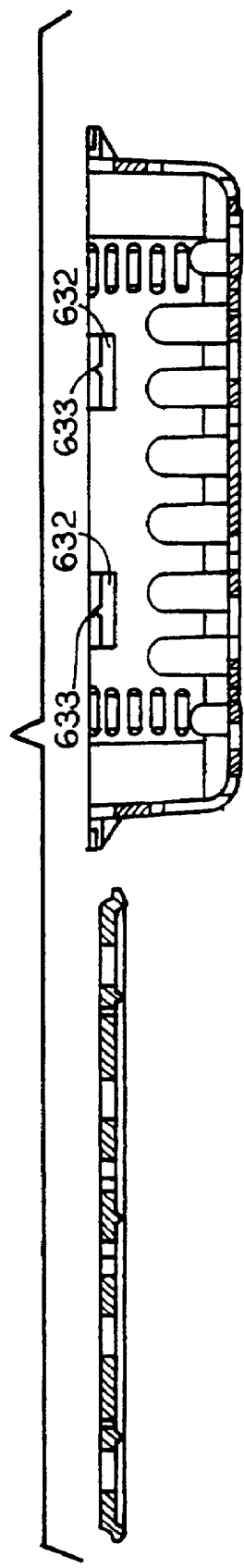
FIG. 63 is a side elevational view of the cassette shown in FIG. 61.
Figure 61A:
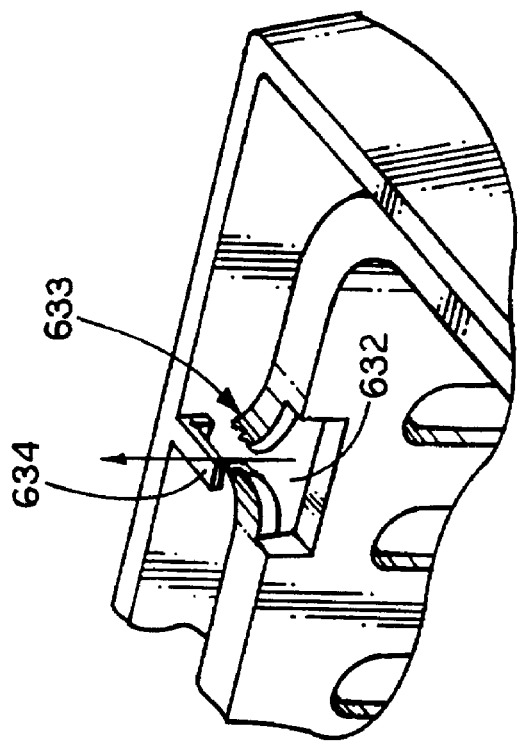
FIG. 61A is a perspective view of a portion of FIG. 61.
Figure 67:
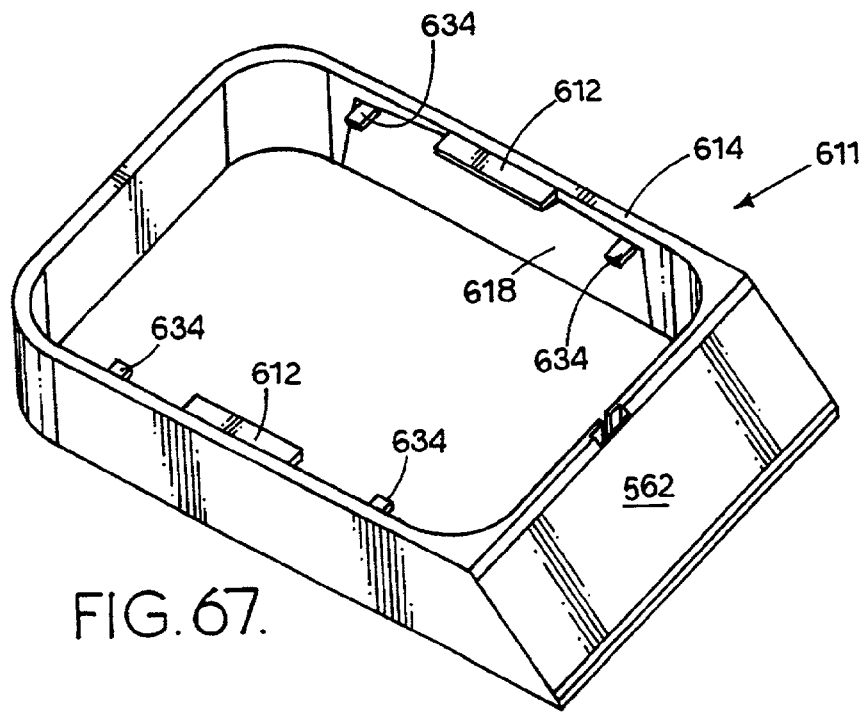
FIG. 67 is a perspective view of a frame.
Figure 68:
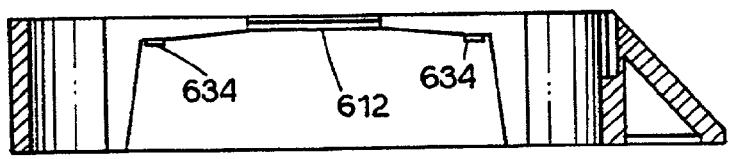
FIG. 68 is a side elevational view of the frame shown in FIG. 67.
Figure 69:
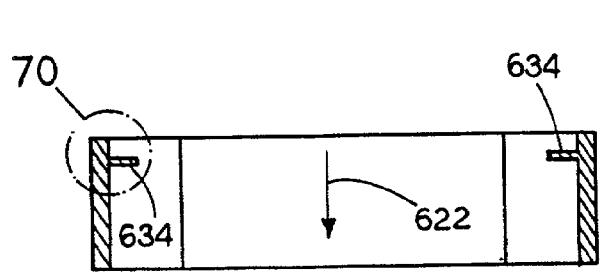
FIG. 69 is an end elevational view of the cassette shown in FIG. 67.

Yet another form of the cassette is shown in FIGS. 61–63 as cassette 630 which includes a plurality of slots 632 defined in the cassette wall and which accommodate corresponding projections 634 on the frame to hold the cassette in place in the frame. As can be seen in the figures, a V-notch 633 is defined in the cassette and creates a thin stress riser where the cassett lip can fracture to release the cassette from the frame tabs 634.

In addition, the cassette can be colored to provide a histotech with an indicator during the facing operation of microtomy. During the facing operation, the histotech will cut through the bottom surface of the cassette to obtain access to the tissue inside the cassette. If the cassette is colored, the histotech will be signalled when to stop facing the paraffin block, and when the colored plastic disappears, to begin cutting thin ribbons for slide. The color of the cassette can be chosen so tissue stains will not be interfered with. Such tissue stain interference would be distracting to the pathologist.

The material of the cassette can be manipulated to further control the swelling of the cassette thereby making the cassette compatible with a wide variety of processing chemicals. For example, different types of plastics can be alloyed together to create a material which is both easy to cut in a microtome and which survives a variety of chemicals. By melt blending high molecular weight and low molecular weight plastics together, the ease of cutting certain materials is maintained while the chemical resistance of other materials is also established. Fluorination of the plastic cassette can be carried out to further modify the material of the cassette to meet the desired goals. Blending filler materials, such as finely ground talc, with the material will alter the properties of the material to reduce swelling from the processing solvents while maintaining the ability of the material to be cut in a microtome.

Chemical solvents such as acetone, xylene, D-Limonene, Aliphtic hydrocarbons, Formalin, Methyl Alchol, ethanol, Isopropanol, and hot pariffin, and the like are some of the most commonly used reagents for tissue processing. This creates a challenge to find a polymer that will withstand each or combinations of these reagents while still maintaining the mechanical integrity of the cassette. In addition, materials which are highly resistant to different chemicals used to process tissue are desirable to use. Flouropolymers which are injection moldable such as FEP are desirable as the chemicals used for processing become more aggressive. Other materials include PTFE, FEP, PFA, ETFE, ECTFE, PCTFE and PVDF which are commercially available through Complex Plastics, Inc as of the date of this application, TEFLON© PFA 340, FEP 100, TEFZEL HT-2181, HYTREL G5544 and HYTREL G4774, all trademarked products of DuPont, and all available from DuPont.

Biopsy Cassette

A biopsy cassette 650 is shown in FIGS. 74–77. Cassette 650 is configured to fit into one of the above-discussed frames in the manner of a standard tissue cassette. Cassette 650 includes a bottom portion 651 and a lid portion 652 hingeably attached thereto by a hinge 653. Bottom portion 651 has a multiplicity of holes 653 defined in the bottom thereof, and these holes are sized to prevent the escape of small tissue samples. A long and narrow well 654 is located in bottom portion 651 and confines tissue samples in a manner that is amenable to microtomy and to microscopic examination when converted to slides. Because the well is narrow, the corresponding paraffin mold will be thin and narrow also. This allows the histotech to place many slices from the microtome on a single slide. This is advantageous for the pathologist because he can see as many samples as possible on a single slide. The biopsy cassette 650 also includes tissue-retaining feathers 656 on a top element 658. The feathers trap the tissue against the bottom wall 660 of the cassette to make certain that the samples are held in one plane. The projections 656 are long and thin enough to prevent any permanent deformation of the tissue during processing. These projections are necessary to keep the tissue against the bottom surface of the cassette to make certain that all the tissue is maintained in one plane for sectioning regardless of the tissue thickness. The projections 656 need to be soft enough so they will deflect away from the tissue sample and not penetrate the sample. If these feathers were constructed of a material that did not deflect, then penetration of the sample would cause tissue distortion, which would appear as an undesirable artifact under microscopic examination. Because of the projection flexibility, samples of various thicknesses can be accommodated in the same cassette. The projections are very thin and are approximately ½ mm from the bottom inside surface 660 of the cassette well. Most tissue biopsies are at least one mm and therefore will be retained by the projections. The projections are very thin and fragile and thus will cause no artifact on a tissue sample. Cassette 650 includes locking elements on the lid portion 652 which engage corresponding locking elements on the well 654 to retain the lid in place and prevent it from coming loose during processing. One form of locking feature is a snap fit, but other forms of lock can be used without departing from the scope of the present disclosure.

As shown in FIG. 76, vertical walls 670 are located in the well so thin shave biopsies can be placed on edge while maintaining their vertical orientation during processing.

Orientation Device

Shown in FIGS. 78a-80 is a normally closed orientation device 680 which is used to help align and orient long thin tissue samples. This orientation will allow a pathologist to hold the tissue samples vertically while manipulating the orientation device with a pair of forceps. Device 680 includes two inner legs 682 and two outer legs 684 attached to pincher elements 686 and 687. Pincher elements 686 and 687 are each concavo-convex with two convex portions 688 separated by a concave portion 690. Convex portions 686 have inner tips 692 and 694 in confronting relationship with each other. Crossbars 696 extend between the pincher elements 686 and 687. The crossbars act as fulcrums so when the pincher elements are squeezed toward each other by inward pressure acting on elements 690 in the directions 698, tips 692 and 694 are moved in directions 700 away from each other. Device 680 is designed to be biased in a direction opposite to direction 698 and thus to bias tips 692 and 694 toward each other. Therefore, when the pinching force in direction 698 is released, the natural bias of the material forces the tips 692 and 694 together.

Figure 80:
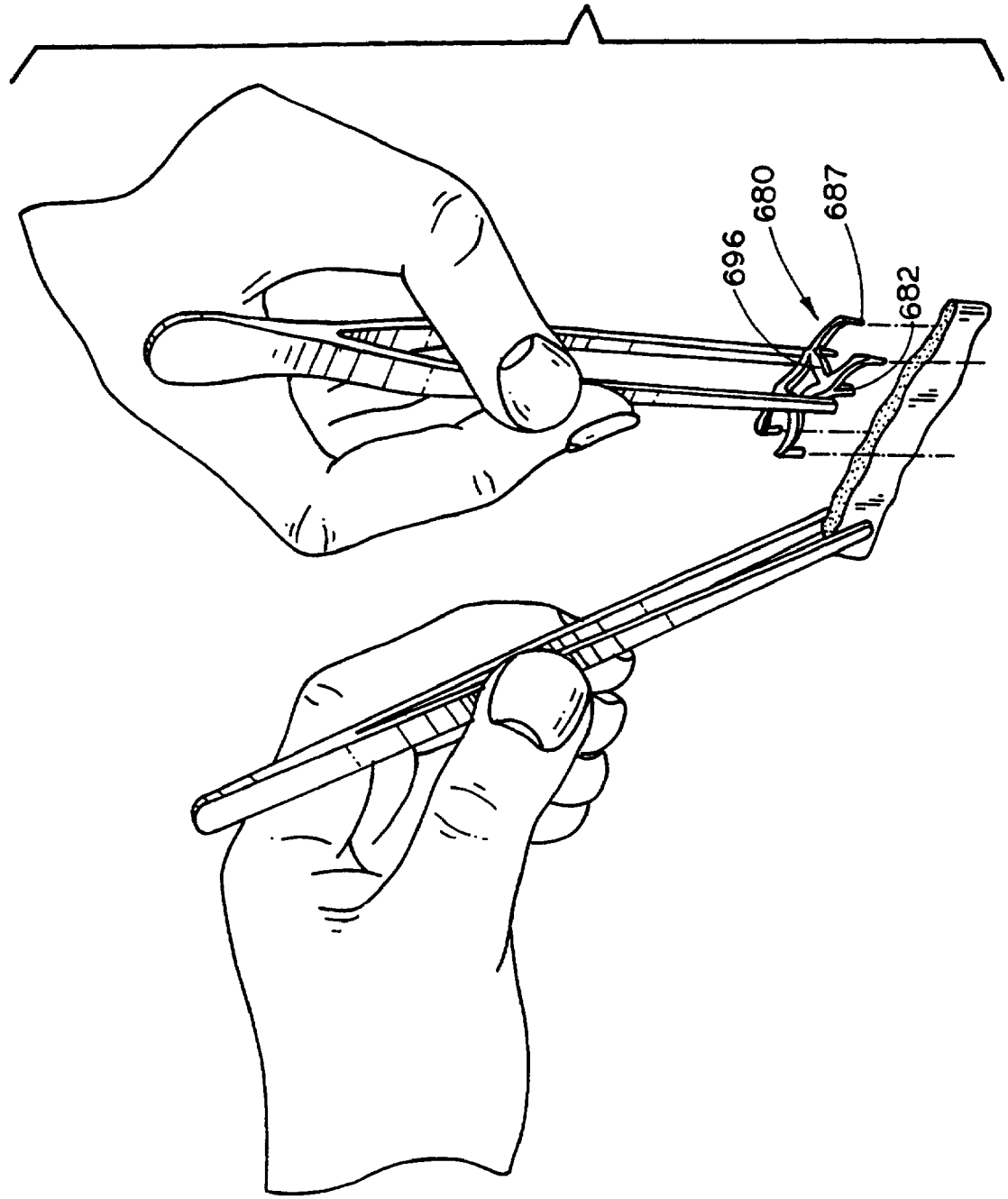

As indicated in FIG. 80, a sample of tissue is captured between tips 692 and 694 by squeezing device 680 in direction 698, placing the tissue between tips 692 and 694, and releasing the device. The device thus captures the tissue, and will maintain it in an upright orientation because legs 682 and 684 support the device. Device 680 can then be placed in a sectionable cassette, processed, embedded and sectioned as above described. It is noted that the orientation device 680 is embedded in the paraffin just as the sectionable cassette is. The orientation device is constructed of material similar to the sectionable cassette; therefore, it can be cut with a microtome blade during slide preparation. Legs 682 and 684 of the orientation device are constructed of special plastic as disclosed above and are microtome sectionable and will have no detrimental effects on slide preparation.

Figure 81:
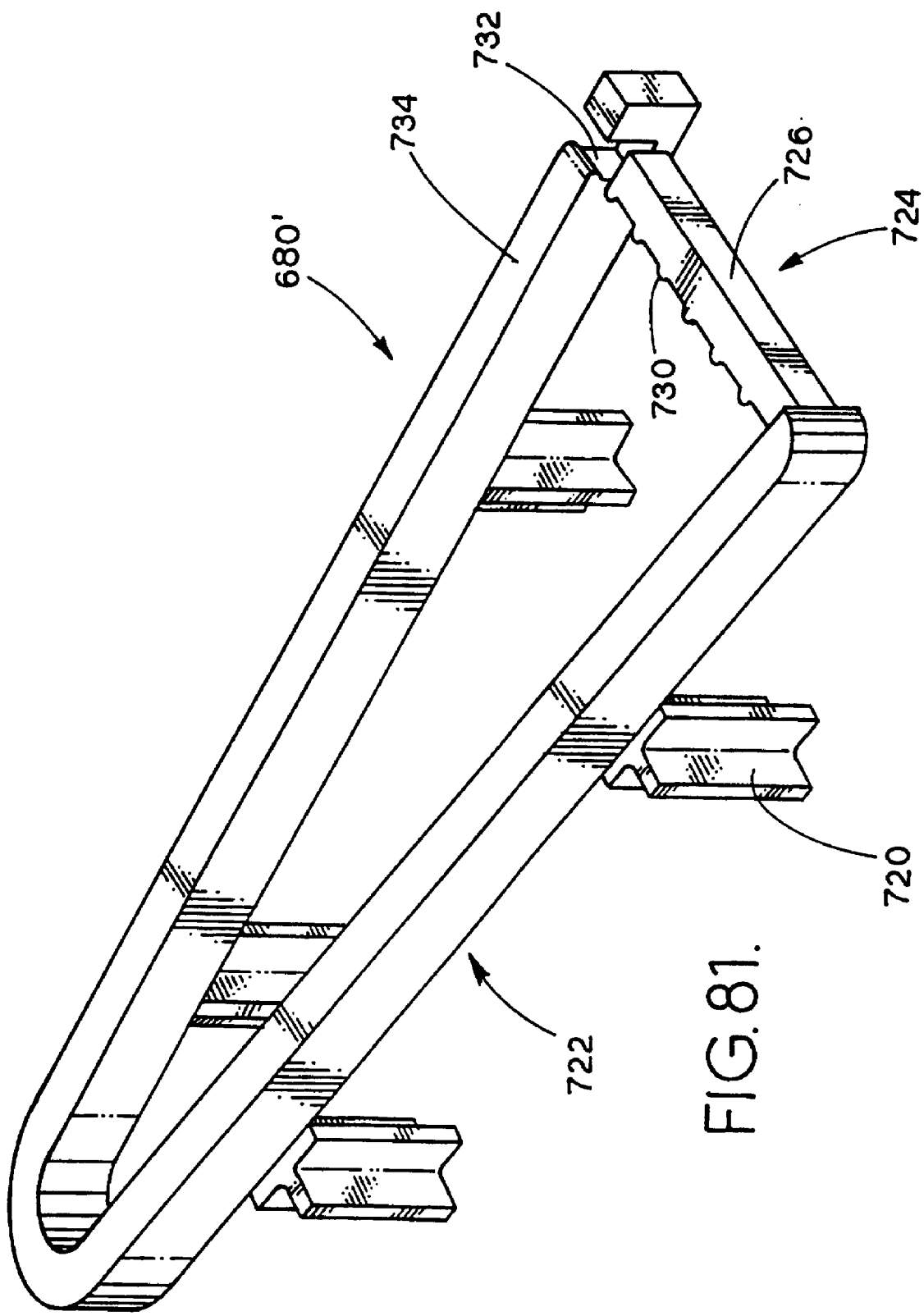
FIG. 81 is a perspective view of another form of tissue orientation device.
Figure 82:
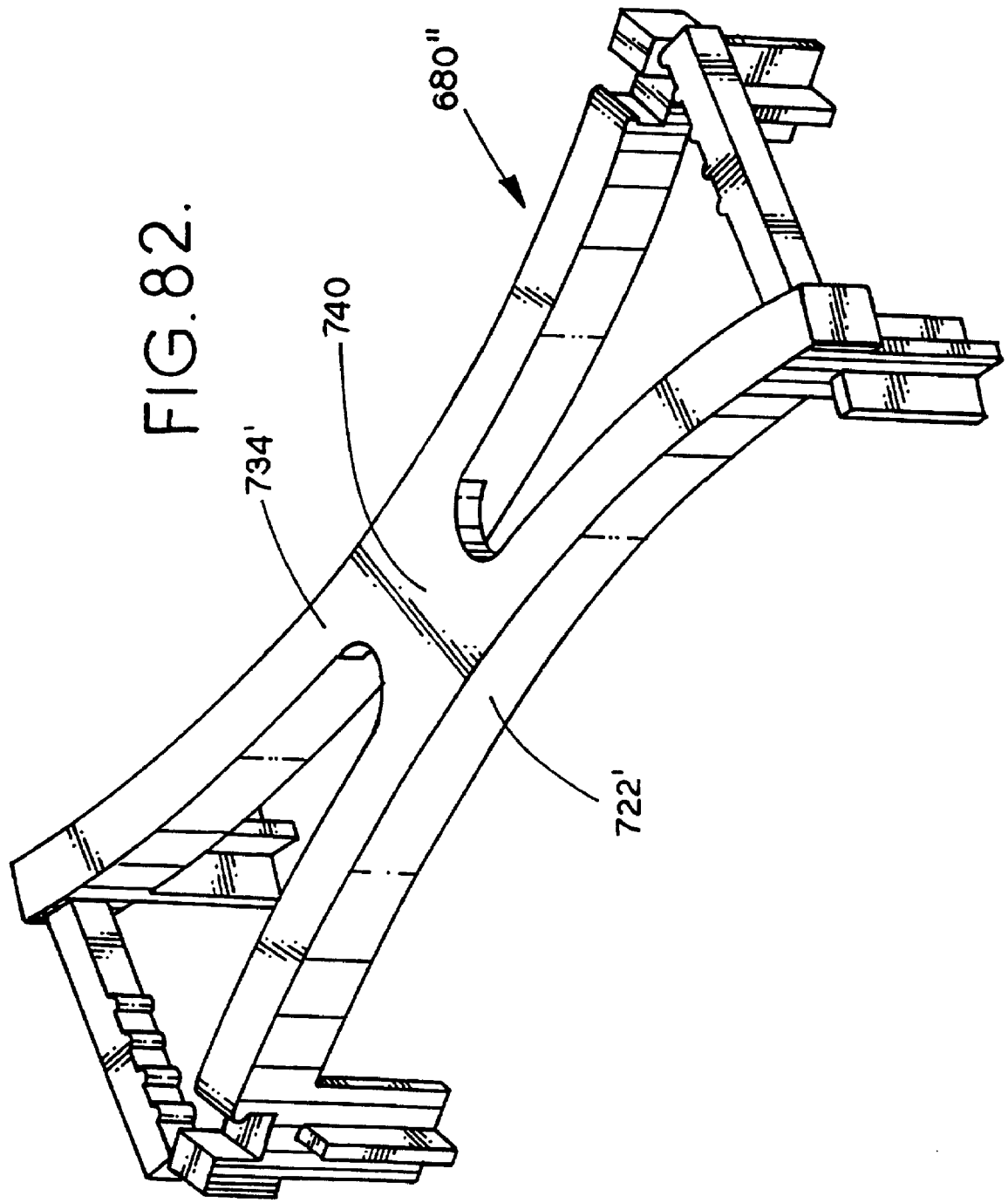
FIG. 82 is a perspective view of another form of tissue orientation device.

Other forms of the orientation device can also be used, and two alternative forms are shown in FIGS. 81 and 82 as normally open devices 680' and 680". Device 680' includes legs 720 connected to a hairpin shaped pincher element 722. A lock 724 includes a cross beam 726 pivotally connected at one end thereof to one portion 728 of the element 722 and having a plurality of projection elements 730 on an inner surface thereof. A locking slot 732 is defined in portion 734 in position to receive the crossbeam. Projections 730 engage portion 734 adjacent to slot 732 to lock portion 722 to portion 734. Tissue is trapped between the portions, and the legs orient the device to maintain the tissue upright.

Device 680" is X-shaped and has locks 7241 on each end, with a crossbar 740 supporting the portions 722' and 734'. Other configurations can also be used without departing from the scope of the present disclosure as will occur to those skilled in the art based on the teaching of this disclosure.

Thus, it is seen that a system and method for harvesting and handling tissue samples is provided. One skilled in the art will appreciate that the present invention can be practiced by other than the preferred embodiments which are presented in this description for purposes of illustration and not of limitation, and the present invention is limited only by the claims which follow. It is noted that equivalents for the particular embodiments discussed in this description may practice the invention as well.

The invention claimed is:

1. A platform comprising:
a microtome sectionable tissue support which is formed of material which can be successfully sectioned in a microtome, is resistant to histological stains, and is resistant to degradation from solvents and chemicals used to fix, process and stain tissue; and an embedding medium in which said tissue support is embedded.

2. A tissue sample container comprising:
a tissue support, said tissue support being formed of material which can be successfully sectioned in a microtome, resistant to histological stains, resistant to degradation from solvents and chemicals used to fix, process and stain tissue; and
deflectable structure which engages and retains tissue in place during processing and embedding.

3. A biopsy tissue harvesting device which deposits a biopsy sample onto a tissue support directly from a harvesting device comprising:
a tissue support, said tissue support being formed of material which can be successfully sectioned in a microtome, resistant to histological stains, resistant to degradation from solvents and chemicals used to fix, process and stain tissue.

4. A histological tissue biopsy sample support comprising:
a frame; a tissue support releasably retained on said frame; said tissue support being formed of material which can be successfully sectioned in a microtome, resistant to histological stains, resistant to degradation from solvents and chemicals used to fix, process and stain tissue and is non-distracting during tissue analysis; a microscopic examination sample support on said tissue support; and an embedding medium in which said tissue support is embedded.

5. A histologic tissue biopsy sample orientation device comprising:
supporting legs formed of microtome sectionable material;
normally closed tissue pinchers on said legs; and
pincher openers on said legs.

6. A histologic tissue biopsy sample orientation device comprising:
supporting legs formed of microtome sectionable material;
normally open tissue pinchers on said legs; and
pincher closers on said legs.

7. A platform comprising:
a microtome sectionable tissue support which is formed of material which can be successfully sectioned in a microtome, resistant to histological stains, resistant to degradation from solvents and chemicals used to fix, process and stain tissue and is non-distracting during tissue analysis.

8. A tissue sample container comprising:
   a microtome sectionable tissue support which is formed of material which can be successfully sectioned in a microtome, resistant to histological stains, resistant to degradation from solvents and chemicals used to fix, process and stain tissue and is non-distracting during tissue analysis; and
   deflectable structure which engages and retains tissue in place during processing and embedding.

9. A platform comprising:
   a tissue support which is microtome sectionable; and an embedding medium in which said tissue support is embedded, said embedding medium being formed of material that can be successfully sectioned in a microtome whereby said tissue support and said embedding medium may be simultaneously sectioned in the microtome.

10. A histologic tissue sample support, said support configured to hold a tissue sample and being formed of a material which can be successfully sectioned in a microtome, said support further being resistant to degradation from solvents and chemicals used to fix and process the tissue sample during a histologic procedure.

11. The histologic tissue sample support of claim 10, wherein said tissue sample support is embedded in a tissue embedding medium, said embedding medium being formed of material which can be successfully sectioned in a microtome.

12. The histologic tissue sample support of claim 10, wherein said support further comprises:
   a cassette having a bottom portion configured to hold the tissue sample, and a lid configured to couple with said bottom portion to hold the tissue sample in a desired orientation.

13. The histologic tissue sample support of claim 12, wherein said bottom portion further comprises five sides, the five sides including a bottom wall and four side walls defining an interior space for holding the tissue sample, wherein the material can be successfully sectioned by slicing through said bottom wall to expose the tissue sample.

14. The histologic tissue sample support of claim 12, wherein said lid is movably connected to said bottom portion.

15. The histologic tissue sample support of claim 10, wherein said material forming said support is at least translucent so as to be non-distracting during tissue analysis.

16. The histologic tissue sample support of claim 10, wherein said material is colored to provide a signal as to when to stop a facing operation thereof while sectioning said support in the microtome.

17. The histologic tissue sample support of claim 10, further comprising:
   deflectable structure which engages and retains the tissue sample in place during processing, embedding and sectioning in the microtome.

18. The histologic tissue sample support of claim 10, wherein said support is formed of a polymer.

19. The histologic tissue sample support of claim 18, wherein said polymer is a fluorinated polymer.

20. The histologic tissue sample support of claim 18, wherein said polymer is a fluoropolymer.

21. The histologic tissue sample support of claim 10, wherein said support is porous.

22. The histologic tissue sample support of claim 21, wherein said support includes side edges and elongated slots directed nonparallel to said side edges.

23. The histologic tissue sample support of claim 10, further comprising:
   tissue sample retaining structure configured to engage the tissue sample and holding the sample in place.

24. The histologic tissue sample support of claim 10, further comprising:
   tissue sample retaining structure configured to engage multiple tissue samples and maintain the multiple tissue samples in desired orientations whereby the multiple tissue samples all can be cut by a microtome in a single pass.

25. The histologic tissue sample support of claim 10, wherein said support is non-distracting during tissue examination which is performed subsequent to slide preparation.

26. The histologic tissue sample support of claim 10, wherein said support is resistant to histological stains.

27. A histologic tissue sample support structure, comprising:
   a support member configured to hold a tissue sample and being formed of a material which can be successfully sectioned in a microtome; and
   a tissue embedding medium in which said support member is embedded, said embedding medium being formed of material which can be successfully sectioned in a microtome.

28. A histologic tissue sample cassette, said cassette having a bottom portion configured to hold a tissue sample in a desired orientation and at least one side wall for containing the tissue sample, said cassette further being formed of a material which can be successfully sectioned in a microtome.

29. The histologic tissue sample cassette of claim 28, further comprising:
   a lid configured to couple with said bottom portion to further contain the tissue sample during an embedding process.

30. Apparatus for holding a histologic tissue sample while sectioning the tissue sample in a microtome, the apparatus comprising:
   a frame;
   a tissue sample support coupled to said frame, said support configured to hold the tissue sample and being formed of a material which can be successfully sectioned in a microtome, said support further being resistant to degradation from solvents and chemicals used to fix and process the tissue sample during a histologic procedure.

31. The apparatus of claim 30, wherein said tissue sample support is releasably coupled to said frame and said frame is further configured for releasable securement within a microtome chuck.

32. The apparatus of claim 30, wherein said frame includes an interior and said tissue sample support is sized to fit and move within said interior between at least a first position and a second position, said first position being used during processing of the tissue sample, and the second position being used to expose the tissue outward of said frame in a position for allowing the tissue sample to be sectioned in the microtome.

33. The apparatus of claim 30, further comprising:
   an embedding mold configured to releasably hold said frame and tissue sample support while embedding material is deposited within said embedding mold and frame to embed the tissue sample.

34. The apparatus of claim 30, further comprising:
a tissue embedding medium in which said tissue sample support is embedded, said embedding medium being formed of material which can be successfully sectioned in a microtome.

35. The apparatus of claim 30, wherein said support further comprises:
a cassette having a bottom portion configured to hold the tissue sample, and a lid configured to couple with said bottom portion to hold the tissue sample in a desired orientation.

36. The apparatus of claim 35, wherein said bottom portion further comprises five sides, the five sides including a bottom wall and four side walls defining an interior space for holding the tissue sample, wherein the material can be successfully sectioned by slicing through said bottom wall to expose the tissue sample.

37. The apparatus of claim 35, wherein said lid is movably connected to said bottom portion.

38. The apparatus of claim 30, wherein said material forming said support is at least translucent so as to be non-distracting during tissue analysis.

39. The apparatus of claim 30, further comprising:
deflectable structure which engages and retains tissue sample in place during processing, embedding and sectioning in the microtome.

40. The apparatus of claim 30, wherein said support is formed of a polymer.

41. The apparatus of claim 40, wherein said polymer is a fluorinated polymer.

42. The apparatus of claim 40, wherein said polymer is a fluoropolymer.

43. The apparatus of claim 30, wherein said support is porous.

44. The apparatus of claim 43, wherein said support includes side edges and elongated slots directed nonparallel to said side edges.

45. The apparatus of claim 30, further comprising:
tissue sample retaining structure configured to engage the tissue sample and maintain the sample in a desired orientation.

46. The apparatus of claim 30, further comprising:
tissue sample retaining structure configured to engage multiple tissue samples and maintain the multiple tissue samples in desired orientations whereby the multiple tissue samples all can be cut by a microtome in a single pass.

47. The apparatus of claim 30, wherein said support is non-distracting during tissue examination which is performed subsequent to slide preparation.

48. The apparatus of claim 30, wherein said support is resistant to histological stains.

49. The apparatus of claim 30, wherein said material is colored to provide a signal as to when to stop a facing operation thereof while sectioning said support in the microtome.

50. A tissue sample container assembly comprising:
a histologic tissue sample support, said support being configured to hold a tissue sample and being formed of a material which can be successfully sectioned in a microtome, said support further being resistant to degradation from solvents and chemicals used to fix and process the tissue sample during a histologic procedure;
a container body with an opening for receiving said histologic tissue sample support; and
a cap configured to selectively open and close said opening.

51. The tissue sample container assembly of claim 50, wherein said cap allows injection of the tissue sample into said container body.

52. The tissue sample container assembly of claim 50, wherein said support further comprises:
a filter having a bottom portion configured to hold the tissue sample, and a lid configured to couple with said bottom portion to hold the tissue sample in a desired orientation.

53. The tissue sample container assembly of claim 52, wherein said bottom portion further comprises five sides, the five sides including a bottom wall and four side walls defining an interior space for holding the tissue sample, wherein the material can be successfully sectioned by slicing through said bottom wall to expose the tissue sample.

54. The tissue sample container assembly of claim 52, wherein said lid is movably connected to said bottom portion.

55. The tissue sample container assembly of claim 50, wherein said material forming said support is at least translucent so as to be non-distracting during tissue analysis.

56. The tissue sample container assembly of claim 50, further comprising:
deflectable structure which engages and retains the tissue sample in place during processing, embedding and sectioning in the microtome.

57. The tissue sample container assembly of claim 50, wherein said support is formed of a polymer.

58. The tissue sample container assembly of claim 57, wherein said polymer is a fluorinated polymer.

59. The tissue sample container assembly of claim 57, wherein said polymer is a fluoropolymer.

60. The tissue sample container assembly of claim 50, wherein said support is porous.

61. The tissue sample container assembly of claim 60, wherein said support includes side edges and elongated slots directed nonparallel to said side edges.

62. The tissue sample container assembly of claim 50, wherein said material is colored to provide a signal as to when to stop a facing operation thereof while sectioning said support in the microtome.

63. The tissue sample container assembly of claim 50, further comprising:
tissue sample retaining structure configured to engage the tissue sample and maintain the sample in a desired orientation.

64. The tissue sample container assembly of claim 50, further comprising:
tissue sample retaining structure configured to engage multiple tissue samples and maintain the multiple tissue samples in desired orientations whereby the multiple tissue samples all can be cut by a microtome in a single pass.

65. The tissue sample container assembly of claim 50, wherein said support is non-distracting during tissue examination which is performed subsequent to slide preparation.

66. The tissue sample container assembly of claim 50, wherein said support is resistant to histological stains.

67. A cassette for receiving and retaining a tissue sample for processing prior to histological examination, comprising:
a top portion and a bottom portion snap or friction mounted together, the bottom portion having a bottom wall and a side wall each being removable after a procedure is performed to embed the tissue sample in said bottom portion.

68. The cassette of claim 67, wherein said bottom wall and said side wall are removable by sectioning in a microtome while sectioning said cassette and tissue sample after embedding said cassette and tissue sample in an embedding media.

69. The cassette of claim 67, wherein said top and bottom portions are molded of a synthetic plastic material.

70. A cassette for receiving and retaining a tissue sample in a desired orientation for processing and microtoming procedures prior to histological examination, comprising:
a support structure having a porous top, porous bottom and porous sides configured to surround and fix the tissue sample in the desired orientation during the processing and microtoming procedures prior to histological examination.

71. The cassette of claim 70, wherein said porous bottom and said porous sides are removable after a procedure is performed to embed the tissue sample in said support structure.

72. The cassette of claim 70, wherein said porous bottom and said porous sides are removable by sectioning in a microtome during the microtome procedure.

73. The cassette of claim 70, wherein said support structure is molded of a synthetic plastic material.

* * * * *

UNITED STATES PATENT AND TRADEMARK OFFICE
CERTIFICATE OF CORRECTION

| | |
|---|---|
| PATENT NO. | : 7,156,814 B1 |
| APPLICATION NO. | : 09/890177 |
| DATED | : January 2, 2007 |
| INVENTOR(S) | : Warren P. Williamson et al. |

It is certified that error appears in the above-identified patent and that said Letters Patent is hereby corrected as shown below:

Column 3

Line 39, change "lab;" to --lab,--.

Column 4

Line 19, change "parrifin" to --paraffin--.

Column 5

Line 51, delete "is".

Column 6

Line 44, change "accommodates" to --accommodate--.

Line 48, change "processiing" to --processing--.

Column 7

Line 1, change "Thuse" to --Thus-- and "suport" to --support--.

Column 8

Line 42, change "biopsies" to --biopsies,--.

Column 9

Line 2, change "reduces" to --reduce--.

Line 8, change "histotech-nologist" to --histotechnologist--.

Line 26, delete "of the sectionable cassettes".

Line 61, change "necessar-ily" to --necessarily--.

Column 10

Line 64, change "examiination" to --examination--.

UNITED STATES PATENT AND TRADEMARK OFFICE
CERTIFICATE OF CORRECTION

PATENT NO. : 7,156,814 B1
APPLICATION NO. : 09/890177
DATED : January 2, 2007
INVENTOR(S) : Warren P. Williamson et al.

It is certified that error appears in the above-identified patent and that said Letters Patent is hereby corrected as shown below:

Column 11

Lines 21-22, change "unfufilled" to --unfulfilled--.

Column 13

Line 3, delete "to" and change "off" to --of--.

Column 15

Line 60, change "ample" to --sample--.

Column 16

Line 57, change "suport" to --suport--.

Column 17

Line 6, change "manupulable" to --manipulable--.

Line 11, change "comprisng" to --comprising--.

Line 57, change "programmagle" to --programmable--.

Column 18

Line 4, after "alternatively" insert --be--.

Line 21, change "machiine" to --machine-- and change "cold" to --could--.

Line 26, change "pathoogy" to --pathology--.

Line 62, change "infra red" to --infrared--.

Column 19

Line 3, after "analyzed" insert --by--.

Line 6, change "applicaion" to --application--.

Line 11, change "sub-speciality" to --sub-specialty--.

UNITED STATES PATENT AND TRADEMARK OFFICE
CERTIFICATE OF CORRECTION

| | | |
|---|---|---|
| PATENT NO. | : 7,156,814 B1 | |
| APPLICATION NO. | : 09/890177 | |
| DATED | : January 2, 2007 | |
| INVENTOR(S) | : Warren P. Williamson et al. | |

It is certified that error appears in the above-identified patent and that said Letters Patent is hereby corrected as shown below:

Column 22

Line 65, change "automted" to --automated--.

Column 23

Line 2, change "ocersee" to --oversee--.

Line 7, change "conrols" to --controls--.

Column 26

Line 13, change "is" to --it--.

Line 31, delete "and".

Column 27

Line 6, after "necessary" insert --in--.

Line 19, change "including," to --including--.

Column 28

Line 5, change "taught" to --taut--.

Line 10, change "moves" to --move--.

Line 52, change "adapeter" to --adapter--.

Column 29

Line 2, delete "20:".

Column 30

Line 32, change "is" to --can--.

Column 32

Line 22, change "is" to --are--.

UNITED STATES PATENT AND TRADEMARK OFFICE
CERTIFICATE OF CORRECTION

| | |
|---|---|
| PATENT NO. | : 7,156,814 B1 |
| APPLICATION NO. | : 09/890177 |
| DATED | : January 2, 2007 |
| INVENTOR(S) | : Warren P. Williamson et al. |

It is certified that error appears in the above-identified patent and that said Letters Patent is hereby corrected as shown below:

Column 33

Line 1, change "achieves" to --achieve--.

Line 10, delete "35'".

Column 34

Line 27, change "Break" to --break--.

Line 41, change "efficating" to --effecting--.

Column 35

Line 35, change "67 70" to --67-70– and "64 66" to --64-66--.

Line 40, change "uses" to --use--.

Line 56, change "releast" to --release--.

Column 36

Line 21, change "Aliphtic" to --Aliphatic-- and "Alchol" to --Alcohol--.

Line 22, change "pariffin" to --paraffin--.

Line 33, change "Inc" to --Inc.--.

Line 34, change "©" to --®--.

Column 37

Line 27 change "concavo-convex" to --concave-convex--.

UNITED STATES PATENT AND TRADEMARK OFFICE
CERTIFICATE OF CORRECTION

PATENT NO. : 7,156,814 B1
APPLICATION NO. : 09/890177
DATED : January 2, 2007
INVENTOR(S) : Warren P. Williamson et al.

It is certified that error appears in the above-identified patent and that said Letters Patent is hereby corrected as shown below:

<u>Column 38</u>

Line 1, change "7241" to --724--.

Signed and Sealed this

Thirteenth Day of November, 2007

JON W. DUDAS
*Director of the United States Patent and Trademark Office*